(12) United States Patent
Dhingra

(10) Patent No.: US 10,576,090 B2
(45) Date of Patent: *Mar. 3, 2020

(54) MODULATION OF SOLUBILITY, STABILITY, ABSORPTION, METABOLISM, AND PHARMACOKINETIC PROFILE OF LIPOPHILIC DRUGS BY STEROLS

(71) Applicant: Marius Pharmaceuticals LLC, Raleigh, NC (US)

(72) Inventor: Om Dhingra, Morrisville, NC (US)

(73) Assignee: Marius Pharmaceuticals LLC, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/959,626

(22) Filed: Apr. 23, 2018

(65) Prior Publication Data

US 2018/0243319 A1    Aug. 30, 2018

Related U.S. Application Data

(63) Continuation of application No. 13/936,036, filed on Jul. 5, 2013, which is a continuation of application No. 12/983,216, filed on Dec. 31, 2010, now abandoned.

(60) Provisional application No. 61/291,769, filed on Dec. 31, 2009.

(51) Int. Cl.
| | |
|---|---|
| *A61K 31/568* | (2006.01) |
| *A61K 9/107* | (2006.01) |
| *A61K 9/48* | (2006.01) |
| *A61K 31/4985* | (2006.01) |
| *A61K 45/06* | (2006.01) |
| *A61K 9/00* | (2006.01) |

(52) U.S. Cl.
CPC .......... *A61K 31/568* (2013.01); *A61K 9/0053* (2013.01); *A61K 9/107* (2013.01); *A61K 9/1075* (2013.01); *A61K 9/4858* (2013.01); *A61K 9/4866* (2013.01); *A61K 9/4875* (2013.01); *A61K 31/4985* (2013.01); *A61K 45/06* (2013.01); *Y02A 50/465* (2018.01)

(58) Field of Classification Search
CPC .................................................. A61K 31/568
USPC ........................................................ 514/170
See application file for complete search history.

(56) References Cited

U.S. PATENT DOCUMENTS

| | | | |
|---|---|---|---|
| 4,147,783 A | 4/1979 | van der Vies | |
| 4,797,625 A | 1/1989 | Nakazawa | |
| 5,376,641 A | 12/1994 | Ammeraal | |
| 5,567,439 A | 10/1996 | Myers et al. | |
| 5,645,856 A | 7/1997 | Lacy et al. | |
| 6,087,353 A * | 7/2000 | Stewart | A21D 2/16 514/182 |
| 6,248,363 B1 | 6/2001 | Patel et al. | |
| 6,267,985 B1 | 7/2001 | Chen et al. | |
| 6,284,268 B1 | 9/2001 | Mishra et al. | |
| 6,294,192 B1 | 9/2001 | Patel et al. | |
| 6,309,663 B1 | 10/2001 | Patel et al. | |
| 6,383,471 B1 | 5/2002 | Chen et al. | |
| 6,451,339 B2 | 9/2002 | Patel et al. | |
| 6,458,383 B2 | 10/2002 | Chen et al. | |
| 6,468,559 B1 | 10/2002 | Chen et al. | |
| 6,569,463 B2 | 5/2003 | Patel et al. | |
| 6,652,880 B1 | 11/2003 | Aylwin et al. | |
| 6,696,484 B2 | 2/2004 | Liao et al. | |
| 6,720,001 B2 | 4/2004 | Chen et al. | |
| 6,742,488 B2 | 6/2004 | Bonde et al. | |
| 6,743,448 B2 | 6/2004 | Kryger | |
| 6,761,903 B2 | 7/2004 | Chen et al. | |
| 6,838,484 B2 | 1/2005 | Steiner et al. | |
| 6,923,988 B2 | 8/2005 | Patel et al. | |
| 6,977,083 B1 | 12/2005 | Huebler et al. | |
| 6,982,281 B1 | 1/2006 | Chen et al. | |
| 7,138,389 B2 | 11/2006 | Amory et al. | |
| 7,374,779 B2 | 5/2008 | Chen et al. | |

(Continued)

FOREIGN PATENT DOCUMENTS

| | | |
|---|---|---|
| CN | 1010538 B | 11/1990 |
| CN | 102083420 A | 6/2011 |

(Continued)

OTHER PUBLICATIONS

PubChem CID 14870 [online] Retrieved online on Jun. 28, 2018 and [Retrieved from: https://pubchem.ncbi.nlm.nih.gov/compound/2-Hydroxypropyl_dodecanoate#section=Top] (Year: 2005).*

(Continued)

*Primary Examiner* — Taina D Matos Negron
(74) *Attorney, Agent, or Firm* — Clark & Elbing LLP

(57) ABSTRACT

A formulation for drug delivery, providing enhanced modulation of solubility, stability, absorption, metabolism, and/or pharmacokinetic profile of a lipophilic therapeutic agent by formulation with sterols and/or sterol esters, resulting in higher bioavailability of a therapeutic agent administered to a subject in need of such therapeutic agent. The formulation contains a therapeutic agent and a sterol or sterol ester, and can, optionally, further contain a solubilizer and/or an enhancing agent. Also described are pharmaceutical compositions containing the formulations and methods of making and methods of using the formulations and pharmaceutical compositions. Formulations of the disclosure can be constituted to minimize the synthesis of dihydrotestosterone when the therapeutic agent includes testosterone or testosterone esters.

15 Claims, 13 Drawing Sheets

(56) References Cited

U.S. PATENT DOCUMENTS

| | | |
|---|---|---|
| 8,241,664 B2 | 8/2012 | Dudley et al. |
| 8,492,369 B2 | 7/2013 | Dudley et al. |
| 8,512,794 B2 | 8/2013 | Perlman |
| 2002/0012680 A1 | 1/2002 | Patel et al. |
| 2003/0077297 A1 | 4/2003 | Chen et al. |
| 2003/0104048 A1 | 6/2003 | Patel et al. |
| 2003/0203043 A1 | 10/2003 | Yegorova |
| 2003/0236236 A1 | 12/2003 | Chen et al. |
| 2004/0087564 A1 | 5/2004 | Wright et al. |
| 2004/0115287 A1 | 6/2004 | Chen et al. |
| 2004/0127476 A1 | 7/2004 | Kershman et al. |
| 2005/0100608 A1 | 5/2005 | Ebert |
| 2005/0101517 A1 | 5/2005 | De Nijs et al. |
| 2005/0153948 A1 | 7/2005 | Spilburg |
| 2005/0176692 A1 | 8/2005 | Amory et al. |
| 2005/0287203 A1 | 12/2005 | Nijs De et al. |
| 2006/0003002 A1 | 1/2006 | Fikstad et al. |
| 2006/0034937 A1 | 2/2006 | Patel |
| 2006/0263397 A1 | 11/2006 | Li et al. |
| 2007/0009559 A1 | 1/2007 | Li et al. |
| 2007/0022674 A1 | 2/2007 | Worthington |
| 2007/0078091 A1 | 4/2007 | Hubler et al. |
| 2007/0154533 A1 | 7/2007 | Dudley |
| 2007/0190080 A1 | 8/2007 | Friedman |
| 2007/0196440 A1 | 8/2007 | Shulman et al. |
| 2007/0254026 A1 | 11/2007 | Stewart |
| 2008/0124387 A1* | 5/2008 | Spilburg ............ A61K 9/127 424/451 |
| 2008/0200533 A1 | 8/2008 | Krishnan |
| 2008/0206161 A1 | 8/2008 | Tamarkin et al. |
| 2008/0249076 A1 | 10/2008 | Holm et al. |
| 2008/0261937 A1 | 10/2008 | Dudley et al. |
| 2008/0305177 A1 | 12/2008 | Kershman et al. |
| 2008/0317844 A1 | 12/2008 | Dudley et al. |
| 2009/0074859 A1 | 3/2009 | Patel |
| 2009/0075961 A1 | 3/2009 | Ebert |
| 2009/0077961 A1 | 3/2009 | Baker |
| 2009/0123564 A1 | 5/2009 | Jain et al. |
| 2010/0136105 A1 | 6/2010 | Chen et al. |
| 2010/0137271 A1 | 6/2010 | Chen et al. |
| 2010/0173882 A1 | 7/2010 | Giliyar et al. |
| 2011/0142945 A1 | 6/2011 | Chen et al. |
| 2011/0160168 A1 | 6/2011 | Dhingra |
| 2011/0251167 A1 | 10/2011 | Dudley et al. |
| 2011/0263552 A1 | 10/2011 | Dhingra et al. |
| 2011/0312928 A1 | 12/2011 | Nachaegari et al. |
| 2012/0135069 A1 | 5/2012 | Keck et al. |
| 2012/0135074 A1 | 5/2012 | Giliyar et al. |
| 2012/0148675 A1 | 6/2012 | Chickmath et al. |
| 2012/0244215 A1 | 9/2012 | Giliyar et al. |
| 2012/0309731 A1 | 12/2012 | Dudley et al. |
| 2012/0322780 A1 | 12/2012 | Giliyar et al. |
| 2013/0022674 A1 | 1/2013 | Dudley et al. |
| 2013/0029947 A1 | 1/2013 | Nachaegari et al. |
| 2013/0303495 A1 | 11/2013 | Dhingra et al. |
| 2014/0011780 A1 | 1/2014 | Dhingra |
| 2016/0166584 A1 | 6/2016 | Patel et al. |
| 2018/0021349 A1 | 1/2018 | Dhingra et al. |

FOREIGN PATENT DOCUMENTS

| | | | |
|---|---|---|---|
| EP | 1925294 A1 | 5/2008 | |
| EP | 2682111 A1 | 1/2014 | |
| JP | 2005-526119 A | 9/2005 | |
| JP | 2008-133281 A | 6/2008 | |
| WO | WO-95/24893 A1 | 9/1995 | |
| WO | WO-97/40823 A1 | 11/1997 | |
| WO | WO-9740823 A1 * | 11/1997 | ........... A61K 9/1075 |
| WO | WO-99/59556 A1 | 11/1999 | |
| WO | WO-03/010146 A1 | 2/2003 | |
| WO | WO-03/094891 A1 | 11/2003 | |
| WO | WO-2005/051290 A2 | 6/2005 | |
| WO | WO-2006/084312 A1 | 8/2006 | |
| WO | WO-2006/113505 A2 | 10/2006 | |
| WO | WO-2010/081032 A2 | 7/2010 | |
| WO | WO-2011/082384 A2 | 7/2011 | |
| WO | WO-2012/092202 A2 | 7/2012 | |
| WO | WO-2014/143127 A1 | 9/2014 | |

OTHER PUBLICATIONS

Grosso et al., "Fatty acid, sterol and proximate compositions of peanut species (Arachis L.) seeds from Bolivia and Argentina," Grasas y Aceites. 48(4):219-25 (1997).

Micallef et al., "The lipid-lowering effects of phytosterols and (n-3) polyunsaturated fatty acids are synergistic and complementary in hyperlipidemic men and women," J Nutr. 138(6):1086-90 (2008).

Hawley et al., "Targeting of colloids to lymph nodes: influence of lymphatic physiology of colloidal characteristics," Adv Drug Deliv Reviews. 17(1):129-48 (1995).

Trevaskis et al., "The lymph lipid precursor pool is a key determinant of intestinal lymphatic drug transport," J Pharmacol Exp Ther. 316(2):881-91 (2006).

Heinemann et al., "Effect of low-dose sitostanol on serum cholesterol in patients with hypercholesterolemia," Atherosclerosis. 61(3):219-23 (1986). Abstract only.

Lees et al., "Plant sterols as cholesterol-lowering agents: clinical trials in patients with hypercholesterolemia and studies of sterol balance," Atherosclerosis. 28(3):325-338 (1977). Abstract only.

Office Action for Canadian Patent Application No. 2,822,435, dated Sep. 6, 2016 (4 pages).

Wagner, "Drug bioavailability studies," Hosp Prac. 12:119-27 (1977).

Johnsen, "Long-term oral testosterone and liver function," Lancet. 311(8054):50 (1978).

"Saw palmetto extract," Wikipedia. <https://en.wikipedia.org/wiki/Saw_palmetto_extract>, retrieved Nov. 4, 2009.

Welling, "Effects of food on drug absorption," Pharmacol Ther. 43:425-41 (1989).

Kweia et al., "Lymphatic uptake of MK-386, a sterol 5a-reductase inhibitor, from aqueous and lipid formulations," Int J Pharm. 164(1-2):37-44 (1998).

Mattson et al., "Optimizing the effect of plant sterols on cholesterol absorption in man," Am J Clin Nutr. 35:697-700 (1982).

Right fax interview agenda concerning U.S. Appl. No. 13/012,084, dated Aug. 16, 2013 (9 pages).

Welling, "Interactions affecting drug absorption," Clin Pharmacokinet. 9:404-34 (1984).

Marks et al., "Long-term effects of finasteride on prostate tissue composition," Urology. 53(3):574-80 (1999).

Kossena et al., "Influence of the intermediate digestion phases of common formulation lipids on the absorption of a poorly water-soluble drug," J Pharm Sci. 94(3):481-92 (2005).

Daggett et al., "Oral testosterone, a reappraisal," Horm Res. 9(3):121-9 (1978).

Yin et al., "Reexamination of pharmacokinetics of oral testosterone undecanoate in hypogonadal men with a new self-emulsifying formulation," available in PMC Sep. 19, 2014, published in final edited form as: J Androl. 33(2):190-201 (2012) (19 pages).

McConnell et al., "The effect of finasteride on the risk of acute urinary retention and the need for surgical treatment among men with benign prostatic hyperplasia. Finasteride Long-Term Efficacy and Safety Study Group," N Engl J Med. 338(9):557-63 (1998).

Porter et al., "Uptake of drugs into the intestinal lymphatics after oral administration," Adv Drug Deliv Reviews. 25:71-89 (1997).

"Technical Data Sheet," CardioAid XF Plant Sterols ADM, Product Code 040551.

"SOV Therapeutics Receives U.S. Orphan Drug Designation for the Use of Oral Testosterone Undecanoate in the Treatment of Constitutional Delay in Growth and Puberty in Adolescent Boys (14-17 Years of Age)," http://biospace.com/News/sov-therapeutics-receives-u-s-orphan-drug/288181, retrieved Jul. 26, 2017 (1 page).

Miettinen et al., "Serum plant sterols and cholesterol precursors reflect cholesterol absorption and synthesis in volunteers of a randomly selected male population," Am J Epidemiol. 131(1):20-31 (1990). Abstract only.

(56) References Cited

OTHER PUBLICATIONS

Pouton, "Formulation of self-emulsifying drug delivery systems," Adv Drug Deliv Rev. 25(1):47-58 (1997).
Amory et al., "Oral testosterone in oil: pharmacokinetic effects of 5alpha reduction by finasteride or dutasteride and food intake in men," J Androl. 27(1):72-8 (2006).
Amory et al., "Oral testosterone with and without concomitant inhibition of 5alpha-reductase by dutasteride in hypogonadal men for 28 days," J Urology. 185:626-32 (2011).
Nishiyama et al., "The influence of androgen deprivation therapy on dihydrotestosterone levels in the prostatic tissue of patients with prostate cancer," Clin Cancer Res. 10:7121-6 (2004).
U.S. Appl. No. 15/959,626, filed Apr. 23, 2018 (90 pages).
Araya et al., "The novel formulation design of O/W microemulsion for improving the gastrointestinal absorption of poorly water soluble compounds," Int J Pharm. 305(1-2):61-74 (2005).
Perlman et al., "Development of a self-emulsifying formulation that reduces the food effect for torcetrapib," Int J Pharm. 351(1-2):15-22 (2008).
Roehrborn et al., "Efficacy and safety of a dual inhibitor of 5-alpha-reductase types 1 and 2 (dutasteride) in men with benign prostatic hyperplasia," Urology. 60(3):434-41 (2002).
Bollman et al., "Techniques for the collection of lymph from the liver, small intestine, or thoracic duct of the rat," J Lab Clin Med. 33(10):1349-52 (1948).
Haren et al., "Effect of 12 month oral testosterone on testosterone deficiency symptoms in symptomatic elderly males with low-normal gonadal status," Age Ageing. 34:125-30 (2005).
Abidi, "Chromatographic analysis of plant sterols in foods and vegetable oils," J Chromatogr A. 935(1-2):173-201 (2001).
Russell et al., "Steroid 5 alpha-reductase: two genes/two enzymes," Annu Rev Biochem. 63:25-61 (1994).
Bramson et al., "Unique preclinical characteristics of GG745, a potent dual inhibitor of 5AR," J Pharmacol Exp Ther. 282(3) 1496-502 (1997).
Merck Canada Inc. "Andriol Product Monograph: Part III: Consumer Information." https://pdf.hres.ca/dpd_pm/00033378.PDF (2015) (3 pages).
Bhasin et al., "Drug insight: Testosterone and selective androgen receptor modulators as anabolic therapies for chronic illness and aging," available in PMC Nov. 9, 2007, published in final edited form as: Nat Clin Pract Endrocrinol Metab. 2(3):146-59 (2006) (20 pages).
Shackleford et al., "Contribution of lymphatically transported testosterone undecanoate to the systemic exposure of testosterone after oral administration of two andriol formulations in conscious lymph duct-cannulated dogs," J Pharmacol Exp Ther. 306(3):925-33 (2003).
Coert et al., "The pharmacology and metabolism of testosterone undecanoate (TU), a new orally active androgen," Acta Endocrinol (Copenh). 79(4):789-800 (1975).
Zmuda et al., "The effect of testosterone aromatization on high-density lipoprotein cholesterol level and postheparin lipolytic activity," Metabolism. 42(4):446-50 (1993).
Charman et al., " Physicochemical and physiological mechanisms for the effects of food on drug absorption: the role of lipids and pH," J. Pharm Sci. 86(3):269-282 (1997).
Steiner, "Clinical pharmacokinetics and pharmacodynamics of finasteride," Clin Pharmacokinet. 30(1):16-27 (1996). Abstract Only.
Office Action for Japanese Patent Application No. 2012-547323, dated Sep. 17, 2015 (5 pages).
Nieschlag et al., "Influence of sex, testicular development and liver function on the bioavailability of oral testosterone," Eur J Clin Invest. 7:145-7 (1977).
Traish et al., "Adverse side effects of 5alpha-reductase inhibitors therapy: persistent diminished libido and erectile dysfunction and depression in a subset of patients," J Sex Med. 8(3):872-84 (2011).
Fogh et al., "Serum-testosterone during oral administration of testosterone in hypogonadal men and transsexual women," Acta Endocrinol (Copenh). 87(3):643-9 (1978).
Debruyne et al., "Efficacy and safety of long-term treatment with the dual 5 alpha-reductase inhibitor dutasteride in men with symptomatic benign prostatic hyperplasia," Eur Urol. 46:488-95 (2004).
Porter et al., "Intestinal lymphatic drug transport: an update," Adv Drug Deliv Reviews. 50:61-80 (2001).
Trevaskis et al., "Bile increases intestinal lymphatic drug transport in the fasted rat," Pharm Res. 22(11):1863-70 (2005).
Schnabel et al., "The effect of food composition on serum testosterone levels after oral administration of Andriol Testocaps," Clin Endocrinol (Oxf.). 66:579-85 (2007).
Borst et al., "Inhibition of 5alpha-reductase blocks prostate effects of testosterone without blocking anabolic effects," Am J Physiol Endocrinol Metab. 288:E222-7 (2005).
Trevaskis et al., "The role of the intestinal lymphatics in the absorption of two highly lipophilic cholesterol ester transfer protein inhibitors (CP524,515 and CP532,623)," Pharm Res. 27(5):878-93 (2010).
Houwing et al., "Pharmacokinetic study in women of three different doses of a new formulation of oral testosterone undecanoate, Andriol Testocaps," Pharmacotherapy. 23(10):1257-65 (2003).
Andriole et al., "Effect of dutasteride on the risk of prostate cancer," NE J Med. 362(13):1192-202 (2010).
Page et al., "Persistent intraprostatic androgen concentrations after medical castration in healthy men," J Clin Endocrinol Metab. 91(10):3850-6 (2006).
Walsh, "Chemoprevention of prostate cancer," N Engl J Med. 362(13):1237-8 (2010).
Office Action for U.S. Appl. No. 13/936,036, dated Sep. 6, 2016 (22 pages).
Office Action for U.S. Appl. No. 13/936,036, dated Jul. 30, 2015 (11 pages).
Welling, "How food and fluid affect drug absorption: results of initial studies," Postgrad Med. 62(1):73-75, 78-82 (1977).
Office Action for U.S. Appl. No. 13/936,036, dated Jun. 5, 2014 (10 pages).
Johnsen et al., "Therapeutic effectiveness of oral testosterone," Lancet. 2:1473-5 (1974).
Office Action for U.S. Appl. No. 13/936,036, dated Dec. 5, 2014 (13 pages).
Whitten et al., "Select patients with hypogonadotropic hypogonadism may respond to treatment with clomiphene citrate," Fertil Steril 86(6):1664-8 (2006).
Office Action for U.S. Appl. No. 12/983,216, dated Apr. 27, 2016 (25 pages).
Porter et al., "Lipids and lipid-based formulations: optimizing the oral delivery of lipophilic drugs," Nat Rev Drug Discov. 6(3):231-48 (2007).
Office Action for U.S. Appl. No. 12/983,216, dated Jun. 7, 2012 (12 pages).
Food and Drug Administration, "Federal Register" 75(235):76526-71 (2010).
Office Action for U.S. Appl. No. 12/983,216, dated Jul. 29, 2013 (37 pages).
Kossena et al., "Probing drug solubilization patterns in the gastrointestinal tract after administration of lipid-based delivery systems: a phase diagram approach," J Pharm Sci. 93(2):332-48 (2004).
Office Action for U.S. Appl. No. 12/983,216, dated Aug. 1, 2012 (14 pages).
Extended European Search Report for European Patent Application No. 13877592.9, dated Sep. 8, 2016 (6 pages).
Office Action for U.S. Appl. No. 12/983,216, dated Sep. 2, 2015 (22 pages).
Advertisement for Eli Lilly and Company, "Cytellin sitosterols: the cholesterol-lowering agent with an unparalleled record of safety," Bull NY Acad Med. 39(8) (1963).
Office Action for U.S. Appl. No. 12/983,216, dated Mar. 7, 2014 (43 pages).
Gursoy et al. "Self-emulsifying drug delivery systems (SEDDS) for improved oral delivery of lipophilic drugs," Biomed Pharmacother. 58(3):173-82 (2004).
Office Action for U.S. Appl. No. 12/983,216, dated Jan. 22, 2015 (31 pages).

(56) References Cited

OTHER PUBLICATIONS

Office Action for Japanese Patent Application No. 2013-124891, dated Dec. 12, 2014 (9 pages).
Office Action for Japanese Patent Application No. 2012-547323, dated Nov. 18, 2014 (8 pages).
Communication pursuant to Article 94(3) EPC and Form 2906 for European Patent Application No. 13877592.9, dated Jun. 16, 2017 (5 pages).
First Office Action for Chinese Patent Application No. 201380074669.9, dated Mar. 22, 2017 (23 pages).
Reininger et al., "Effect of digestion on distribution of blood flow in the rat," Science. 126(3284):1176 (1957).
Horst et al., "Lymphatic absorption and metabolism of orally administered testosterone undecanoate in man," Klin Wochenschr. 54:875-9 (1976).
Roth et al., "Steady-state pharmacokinetics of oral testosterone undecanoate with concomitant inhibition of 5alpha-reductase by finasteride," Int J Androl. 34(6:1):541-7 (2011).
Nieschlag et al., "Plasma androgen levels in men after oral administration of testosterone or testosterone undecanoate," Acta Endocrinol (Copenh). 79:366-74 (1975).
Sikorska et al., "Derivatised alpha-tocopherol as a CoQ10 carrier in a novel water-soluble formulation," BioFactors. 18:173-83 (2003).
First Examination Report for New Zealand Patent Application No. 631833, dated Nov. 6, 2015 (2 pages).
Page et al., "Dihydrotestosterone administration does not increase intraprostatic androgen concentrations or alter prostate androgen action in healthy men: a randomized-controlled trial," J Clin Endocrinol Metab. 96(2):430-7 (2011).
BASF, "DL-alpha-Tocopherol: Technical information human nutrition." (2009, 2 pages).
Amory et al., "Oral testosterone in oil plus dutasteride in men: a pharmacokinetic study," J Clin Endocrinol Metab. 90(5):2610-7 (2005).
Kaukonen et al., "Drug solubilization behavior during in vitro digestion of simple triglyceride lipid solution formulations," Pharm Res. 21(2):245-53 (2004).
Connors et al., "Using a Portfolio of Particle Growth Technologies to Enable Delivery of Drugs with Poor Water Solubility," Drug Deliv Tech. 4(8):1-11 (2004).
Extended European Search Report for European Patent Application No. 10841783.3, dated Jun. 7, 2013 (8 pages).
Itoh et al., "Sterol composition of 19 vegetable oils," J Am Oil Chem Soc. 50:122-5 (1973).
Search Report for Taiwanese Patent Application No. 103109505, completed Aug. 7, 2017 (1 page).
Miettinen et al., "Reduction of serum cholesterol with sitostanol-ester margarine in a mildly hypercholesterolemic population," N Engl J Med. 333(20)1308-12 (1995).
Borowy-Borowski et al., "Unique technology for solubilization and delivery of highly lipophilic bioactive molecules," J Drug Target. 12(7):415-24 (2004).
Bagchus et al., "Important effect of food on the bioavailability of oral testosterone undecanoate," Pharmacotherapy. 23(3):319-25 (2003).
Lea et al., "Safety evaluation of phytosterol-esters. Part 9: Results of a European post-launch monitoring programme," Food and Chem Toxicol. 44:1213-22 (2006).
Pouton, "Formulation of poorly water-soluble drugs for oral administration: physicochemical and physiological issues and the lipid formulation classification system," Eur J Pharm Sci. 29(3-4):278-87 (2006).
Carey et al., "The characteristics of mixed micellar solutions with particular reference to bile," Am J Med. 49(5):590-608 (1970). Abstract only.
Shah et al., "Self-emulsifying drug delivery systems (SEDDS) with polyglycolyzed glycerides for improving in vitro dissolution and oral absorption of lipophilic drugs," Int J Pharm. 106:15-23 (1994).
International Search Report and Written Opinion for International Patent Application No. PCT/US2013/049405, dated Dec. 12, 2013 (15 pages).
Phillips et al., "Free and Esterified Sterol Composition of Edible Oils and Fats," J Food Composition and Analysis. 15:123-42 (2002).
Carlin et al., "Disposition and pharmacokinetics of [14C]finasteride after oral administration in humans," Drug Metab Dispos. 20(2):148-55 (1992).
Giliyar et al., "Challenges & Opportunities in Oral Delivery of Poorly Water-Soluble Drugs," Drug Deliv Tech. 6(1):57-63 (2006).
Matsumoto, "Hormonal therapy of male hypogonadism," Endocrinol Metab Clin North Am. 23(4):857-75 (1994).
Pedersen et al., "A comparison of the solubility of danazol in human and simulated gastrointestinal fluids," Pharm Res. 17(7):891-4 (2000).
Office Action for European Patent Application No. 10841783.3, dated Nov. 26, 2015 (5 pages).
Armand et al., "Digestion and absorption of 2 fat emulsions with different droplet sizes in the human digestive tract," Am J Clin Nutr. 70(6):1096-106 (1999).
Office Action for U.S. Appl. No. 13/174,756, dated Oct. 2, 2013 (19 pages).
Bergström et al., "Studies of intestinal digestion and absorption in the human," J Clin Invest. 36(10):1521-36 (1957).
Corona et al., "Update in testosterone therapy for men," J Sex Med. 8(3):639-54 (2011).
Delaney et al., "Oral absorption of phytosterols and emulsified phytosterols by Sprague-Dawley rats," J Nutr Biochem. 15(5):289-95 (2004).
Melander, "Influence of food and different nutrients on drug bioavailability," World Rev Nutr Diet. 43:34-44 (1984).
MacGregor et al., "Influence of lipolysis on drug absorption from the gastro-intestinal tract," Adv Drug Deliv Rev. 25(1):33-46 (1997).
Mazer et al., "Enhanced transdermal delivery of testosterone: a new physiological approach for androgen replacement in hypogonadal men," J Control Release. 19:347-62 (1992).
Mostaghel et al., "Intraprostatic androgens and androgen-regulated gene expression persist after testosterone suppression: therapeutic implications for castration-resistant prostate cancer," Cancer Res. 67(10):5033-41 (2007).
Office Action for U.S. Appl. No. 13/936,036, dated Feb. 17, 2016 (13 pages).
Tilvis et al., "Serum plant sterols and their relation to cholesterol absorption," Am J Clin Nutr. 43:92-7 (1986).
Eldridge et al., "Controlled vaccine release in the gut-associated lymphoid tissues. I. Orally administered biodegradable microspheres target the peyer's patches," J Control Release. 11(1-3):205-14 (1990). Abstract only.
Kincl et al., "Increasing intestinal absorption of drugs by formulation," Arch Pharm (Weinheim). 319(7):615-24 (1986).
Extended European Search Report for European Patent Application No. 13170663.2, dated Dec. 10, 2013 (8 pages).
Trevaskis et al., "Lipid-based delivery systems and intestinal lymphatic drug transport," Adv Drug Deliv Rev. 60:702-716 (2008).
Briefing Document for Bone, Reproductive, and Urologic Drugs Advisory Committee, "Oral Testosterone Undecanoate Capsules (Jatenzo™) for Testosterone Replacement Therapy in Hypogonadal Men," Clarus Therapeutics, Inc., dated Jan. 9, 2018 (116 pages).
Compound Summary for CID 14985: Vitamin E, https://pubchem.ncbi.nlm.nih.gov/compound/alpha-Tocopherol, retrieved May 22, 2018 (106 pages).
First Examination Report for Indian Patent Application No. 1959/KOLNP/2012, dated May 31, 2018 (7 pages).
Kovarik et al., "Reduced inter- and intraindividual variability in cyclosporine pharmacokinetics from a microemulsion formulation," J Pharm Sci. 83(3):444-6 (1994).
Mueller et al., "Influence of a fat-rich meal on the pharmacokinetics of a new oral formulation of cyclosporine in a crossover comparison with the market formulation," Pharm Res. 11(1):151-5 (1994).
Office Action for Chinese Patent Application No. 201380074669.9 and English Translation dated Jan. 19, 2018 (17 pages).
Sheen et al., "Bioavailability of a poorly water-soluble drug from tablet and solid dispersion in humans," J Pharm Sci. 80(7):712-4 (1991).

(56) References Cited

OTHER PUBLICATIONS

Von Eckardstein et al., "Treatment of male hypogonadism with testosterone undecanoate injected at extended intervals of 12 weeks: a phase II study," J Androl. 23(3):419-25 (2002).

Office Action Summary and Notice of References Cited for U.S. Appl. No. 13/936,036, dated Jun. 18, 2018 (21 pages).

Decision to refuse a European Patent application for European Patent Application No. 13170663.2, dated May 7, 2018 (10 pages).

Täuber et al., "Absolute bioavailability of testosterone after oral administration of testosterone-undecanoate and testosterone," Eur J Drug Metab Pharmacokinet. 11(2):145-9 (1986).

Diver et al., "Diurnal rhythms of serum total, free and bioavailable testosterone and of SHBG in middle-aged men compared with those in young men," Clin Endocrinol. 58(6):710-7 (2003).

Chen et al., "Blockade of Androgen Markers Using a Novel Betasitosterol, Thioctic Acid and Carnitine-containing Compound in Prostate and Hair Follicle Cell-based Assays," Phytother. Res. 30:1016-20 (2016).

Vahouny et al., "Comparative lymphatic absorption of sitosterol, stigmasterol, and fucosterol and differential inhibition of cholesterol absorption," Amer. J. Clin. Nutr. 37:805-9 (1983).

Brown et al., "Plant sterol and stanol substrate specificity of pancreatic cholesterol esterase," J. Nutr. Bioch. 21(8):736-40 (2010).

Awad et al., "Phytosterol feeding induces alteration in testosterone metabolism in rat tissues," J. Nutr. Biochem. 9:712-7 (1998).

Prager et al., "A Randomized, Double-Blind, Placebo-Controlled Trial to Determine the Effectiveness of Botanically Derived Inhibitors of 5-α-Reductase in the Treatment of Androgenetic Alopecia," J. Altern. Complem. Med. 8(2):143-52 (2002).

Cabeza et al., "Effects of β-sitosterol as Inhibitor of 5α-reductase in Hamster Prostate," Proc. West Pharmacol. Soc. 46:153-5 (2003).

Technical Data Sheet for CardioAid XF—Plant Sterols—040551, Archer Daniels Midland Company, Apr. 10, 2019 (1 page).

Archer Daniels Midland Company, "CardioAid-XF Plant Sterols: Technical Data Sheet," <https://web.archive.org/web/20101223125036/http://www.adm.com/en-US/products/Documents/ADM-CardioAid-XF.pdf>, published Dec. 23, 2010 (3 pages).

\* cited by examiner

Dissolution (USP 2 apparatus) of testosterone undecanoate formulations

▲: Formulation described by Capsule 4 of Example 1 US2010/0173882

■: Formulation described by Capsule 2 of Example 1 of US2010/0173882

♦: Formulation 55 of Table 20

X: Formulation 51 of Table 20

✶: Formulation 53 of Table 20

●: Formulation 9 of Table 2

Dissolution (USP 2 apparatus) of testosterone undecanoate formulations (80mg TU)

▲: Formulation 28 of Table 10

●: Formulation 39 of Table 14

+: Formulation 56 of Table 27

✶: Formulation 57 of Table 27

X: Formulation 58 of Table 21

◆: Formulation 17 of Table 5

Dissolution (USP 2 apparatus) of testosterone undecanoate formulations

♦: Formulation 59 of Table 22

■: Formulation 60 of Table 22

▲: Formulation 61 of Table 22

Mean testosterone undecanoate pharmacokinetic profiles in beagle dogs of treatments A-F of Table 23, Example 4.

Mean testosterone pharmacokinetic profiles in beagle dogs of treatments A-F of Table 23, Example 4.

Mean testosterone pharmacokinetic profile in beagle dogs of Formulation 54 (▲) and Formulation 52 (■) of Table 20 and Example 5.

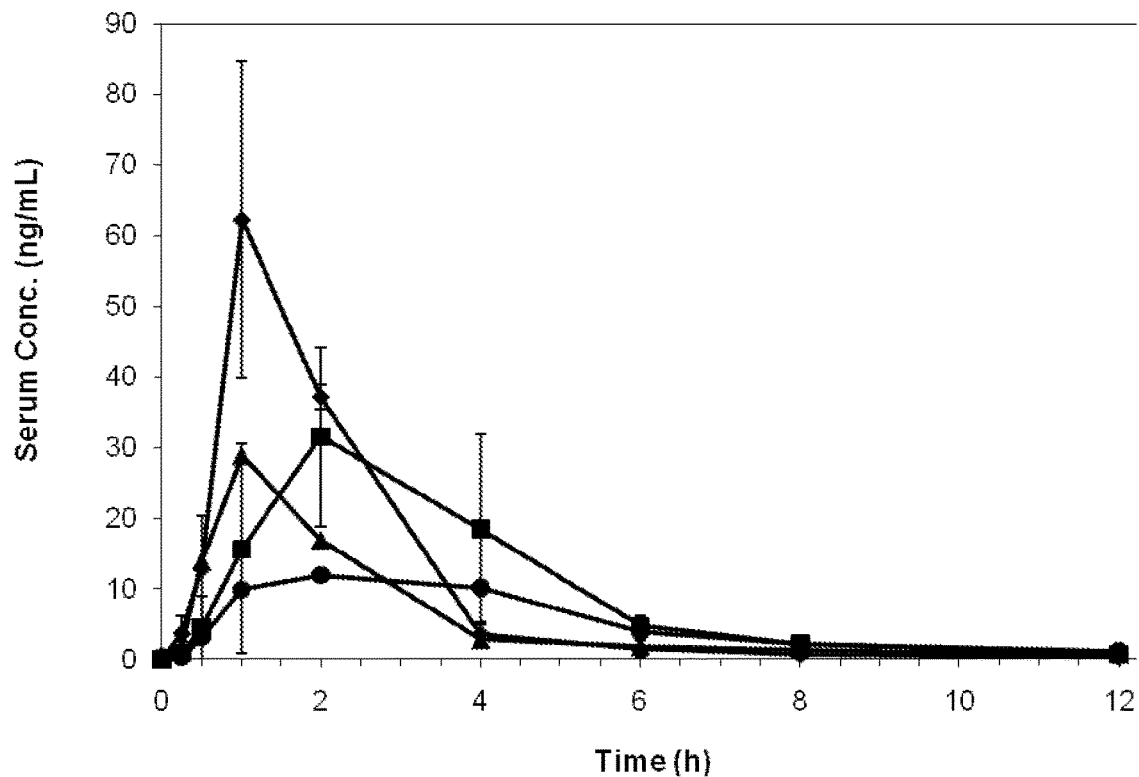

Mean testosterone and dihydrotestosterone pharmacokinetic profile in beagle dogs of Formulation 52 with and without finasteride.

♦ Testosterone concentrations, Formulation 52 (80mg TU) dosed without finasteride ▲ Testosterone concentrations, Formulation 52 (80mg TU) dosed with finasteride ■ Dihydrotestosterone concentrations, Formulation 52 (80mg TU) dosed without finasteride ● Dihydrotestosterone concentrations, Formulation 52 (80mg TU) dosed without finasteride

FIG. 7

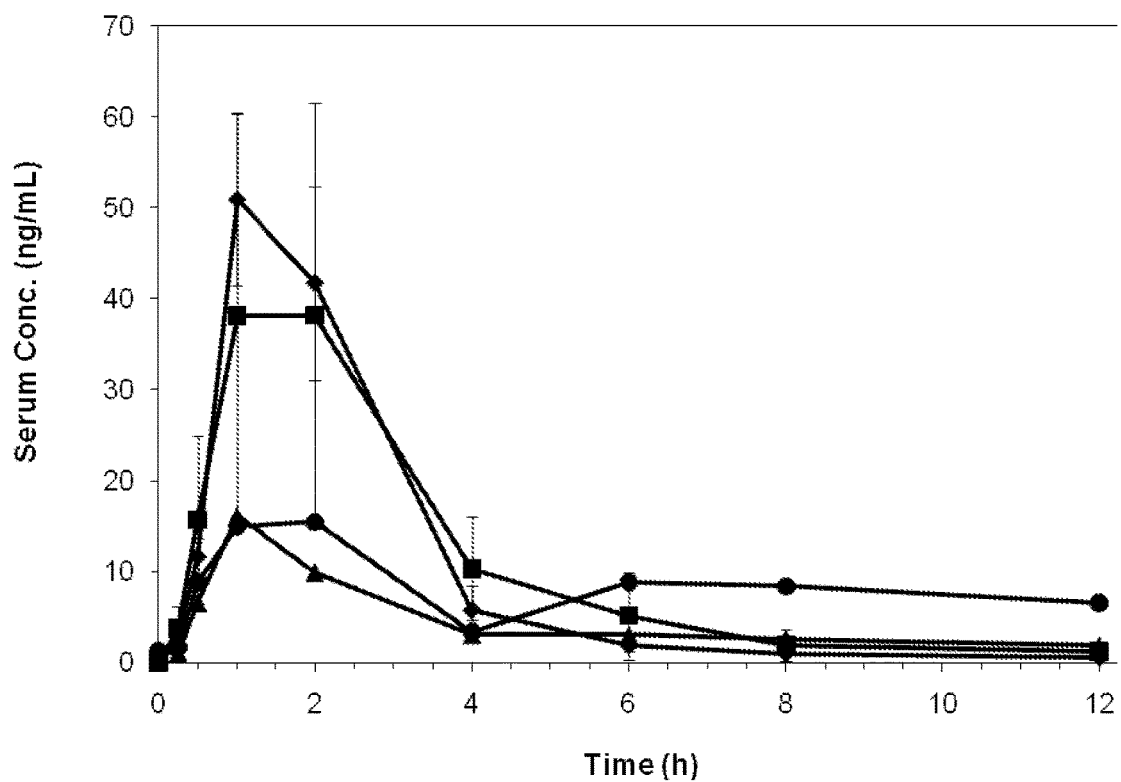

Mean teststosterone and dihydrotestosterone pharmacokinetic profile in beagle dogs of Formulation 52 with and without dutasteride.

♦ Testosterone concentrations, Formulation 52 (80mg TU) dosed without dutasteride ■ Testosterone concentrations, Formulation 52 (80mg TU) dosed with dutasteride ▲ Dihydrotestosterone concentrations, Formulation 52 (80mg TU) dosed without dutasteride ● Dihydrotestosterone concentrations, Formulation 52 (80mg TU) dosed without dutasteride

FIG. 8

Mean testosterone pharmacokinetic profile in beagle dogs of Formulation 52 with 400mg (▲ and ■) and 800mg (♦) of phytosterols.

Mean testosterone (dark bar) and dihydrotestosterone (light bar) exposures resulting from Treatments G through L, Table 24, Example 5. Error bars represent plus and minus one standard deviation.

Ratio of dihydrotestosterone to testosterone in four beagle dogs dosed with treatments as described in Example 5.

First bar: Treatment K, Table 24

Second bar: Treatment I, Table 24

Third bar: Treatment J, Table 24

Predicted human values of testosterone (first bar) and dihydrotestosterone (second bar) based on Treatments I, L, and K from Example 5, for 80mg testosterone undecanoate single dose

MODULATION OF SOLUBILITY, STABILITY, ABSORPTION, METABOLISM, AND PHARMACOKINETIC PROFILE OF LIPOPHILIC DRUGS BY STEROLS

CROSS REFERENCE TO RELATED APPLICATIONS

This application is a continuation of U.S. patent application Ser. No. 12/983,216, filed Dec. 31, 2010, which application claims the benefit of priority of U.S. Provisional Patent Application No. 61/291,769, titled "MODULATION OF SOLUBILITY, STABILITY, ABSORPTION, METABOLISM, AND PHARMACOKINETIC PROFILE OF LIPOPHILIC DRUGS BY STEROLS" and filed on Dec. 31, 2009. The disclosure of the foregoing applications are hereby incorporated herein by reference in their entirety, for all purposes.

FIELD OF THE INVENTION

The present invention relates to formulations for administration of a therapeutic agent, where the formulation contains one or more therapeutic agents, administered with a sterol and, optionally, a solubilizer and an enhancer, where the formulations provide modulation to one or more of: solubility, stability, absorption, metabolism, and pharmacokinetic profile of the therapeutic agent when administered to a subject. The invention also relates to methods of making and methods of using the formulations.

DESCRIPTION OF THE RELATED ART

Drug absorption is the process by which a drug is transported from its site of administration into the blood, via portal or lymphatic system. Oral drug delivery, as one type of delivery, is advantageous in that it provides easy administration, can be performed by the patient or another, is not painful to the patient and involves relatively low effort. Absorption of a drug administered orally occurs along the entire gastrointestinal (GI) tract, although most drug absorption occurs in the lower GI tract. Such absorption can occur via either of the portal and mesenteric lymphatic routes.

The portal route involves transport of the drug through the portal vein, to the liver. Many drugs are metabolized in the liver. This may result in a lowered systemic bioavailability of the drug as the drug is metabolized. This lowering of bioavailability is referred to as the "first pass effect." In other words, the greater the first pass effect, the smaller the amount of the drug that will reach the systemic circulation. This results in increased doses of the drug taken orally to achieve desired levels for efficacy. Metabolism of a drug may also occur in the GI tract and contributes to the reduced or variable absorption of such a drug.

The lymphatic system is an extensive drainage network spread throughout the body. It shadows the blood circulation system and its functions include the transport of fluid components of blood which have passed into the interstitial space from the capillaries of the circulation system. The intestinal lymphatics also play an essential role in absorption of products from lipid digestion, e.g., long chain fatty acids and lipid soluble vitamins. If the lymphatic route can be optimized or selected for drug absorption and absorption via the portal route reduced, then the first pass effect can correspondingly be reduced or bypassed, improving bioavailability of the drug. The drugs are also metabolized in the GI tract by enzymes present in the brush-border layer or secreted into the GI tract. The amount of the drug available for absorption is thus impacted by the susceptibility of the drug to these metabolizing enzymes. The access of the enzymes to the drug can be modulated by using excipients which preferentially shield the drug. The inventor has discovered that sterols minimize the chemical and enzymatic degradation of the drugs in the GI tract and hence increase the amount of drug available for absorption. This leads to lower doses of lipophilic drugs and modulating the side effect profile of the effective dose.

Poor water solubility is a significant obstacle for drug absorption. Approximately 40% of drugs worldwide are insoluble in water and therefore, are difficult to formulate. Since 1995, 90% of drugs released into the market have limited solubility and/or poor permeability (Conners, R. D., and Elder, E. J., *Drug Deliv. Tech.* 2004, vol. 4, no. 8, pp. 1-11; Giliyar, C., et al., *Drug Deliv. Tech.* 2006, vol. 6, no. 1, pp. 57-63.). Improving solubility will benefit patients and consumers by rendering previously poorly absorbed compounds more bioavailable and hence more effective for a given dose. First, poor water solubility can limit the type of formulation available to a bioactive compound. Poorly soluble drugs may have to be dissolved in oils so that they can be incorporated into a capsule. Second, poorly soluble compounds are likely to have limited bioavailability because once in the body, they do not remain in solution at the site of action. This results in lower absorption and reduced efficacy. To counter this, administration of higher doses is often necessary. However, higher doses can potentially lead to increased side effects.

The science of drug administration therefore requires consideration of a number of factors in evaluating the absorption of a drug, such as type and route of transport, the drug's properties including its susceptibility to degradation/metabolism, the formulation by which the drug is administered, concentration and amounts of drug, poor water solubility and any inhibitory factors.

Administration via the intestinal lymphatic system provides advantages such as avoidance of hepatic first pass metabolism, and the potential to target specific diseases states known to spread via the lymphatic system, for example certain cancers and HIV.

Various studies have been conducted regarding optimization of administration, absorption and bioavailability of drugs.

Most formulation approaches to improve bioavailability of water insoluble, highly lipophilic drugs are based on either particle size reduction technologies (e.g. micronization, nano-particle generation) to increase drug dissolution rate and/or achieve transient solubilization, or technologies to achieve a sustained solubilization of the drug, such as complexation, or use of lipid-based delivery systems.

The particle size reduction technologies often fail to overcome bioavailability limitations and result in a large food effect, i.e., much higher exposure in a fed state than in a fasted state, which can lead to greater sensitivity of the pharmacokinetic profile to the fat content of meals and the timing of food administration. These conventional dissolution enhancement and transient solubilization technologies do not improve the transport across the unstirred water (or boundary) layer (UWL), which separates the bulk fluid phase of the small intestine lumen from the brush border membrane of enterocytes. For many poorly soluble drugs, this transport across the UWL represents the dominant rate-limiting step for drug absorption.

A widely utilized approach to achieve sustained solubilization and overcome poor fasted state bioavailability of lipophilic drugs is to utilize solutions in lipid vehicles containing surfactants that constitute a self-emulsifying drug delivery system (SEDDS), to effect spontaneous emulsification upon contact of the lipid with fluids in the GI tract. If microemulsions are formed, these are referred to as self-microemulsifying drug delivery systems (SMEDDS). SEDDS produce opaque, white emulsions with lipid droplet sizes of approximately 100 nm, while SMEDDS form transparent microemulsions with droplet size of less than 50 nm (Gursoy et al., Biomed Pharmacother 2004: 58(3): 173-182).

SEDDS and SMEDDS form micelles upon dilution and are well suited for providing the sustained solubilization in vivo and rapid transport across the UWL. The advantages of SEDDS/SMEDDS include fast absorption, lower effective dose, less variable absorption, and minimal or absence of food effects. For example, compared to the crude emulsion (Sandimmune®), a SMEDDS formulation of CyclosporinA (Neoral®) was shown to enhance fasted state bioavailability, decrease the food effect, increase dose linearity and reduce variability in exposures (Perlman et al., Int J Pharm, 15-22, 2008).

The primary mechanism by which lipid-based drug formulations enhance drug solubilization within the GI tract are by presentation as a solubilized formulation (thereby avoiding solid-state limitations) and by induced changes to the character of the GI environment such that solute-solvent interactions and drug solubility are enhanced.

The presence of food within the GI tract was historically regarded as a barrier to absorption, leading to suggestions that drugs should be taken up on an empty stomach. However, it is currently accepted that the interaction between food and drugs should be examined on an individual basis. The character and the magnitude of the effect of food on bioavailability is a function of the drug, the dose, the nature of the formulation, the size and composition of the food, and the temporal relationship between food ingestion and drug administration. (Wagner, J. G. *Hosp. Practice* 1977, 12, 119-27; Welling, P. G., *Postgrad. Med.* 1977, 62, 73-82; Melander, A., *Wld. Rev. Nutr. Diet.* 1984, 43, 34-44; Welling, P. G., *Clin. Pharmacokinet.* 1984, 9, 404-434; Welling, P. G., *Pharmacol Ther.* 1989, 43, 425-44.). The altered postprandial absorption is generally a function of the changes associated with conversion from the fasted to fed state. Changes due to (i) secretion of gastric acid and bile and pancreatic fluids, (ii) modification of gastric and intestinal motility patterns, and (iii) alterations in visceral blood and lymph flow have the most significant impact on absorption. Additionally, the composition and amount of the food ingested may have an effect on the absorption of a drug, for instance a meal containing significant lipid content may solubilize a drug to a greater extent than in the fasted state, thus increasing absorption. Review of the literature by William N. Charman et. al., demonstrates that there is often a physicochemical basis to altered bioavailability when drugs are administered postprandially (William N. Charman et. al., *J. Pharm Sci.* 1997, 86, 269-82; Porter, C. J. H., et. al., *Nat. Rev. Drug Discov.*, 2007, 6, 231-248). Charman et. al. proposed that drug candidates for lymphatic transport should have log P>5 and in addition, a triglyceride solubility>50 mg/mL. The importance of lipid solubility was illustrated by a comparison of the lymphatic transport of DDT (log P 6.19) with hexachlorobenzene (HCB) (log P 6.53). While both compounds have similar log P values, the difference in lymphatic transport on administration in oleic acid, 33.5% of the dose in case of DDT and 2.3% with HCB, was attributed to the 13 fold difference in lipid solubility. A recent publication presented data which refutes the earlier established requirement of >50 mg/ml triglyceride solubility for enhanced lymphatic absorption (Natalie L. Trevaskis et. al., *Pharm Res.* 2010, 27, 878-893).

Drugs which show a strong food effect usually show highly variable inter- and/or intra-subject bioavailability. As a result, active patient compliance is required to ensure proper drug administration.

Testosterone is one of the most important androgens synthesized in the body. It is formed mainly in the testicles and in small amounts in the adrenal glands and in women in the ovaries. In males, testosterone is responsible for the development of the male characteristics during fetal, neonatal and pubertal maturation and finally for attaining the male phenotype and for androgen-dependent functions (for example spermatogenesis). Testosterone exerts protein-anabolic action (in muscles, bones, hematopoiesis, kidneys and liver) (E. Mutschler, "Arzneimittelwirkungen" [Drug Actions], 6th edition, pp. 334-337, Wissenschaftliche Verlagsgesellschaft mbh [publisher], Stuttgart, 1991.).

Testosterone products currently on the market utilize oral, parenteral, intramuscular, transdermal, sublingual, and/or buccal routes of administration. Testosterone is rapidly metabolized by the liver. Oral, and transdermal administration is particularly challenging because testosterone is metabolized by 5-alpha reductase enzyme in the skin or GI brush-border layer to dihydrotestosterone resulting in supraphysiological levels of DHT. The plasma half-life of testosterone is short, i.e., about 10 to 30 minutes. (Auterhoff, H., et al., "Lehrbuch der Pharmazeutischen Chemie" [Textbook of Pharmaceutical Chemistry], 12th ed., pp. 570-573, Wissenschaftliche Verlagsgesellschaft mbh [publisher], Stuttgart, 1991.) Testosterone is rapidly metabolized by the liver to DHT and other metabolites. To achieve a physiological serum level, oral administration of 400 mg of testosterone is needed (S. G. Johnson, et al., Therapeutic effectiveness of oral testosterone, Lancet 2:1974, 1473-1475).

To prolong the action of testosterone, testosterone esters with varying chain length (testosterone propionate, testosterone enanthate, testosterone undecanoate, etc.) have been developed for intramuscular injection as an oily solution or suspension. It is known that in contact with body fluids these esters will slowly hydrolyze under the action of esterases thus releasing the pharmacologically active testosterone. The influence of the type of ester on the growth of the capon comb after i.m. injection has already been described (Meier, R. and Tschopp, E., Arch. Exptl. Pathol. Pharmacol. 226: 1955, 532).

One testosterone undecanoate dosage form presently in clinical development in the United States is commercially known as Aveed® (Nebido® outside of the United States) and contains 250 mg/mL of testosterone undecanoate in castor oil. Administrations of 2, 3 or 4 mL of the formulation (500, 750, 1000 mg TU) by i.m. injection demonstrated irritation at the site of injection, pulmonary oil embolism and/or injection anaphylactic reactions. Overseas the formulation (1000 mg TU in 4 mL; other ingredients: castor oil and benzyl benzoate) has been approved for use in various countries and the recommended administration regimen is 1000 mg initial administration, an optional second 1000 mg dose as soon as 6 weeks, then 1000 mg every subsequent 10-14 weeks.

Oral preparations of androgens are rare. U.S. Patent Application No. 2008/0317844 describes a SEDDS formulation of testosterone palmitate (TP). TP, once absorbed, is slowly hydrolyzed prolonging the circulation of TP and, consequently, T. SEDDS formulations comprising TP have a T half-life of about 8-9 hours. By comparison, the half-life of T is about 10-30 minutes and that of TU is about 1.5 hours. U.S. Patent Application No. 2010/0173882 describes delayed release formulations of testosterone undecanoate (TU) which reduce the $C_{max}$ by 5-15% relative to the $C_{max}$ of an immediate release formulation of Andriol® Testocaps® at the same dose (U.S. Pat. No. 7,138,389; U.S. Patent Application Publication No. 2009/0075961; U.S. Patent Application Publication No. 2008/0305177).

U.S. Patent Application Publication No. 2005/0287203 describes a Castor oil formulation of testosterone undecanoate in a pharmaceutically acceptable liquid carrier, characterized in that the liquid carrier comprises at least 50% by weight of Castor oil. The formulation also contains a lipophilic surfactant such as Lauroglycol™ 35%. The final formulation contains 53% w/w of Castor oil, 35% Lauroglycol™, and 12% testosterone undecanoate. This formulation is currently marketed in Europe and more than 86 other countries as Andriol® Testocaps®. An earlier formulation containing testosterone undecanoate in oleic acid is marketed under various trade names in different countries, e.g. Andriol® or Restandol®. Andriol®, Restandol® or Andriol® Testocaps® is provided as a soft-gelatin capsule formulation containing 40 mg of TU.

To achieve and maintain acceptable testosterone levels in the blood, 3-4 such capsules (Andriol® Testocaps®) should be administered daily. A regimen involving such a large number of separate administrations is not very suitable for the practical use of TU as an acceptable hormone replacement therapy (HRT) product, and even less practical for the use of male contraception. So many separate administrations of the drug give rise to varying serum levels and gastrointestinal side effects. These effects can make long-term replacement therapy difficult (A. M. Matsumoto: Hormonal therapy of male hypogonadism, Endocrinol. Metab. Clin. North Am. 23:1994, 857-875).

Other routes of androgen administration (parenteral, intramuscular, transdermal, nasal, sublingual, buccal, subcutaneous) have been studied by various research groups (for example, by N. A. Mazer, W. E. Heiber, J. F. Moellmer, A. W. Meikle, J. D. Stringham, S. W. Sanders, K. G. Tolman and W. D. Odell, Enhanced transdermal delivery of testosterone: A new physiological approach for androgen replacement in hypogonadal men, *J. Controll. Rel.* 19:1992, 347-362).

Drawbacks of the aforementioned therapies are as follows: 1) the therapies can have a too short effect on the systemic testosterone level, with a rapid decrease in the level shortly after an increase resulting from an oral administration; 2) the therapies' lack of individual time control of the testosterone action (in the case of i.m. injection of testosterone esters) due to the inability to change the constantly set testosterone level over a long period of time (days to weeks to months); 3) the presence of a significant food effect upon oral administration; 4) the elevation of DHT levels above physiological normal levels due to the metabolism of testosterone and its esters in organs with high 5-α-reductase activity and 5) where the therapies are in gel form, they may be hazardous to children or others, e.g., where a third party comes in contact with the skin after topical administration. The FDA has recently issued a black box warning for all testosterone dermal gel products.

In consequence, the art continues to seek improvements in methods of drug delivery that achieve modulation of solubility, stability, absorption, metabolism, and/or pharmacokinetic profile of therapeutic agents administered to a subject. In particular, improved formulations for oral and parenteral androgen administration are highly desirable.

SUMMARY OF THE INVENTION

The present invention relates to a formulation that achieves modulation of solubility, stability, absorption, metabolism, and/or pharmacokinetic profile of a therapeutic agent when administered to a subject, the formulation comprising: at least one lipophilic, poorly water soluble therapeutic agent and a phytosterol or phytosterol ester. Optionally, the formulation further comprises a solubilizing agent effective for solubilization of the therapeutic agent and/or an agent for enhancement of the biological absorption and/or metabolic stability of the therapeutic agent. In one aspect, the invention relates to a pharmaceutical composition containing such a formulation for oral, parenteral, intramuscular, transdermal, nasal, sublingual, buccal or subcutaneous administration.

In another aspect the invention relates to a method of enhancing solubility of one or more poorly soluble therapeutic agent, comprising combining: a) a phytosterol or phytosterol ester; b) a non-sterol solubilizing agent; and c) at least one lipophilic, poorly water soluble therapeutic agents, in a composition, wherein the composition is effective to enhance solubility of at least one therapeutic agent, as compared to the solubility of the same therapeutic agent in the absence of a) a phytosterol or phytosterol ester and b) a non-sterol solubilizing agent. Optionally, the composition may further comprise an enhancing agent for enhancement of the biological absorption and/or metabolic stability of the therapeutic agent.

In a still further aspect, the invention provides a method of enhancing biological absorption or metabolic stability of one or more poorly soluble therapeutic agents, the method comprising administering: a) a phytosterol or phytosterol ester; b) a non-sterol solubilizing agent; c) an enhancing agent; and d) at least one lipophilic, poorly water soluble therapeutic agent in a composition, wherein the composition is effective to enhance biological absorption or metabolic stability of at least one therapeutic agent, as compared to correspondingly administered therapeutic agent in the absence of a) a phytosterol or phytosterol ester, b) a non-sterol solubilizing agent and c) an enhancing agent.

In yet another aspect, the invention provides a method of treating a condition, comprising administering: a) at least one lipophilic, poorly water soluble therapeutic agent; b) a phytosterol or phytosterol ester; c) a non-sterol solubilizing agent effective for solubilization of the at least one therapeutic agent; and d) an enhancing agent effective to enhance the biological absorption and/or metabolic stability of the at least one therapeutic agent.

In still another aspect, the invention provides a method for maintaining or controlling physiological levels of testosterone and DHT in a subject in need of testosterone replacement, the method comprising administering: a) one or more therapeutic agents selected from testosterone, testosterone esters and combinations thereof, in a formulation selected from immediate release, sustained release, and combinations thereof; b) a phytosterol or phytosterol ester; c) a non-sterol solubilizing agent effective for solubilization of the testosterone or testosterone ester; and d) an enhancing agent effective to enhance the biological absorption and/or metabolic stability of the one or more therapeutic agents; wherein the method is effective to deliver the one or more therapeutic agents to the subject to achieve in the subject a testosterone level of about 300 ng/dL to about 1100 ng/dL and a DHT level of about 30 ng/dL to about 300 ng/dL.

Other aspects, features and embodiments of the invention will be more fully apparent from the ensuing disclosure and appended claims.

BRIEF DESCRIPTION OF THE DRAWINGS

FIG. 7 shows the mean testosterone and DHT concentration profile in 4 beagle dogs dosed with 80 mg testosterone undecanoate in formulation 52 (Table 20), with and without 5 mg finasteride. Phytosterols (400 mg) were co-dosed on both occasions.

FIG. 8 shows the mean testosterone and DHT concentration profile in 4 beagle dogs dosed with 80 mg testosterone undecanoate in formulation 52 (Table 20), with and without 0.5 mg dutasteride. Phytosterols (400 mg) were co-dosed on both occasions.

DETAILED DESCRIPTION OF THE INVENTION, AND PREFERRED EMBODIMENTS THEREOF

Figure 1:
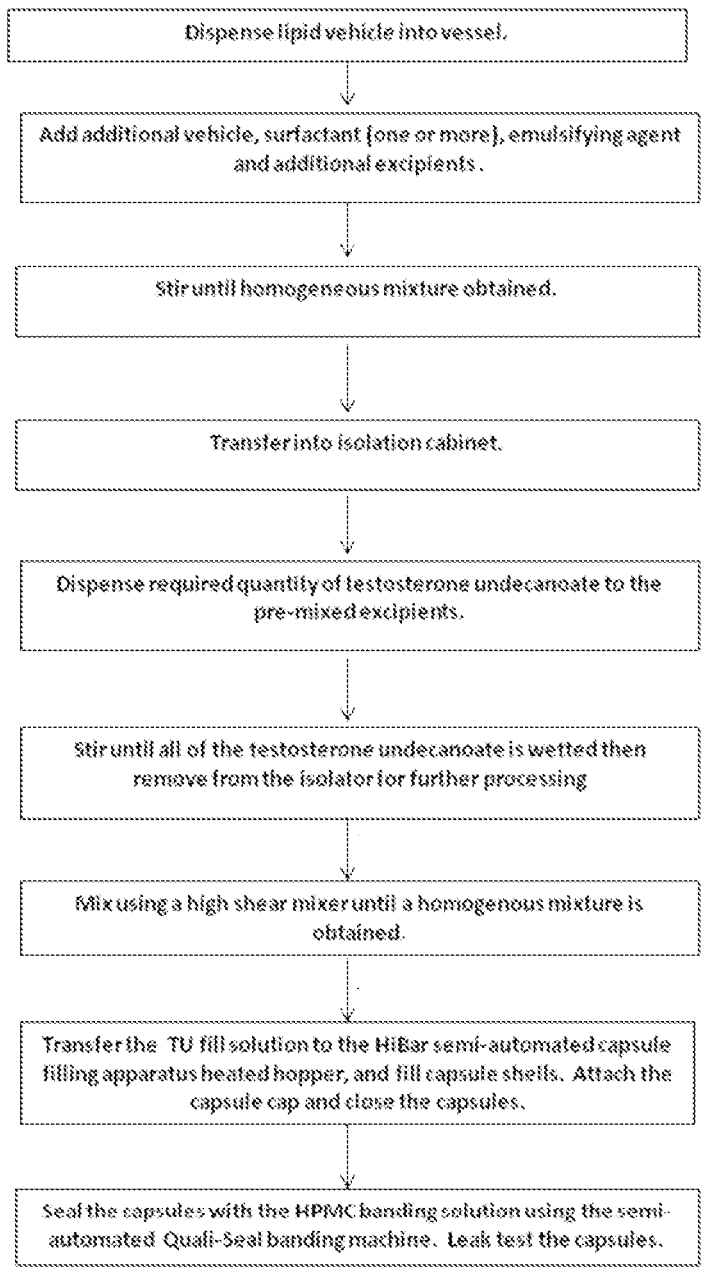
FIG. 1 is a flowchart of the process used to obtain formulations of the invention (Table 20), as described in Example 8.

The present invention relates to improved formulations and methods (e.g., oral, parenteral, intramuscular, transdermal, nasal, sublingual, buccal and/or subcutaneous) for drug delivery involving modulation of solubility, stability, absorption, metabolism, and/or pharmacokinetic profile of the therapeutic agent when administered to a subject in need of such therapeutic agent.

It is noted that as used herein and in the appended claims, the singular forms "a", "and", and "the" include plural referents unless the context clearly dictates otherwise.

Specifically, a formulation or composition of the invention includes a combination of one or more therapeutic agents and a sterol or sterol ester, where inclusion of the sterol or sterol ester provides an additive or synergistic effect with respect to one or more of: solubility, stability, absorption, metabolism, and pharmacokinetic profile of the therapeutic agent. By inclusion of a sterol or sterol ester, smaller amounts of a therapeutic agent are required in the formulation, to achieve a desired pharmacokinetic profile of the therapeutic agent in the subject that is similar to that achieved with a larger amount of therapeutic agent administered without the sterol or sterol ester. In a preferred embodiment the sterol is a phytosterol. A formulation of the invention further includes a non-sterol solubilizer to further modulate the pharmacokinetic profile of the therapeutic agent upon administration of the formulation.

The formulations described herein contain a therapeutic agent in substantially solubilized form. The formulations improve the bioavailability and pharmacokinetic profile of the therapeutic agent after oral, parenteral, intramuscular, transdermal, nasal, sublingual, buccal and/or subcutaneous administration and/or improve patient compliance through an easily followed dosing regimen.

The invention further provides pharmaceutical compositions containing such formulations and methods of making and methods of using such formulations.

The formulations of the invention are formulations for the oral, parenteral, intramuscular, transdermal, nasal, sublingual, buccal and/or subcutaneous administration of a therapeutic agent. The therapeutic agent contained in such formulation can be generally lipophilic in nature (with a log P greater than 2, wherein P is the intrinsic octanol:water partition coefficient) and poorly water soluble. "Poorly water soluble," as referred to herein, refers to drugs for which the dose is not soluble in 250 mL of aqueous solution across a pH range of 1.0 to 7.5. This definition is used in The Biopharmaceutics Classification System (BCS) Guidance published in 2005 by the US Food and Drug Administration. "Lipophilic" as used herein refers to a therapeutic agent that is soluble in lipids, such as fats, oils, and the like. Accordingly, in one embodiment, the invention provides a formulation where a lipid is provided as a solubilizer with the therapeutic agent, so that the administered therapeutic agent is bioavailable, exhibits desirable pharmacokinetic profile and any effects of food on the oral bioavailability of the therapeutic agent are minimized. Furthermore, hydrophobic drugs defined herein encompass both those drugs which are inherently hydrophobic (i.e., having a log P of at least 2) as well otherwise hydrophobic medicaments that have been rendered hydrophobic with suitable modification (e.g., by conjugation to fatty acids and/or lipids).

The therapeutic agent herein may also be referred to herein as an "active agent," "drug" or "pharmacologically active agent." The above-listed terms interchangeably refer to a chemical material or compound which, when administered to an organism (human or animal), is generally bioavailable and induces a desired pharmacologic effect.

Examples of therapeutic agents having the above-described characteristics and therefore capable of administration in formulations of the invention include, but are not limited to: analgesics, anti-inflammatory agents, anti-helminthics, anti-arrhythmic agents, anti-asthma agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, β-blockers, cardic inotropic agents, cell adhesion inhibitors, corticosteroids, cytokine receptor activity modulators, diuretics, anti-parkinsonian agents, gastrointestinal agents, histamine H-receptor antagonists, keratolytics, lipid regulating agents, muscle relaxants, nitrates and other anti-anginal agents, non-steroid anti-asthma agents, nutritional agents, opioid analgesics, sex hormones, stimulants and anti-erectile dysfunction agents.

Additionally, the therapeutic agent may be selected from any agent that is traditionally used as a medicament and lends itself to being administered via oral or parenteral (such as intramuscular, transdermal, nasal, sublingual, buccal and subcutaneous) routes of administration. Such therapeutic agents may be chemotherapeutics; antimycotics; oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, psychotherapeutic agents, anti-diabetic agents and cardiovascular agents, nutraceuticals and nutritional supplements.

Additional therapeutic agents for administration via formulations of the invention include vitamins and co-enzymes including, but not limited to, water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K and Coenzyme Q10.

The therapeutic agent of formulations of the invention may also be selected from botanical bioactive agents, such as: polyphenols, isoflavones, resveratrol, soy isoflavones, grape seed extract polyphenols, curcumin, policosanols, and epigenin; anti-inflammatory plant extracts such as aloe vera, echinacea and chamomile hammamelis extracts; anti-psoriatic plant extracts, such as chinese zizipus jujube; astringents plant extracts such as hammamelis; anti bacterial plant extracts such as artemisia, chamomile, and golden seal; immune modulators such as Echinacea; anti-aging or anti-cancer or anti-photo damage agents; anti-inflammatory agents, such as feverfew parthenolides, rejuvenation agents, carotenoids, beta-carotene, lycopene, astaxanthons, lutein, tocopheryl and retinol.

The therapeutic agent of formulations of the invention may also include coronary drugs, including vasodilators such as nitroglycerin and isosorbide dinitrate, calcium-antagonists such as verapamile, nifedipine and diltiazem, and cardiac-glycosides such as digoxine. Other therapeutic agents that can be usefully administered in the broad practice of the invention include analgesics such as morphine, buprenorphine, etc., and local anaesthetics such as lidocaine, and the like.

Still further, the therapeutic agent of a formulation of the invention may be selected from cholesterol-lowering and triglycerides-lowering drugs: fenofibrate, lovastatin, simvastatin, pravastatin, fluvastatin, atorvastatin, or cerivastatin; anxiolytics, sedatives and hypnotics: diazepam, nitrazepam, flurazepam, estazolam, flunitrazepam, triazolam, alprazolam, midazolam, temazepam, lormetazepam, brotizolam, clobazam, clonazepam, lorazepam, oxazepam, buspirone, and the like; migraine relieving agents: sumatriptan, ergot-amines and derivatives, and the like; drugs for combating motion sickness: cinnarizine, anti-histamines, and the like;

anti-emetics: ondansetron, tropisetron, granisetrone, metoclopramide, and the like; disulfiram; and vitamin K.

Further examples of therapeutic agents for use in formulations of the invention include: chemotherapeutic agents, including, but not limited to: cisplatin (CDDP), procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate, or any analog or derivative variant thereof; antibiotic drugs: Tetracyclines such as tetracycline, doxycycline, oxytetracycline, chloramphenicol etc.; Macrolides such as erythromycin and derivatives, etc.; Antivirals: such as acyclovir, idoxuridine, tromantadine etc.; Antimycotics: Miconazole, ketoconazole, fluconazole, itraconazole, econazole, terconazole, griseofulvin, and polyenes such as amphotericin B or nystatine etc. Anti-amoebics: Metronidazole, metronidazole benzoate and tinidazole etc.; Anti-inflammatory drugs: steroids or NSAIDs such as indomethacin, ibuprofen, piroxicam, diclofenac etc.; Anti-allergics: Disodium cromoglycate etc.; Immunosuppressive agents: cyclosporine etc.; Antimicrobial agents that may be used include, but are not limited to, naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, β-lactamase inhibitors; meziocillin, piperacillin, aztreonam, norfloxacin, trimethoprim, ceftazidime, ceftriaxone and dapsone; Antifungal agents include, but are not limited to: ketoconazole, fluconazole, nystatin, itraconazole, clomitrazole, and amphotericin B. Antiviral agents, include, but are not limited to: acyclovir, trifluridine, idoxorudine, foscarnet, ganciclovir, zidovudine, dideoxycytosine, dideoxyinosine, stavudine, famciclovir, didanosine, zalcitabine, rifimantadine, and cytokines. Antihistamines useful for therapeutic administration include, but are not limited to: cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine. Decongestants and antitussives includ, but are not limited to: dextromethorphan, levopropoxyphene napsylate, noscapine, carbetapentane, caramiphen, chlophedianol, pseudoephedrine hydrochloride, diphenhydramine, glaucine, pholcodine, and benzonatate. Other therapeutic agents administerable in formulations of the invention include: anesthetics, such as: etomidate, ketamine, propofol, and benodiazapines (e.g., chlordiazepoxide, diazepam, clorezepate, halazepam, flurazepam, quazepam, estazolam, triazolam, alprozolm, midazolam, temazepam, oxazepam, lorazepam), benzocaine, dyclonine, bupivacaine, etidocaine, lidocaine, mepivacaine, promoxine, prilocaine, procaine, proparcaine, ropivacaine, and tetracaine. Other useful agents may include: amobartital, aprobarbital, butabarbital, butalbital mephobarbital, methohexital, pentobarbital, phenobarbital, secobarbital, thiopental, paral, chloral hydrate, ethchlorvynol, clutethimide, methprylon, ethinamate, and meprobamate; Analgesics, including, but not limited to: opioids such as morphine, mepidine, dentanyl, sufentranil, alfentanil, aspirin, acetaminophen, ibuprofen, indomethacine, naproxen, atrin, isocome, midrin, axotal, firinal, phrenilin, ergot and ergot derivatives (wigraine, cafergot, ergostat, ergomar, dihydroergotamine), imitrex; Diuretics including, but not limited to: acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprionolactone, canrenone, and potassium canrenoate; Anti-inflammatories including, but not limited to: salicylic acid derivatives (e.g. aspirin) paraminophenol derivative (e.g. acetaminophen) indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone); Psychotherapeutic agents including, but not limited to: thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, serzone, desyrel, nardil, parnate, eldepryl; Cardiovascular agents including, but not limited to: nitroglycerin, isosorbide dinitrate, sodium nitroprisside, captopril, enalapril, enalaprilat, quinapril, lisinopril, ramipril, losartan, amrinone, lirinone, vesnerinone, hydralazine, nicorandil, prozasin, doxazosin, bunazosin, tamulosin, yohimbine, propanolol, metoprolol, nadolol, atenolol, timolol, esmolol, pindolol, acebutolol, labetalol, phentolamine, carvedilol, bucindolol, verapamil, nifedipine, amlodipine and dobutamine.

The compositions of the invention, in various embodiments provide effective formulations for oral, parenteral, intramuscular, transdermal, nasal, sublingual, buccal and/or subcutaneous administration of androgens as the therapeutic agent.

Androgens have diverse effects in many tissues. Recent studies have begun to elucidate the mechanisms of their anabolic effects. The mechanistic understanding is leading to an increase in clinical usefulness for many disease states. The strongest indication for the use of androgens is for replacement therapy in hypogonadal men to maintain sexual function and libido, muscle strength, and prevent the development of osteoporosis. Another use is for the stimulation of erythropoiesis in condition of bone marrow suppression such as aplastic anaemia.

As men age, testosterone concentrations are reduced and considerable interest has developed over the use of physiologic doses of testosterone to return concentrations to the level of young men. Testosterone administration increases muscle protein synthesis, muscle strength, improve mood and quality of life in older men. There is also considerable interest in the use of androgens as replacement therapy in post-menopausal women and the benefits of improvement in muscle strength, sexuality and libido are compelling in this group of women.

Androgens have also shown clinical usefulness in the treatment of muscle wasting syndromes. In men with AIDS wasting syndrome, there was a direct relationship between the loss of lean body mass and the degree of hypogonadism present in the disease. Testosterone replacement in men and women with AIDS wasting syndrome increases weight gain in this debilitating condition. Androgens have also shown anabolic effects on muscular dystrophy, metabolic syndrome, and Alzheimer disease (Diab. Nutr. Metab. 12:339-343, 1999).

Androgen-containing formulations are therefore of interest in preparations for male contraception and male HRT (hormone replacement therapy). Androgens can also be used in the female, e.g. as androgen replacement therapy in postmenopausal women. Androgens may particularly be used as a replacement for or a supplement to endogenous testosterone. Thus, e.g., in male HRT, androgen is administered in order to relieve the undesired effects of the (partial) androgen-deficiency including, but not limited to, effects on bone mineral density, changes in body composition, reduction of sexual interests and erectile dysfunction. In one embodiment, the invention provides androgen-containing formulations useful for administration of androgens to a subject in need of such administration.

In one embodiment, the therapeutic agent of a formulation of the invention may be selected from testosterone and esters thereof. Testosterone esters may include, but are not limited to, any $C_1$-$C_{24}$ esters of testosterone, including testosterone proprionate, testosterone enanthate, testosterone cypionate, testosterone undecanoate, testosterone cyclohexylmethylcarbonate, and testosterone triglyceride. Additional testosterone esters can include, but are not limited to, formate, acetate, butyrate, valerate, hexanoate, heptanoate, octanoate, nonanoate, and decanoate. In one embodiment, the therapeutic agent is a testosterone ester with a carbon structure that is linear or branched, and saturated, monounsaturated or polyunsaturated.

As used herein, the identification of a carbon number range, e.g., in $C_1$-$C_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the invention, and that ranges of carbon numbers specifically excluding a carbon number or numbers are included in the invention, and sub-ranges excluding either or both of carbon number limits of specified ranges are also included in the invention. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the invention, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range.

"Alkyls" as used herein include, but are not limited to, methyl, ethyl, propyl, isopropyl, butyl, s-butyl, t-butyl, pentyl and isopentyl and the like. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. "Cycloalkyls" as used herein include, but are not limited to cyclopropyl, cyclobutyl, cyclopentyl, cyclohexyl and the like. In all chemical formulae herein, a range of carbon numbers will be regarded as specifying a sequence of consecutive alternative carbon-containing moieties, including all moieties containing numbers of carbon atoms intermediate the endpoint values of carbon number in the specific range as well as moieties containing numbers of carbon atoms equal to an endpoint value of the specific range, e.g., $C_1$-$C_6$, is inclusive of $C_1$, $C_2$, $C_3$, $C_4$, $C_5$ and $C_6$, and each of such broader ranges may be further limitingly specified with reference to carbon numbers within such ranges, as sub-ranges thereof. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

In a further embodiment of the invention, the therapeutic agent is selected from testosterone and/or testosterone undecanoate (TU). In a further embodiment, the formulation contains a combination of testosterone and one or more testosterone esters as therapeutic agents, where the ratio of testosterone to testosterone ester is from about 0:100 or 100:0 to about 1:1, preferably from about 1:10 to about 1:3 or from about 10:1 to about 3:1. In various other embodiments, the ratio of testosterone to testosterone ester may be in a range having a lower value of any of 0, 0.01, 0.05, 0.1, 0.15, 0.2, 0.33, 0.5, 1.0, 2.0 and 3.0 and having an upper value of any of 90.5, 91.0, 91.25, 91.5, 91.75, 92.0, 93.0, 94.0, 95.0, 97.5, 99.0, 99.5, 99.75, 99.9, 99.95 and 100.0. In a preferred embodiment, the formulation contains testosterone and/or TU as therapeutic agents.

As used herein, references to the amounts of therapeutic agents as percent by weight of a formulation may be made as equivalent to T. For purposes of such calculations with regard to testosterone esters, it is noted that 100 mg of T is equivalent to 139 mg testosterone enanthate, 158 mg testosterone undecanoate, 143 mg testosterone cypionate, and 183 mg testosterone palmitate. Amounts of therapeutic agents included in formulations of the invention may be proportionally adjusted, relative to testosterone.

The invention addresses the problem of providing an orally active androgen formulation that is well absorbed in the human body. It has been well established by dog (Shackleford J. Pharmacol. and Exp. Ther., 925-933, 2003) and human studies that testosterone undecanoate is absorbed almost exclusively via the intestinal lymphatics (Coert et al., Acta Endocrinol (Copenh), 789-800, 1975; Nieschlag et al., Acta Endocrinol (Copenh), 366-374, 1975; Horst et al., Klin Wochenschr, 875-879, 1976), thereby bypassing hepatic metabolism. Particularly, the invention provides SEDDS formulations of testosterone undecanoate containing phytosterols which enhances lymphatic absorption of TU by about 10% to about 300% over current commercial products, Andriol® Testocaps®, and known SEDDS formulations (U.S. Patent Application No. 2008/0317844; U.S. Patent Application No. 2010/0173882). The invention also provides a formulation of TU and/or testosterone that has a higher strength than currently known TU formulations. In one embodiment, the composition is formulated for parenteral administration. In a further embodiment, the parenteral administration is intramuscular. One embodiment of the present invention also contemplates a formulation that releases the therapeutic agent into the patient's system at physiologically effective levels, over a period of up to 12 hours. Preferably, the formulation releases the therapeutic agent into the patient's system at physiologically effective levels over a period of up to 24 hours.

The invention provides embodiments where the formulation is effective for any of immediate release of the therapeutic agent, sustained release of the therapeutic agent, delayed release of the therapeutic agent, and/or any other modified release of the therapeutic agent. In one embodiment the invention provides a composition formulated for a combination of immediate and modified release of testosterone and/or testosterone esters.

The oral administration of hormones such as testosterone or estrogen has proven challenging. Testosterone is generally administered by oral ingestion in a bonded form as testosterone undecanoate, methyltestosterone, or testosterone cyclodextrin complex, to avoid the first pass effect. When administered in a regimen of hormone replacement therapy, it is desired to have sustained release properties, yet these forms of testosterone must be taken multiple times daily.

It was a general belief that testosterone itself could not be administered by oral ingestion. According to The Pharmacological Basis of Therapeutics, 10th ed., by Goodman and Gilman, oral administration of testosterone leads to absorption into the hepatic circulation but results in rapid metabolism by the liver. Therefore, oral ingestion is ineffective in delivering testosterone systemically. However, some researchers have further investigated oral administration of testosterone.

Svend Johnsen et al., in the publication entitled "Therapeutic Effectiveness of Oral Testosterone," (Johnsen et al., *Lancet*, 1974, 21; 2(7895):1473-5) described an oral administration of 200 mg of micronized testosterone, with a particle size in the range of 2 to 5 microns, to four patients with no testicular function. It was found that, for a period of about 5 to 7 hours, the total serum testosterone of the patient was in the range of about 300 to 900 ng/dL. Johnsen et al. recommended 200 mg testosterone administered twice daily. However, Johnsen et al. failed to address improving the pharmacokinetic properties of testosterone in order to administer the dose only once a day.

Marie Fogh et al., in the publication entitled "Serum-Testosterone During Oral Administration of Testosterone in Hypogonadal Men and Transsexual Women," (Føgh et al., *Acta. Endocrinol.* (Copenhagen), 1978, 87(3):643-9) described an oral administration of 200 mg of micronized testosterone twice daily. The two doses provided total serum testosterone within the normal range for greater than about 12 hours. A single 200 mg dose of orally administered testosterone with a particle size in the range of about 125-400 microns provided a total serum testosterone in the normal range for from about 5 to 7 hours. In view of the large doses required to maintain the desired serum levels of testosterone, and the possible side effects of such doses, Føgh et al. recommended not administering testosterone orally.

P. R. Daggett et al., in the article entitled "Oral Testosterone, a Reappraisal," (Daggett, et al., *Horm Res.* 1978, 9(3):121-9) described an oral administration of 200 mg of micronized testosterone twice daily. The dosage provided a double peak effect, with a desired level of serum testosterone for about 4 hours for each peak. Daggett et al. found that the administration of oral testosterone was "unsuitable for routine use."

Nieschlag et al., in the publication entitled "Influence of Sex, Testicular Development and Liver Function on the Bioavailability of Oral Testosterone," (Nieschlag et al., *Eur. J. Clin. Invest.* 1977, 7(2):145-7) described orally administering 63 mg of testosterone in arachis oil to hypogonadal men. The serum level of testosterone rose to the desired level for a period of about 1 to 2 hours. Nieschlag et al. stated that oral testosterone "should be considered with caution, since higher testosterone doses would be needed to exceed the developing capacity of the liver to metabolize testosterone."

In the context of a general consensus that testosterone cannot be efficaciously orally administered, none of the above references discusses the possibility of providing sustained release properties or combining testosterone with a testosterone ester to modulate the release profile.

"Modified release," as used herein, generally refers to release of a drug that differs from immediate release of the drug under the same conditions via the same route of administration. Modified release may include each of immediate release, sustained release and delayed release. "Sustained release," as used herein, generally refers to release of a drug whereby the level of drug available to the patient is maintained at some level over a desired period of time. A variety of methods and formulations are used to provide sustained release of drugs. U.S. Pat. No. 5,567,439, describing methods of sustained release, is hereby incorporated by reference.

In one embodiment of the invention, the desired resulting level of total serum testosterone in a subject is in the range of from about 300 to about 1100 ng/dL in a male subject and in the range of from about 30 to about 110 ng/dL in a female subject. A formulation of the present invention, with testosterone or TU as the therapeutic agent delivers the desired level of serum testosterone for a minimum time period of about 8 to about 12 hours. After administration of a formulation of the invention with testosterone or TU as the therapeutic agent, the desired level of serum testosterone may be maintained for more than 12 hours. In a further embodiment the desired level of serum testosterone may be maintained for about 24 hours.

In exemplary formulations of the invention, the formulation is designed for administration three times a day (tid), two times a day (bid), or once a day (qd). Administration of a formulation of the invention may be by any regimen that achieves the desired resulting level of total serum testosterone in the target subject.

The formulation and methods of the present invention provide the ability to administer testosterone and/or testosterone ester in combination with sterols and/or sterol esters to achieve improved sustained release properties, as described more fully herein. In one embodiment, the administration is oral delivery. In other embodiments, the administration is parenteral, transdermal, nasal, sublingual, buccal or subcutaneous.

While various embodiments herein describe oral delivery of formulations and pharmaceutical compositions containing the therapeutic agent, it is further envisioned that the delivery of the drug is performed by any suitable delivery mechanism that provides therapeutically effective levels of the therapeutic agent. Other delivery routes that are compatible with the selected therapeutic agent and sterols or sterol esters are also contemplated as within the invention. Accordingly, delivery methods of formulations or pharmaceutical compositions described herein include, but are not limited to sublingual administration, buccal administration, parenteral administration, intraperitoneal (i.p.) administration, intravenous (i.v.) administration, intraarterial (i.a.) administration, topical administration, transdermal administration, intradermal (i.d.) administration, intramuscular (i.m.) administration, subcutaneous (sc) administration, and nasal administration.

In a further embodiment the invention provides a formulation including more than one therapeutic agent. Where a second therapeutic agent is included in a formulation of the invention, the weight ratio of the primary therapeutic agent to the secondary therapeutic agent may be varied and will depend upon the effective dose of each ingredient. Each therapeutic agent contained in the composition or dosage form will be present in a therapeutically effective amount.

As described in detail above, the low bioavailability of a therapeutic agent caused by the high first-pass effect in the liver can be reduced by optimizing lymphatic absorption of the therapeutic agent. The present invention enables enhancement of the lymphatic absorption of testosterone esters and/or a combination of testosterone with testosterone esters, by formulations including sterols. In one embodiment, the sterols are phytosterols. It is shown herein that sterols, phytosterols and/or phytosterol esters modulate the solubility, stability, absorption, metabolism and pharmacokinetic profile of therapeutic agents that are lipophilic.

In another embodiment, the invention provides a formulation for the administration of a therapeutic agent in which the formulation contains a sterol in addition to the therapeutic agent, to provide desired properties of solubility, stability, absorption, metabolism and/or pharmacokinetic profile of the therapeutic agent. In a particular embodiment, the therapeutic agent is selected from testosterone and testosterone undecanoate.

As used herein, "stability" includes the stability of both the formulation and the therapeutic agent, both prior to administration and after administration to an individual. An improved stability prior to administration enables longer shelf life, less protective packaging, or storage at more aggressive environments. An improved stability after administration enables improved pharmacokinetic properties, such as higher exposure, or longer duration of action.

"Sterols," as used herein, include all of plant, animal and fungal sterols. The sterols may be pure or may be a mixture of sterols. In one embodiment, the sterol is cholesterol. In another embodiment, the sterol is a "phytosterol," a plant sterol or stanol, used herein to refer generally to plant-derived sterols or plant-derived stanols, phytochemicals that are added to foods, or supplements. Use of the term sterols also includes sterol esters, of any of plant-derived, animal-derived or fungal-derived sterol. "Sterol esters," as used herein refer to plant sterols or stanols that have been esterified by creating an ester bond between a fatty acid and the sterol or stanol. Fatty acids used in esterification are plant-derived, animal-derived or fungal-derived. Esterification occurs in intestinal cells and is also an industrial process. Esterification may make plant sterols and stanols more fat-soluble so they are easily incorporated into fat-containing foods, including margarines and salad dressings. Exemplary sterols useful in the invention may include, but are not limited to, phytosterols, cholesterol, beta-sitosterol, and/or sitostanol. CardioAid XF® is a commercially available phytosterol mixture comprising from 40% to 58% by weight of beta-sitosterol; from 20% to 30% by weight of campesterol; from 14% to 22% by weight stigmasterol: from 0 to 6% by weight brassicasterol; from 0 to 5% by weight sitostanol; and from 0 to 15 mg/g tocopherols.

Prior to the present invention, it was well known that a fed state or a fasting state of the subject could severely interfere with the delivery of a therapeutic agent to that subject. As described above, the interactions between food and drugs should be individually evaluated.

The pioneering work of Borgstrom et al. (J. Clin Invest; 36:1521-1529, 1957) and Carey et al. (Am J Med; 49:590-598, 1970), as well as many others, contributed to the finding that the bile acid mixed micelle (BAMM) in the fed state and the bile acid (BA) micelle in the fasted state constitute the endogenous surfactant system that is responsible for the delivery or presentation of extremely lipophilic drugs to the enterocyte brush border region.

Cholesterol with a C log P (calculated log P) of 12 and a water solubility of ~10 ng/mL is efficiently absorbed from the intestine by presentation of cholesterol dissolved in the BAMM droplets to the enterocyte brush border mucosa with subsequent collisional transfer to the glycocalyx. Many other extremely insoluble and lipophilic compounds are absorbed more efficiently in the fed state where the BAMM is present. The BAMM system is more effective than the BA system because of the higher miceller concentration in the fed as compared to the fasted state. The plant phytosterols which are present in food have similar C log P and solubility but are slightly different in structure of the side chain and displace a significant percentage of cholesterol from the BAMM and reduce cholesterol absorption.

Accordingly, the present inventor selected sterols for investigation as providing a modulating effect on the solubility, stability, absorption, metabolism and/or PK profile of various lipophilic drugs. The modulating effect provided by sterols in formulations and methods of the invention is dependent upon the concentration of the sterols. In a particular embodiment the sterols are phytosterols dissolved in a formulation and/or co-dosed as a solid with a formulation. Since phytosterols are very lipophilic in nature (log P=12), high concentration of phytosterols suspended in lipid-based formulations bind strongly to the lipophilic drugs making the drug insoluble and unavailable for absorption. However, phytosterols dissolved in the lipid-based formulation to saturation (about 1% to about 20%) increase the solubility of the lipophilic drug, and increase bioavailability. (Tables 1-20 and FIGS. 5 and 6).

In food effect studies done to date and guidance issued by regulatory agencies, the fat content of the diet and its influence on the drug absorption has been emphasized. No attention has been given to the types of fat (saturated, monounsaturated, polyunsaturated, etc.) and the amount of cholesterol or plant sterols present in each meal. The vegetable oils contain a number of sterols that differ from cholesterol by having ethyl or methyl groups or unsaturation in the side chain. The predominant ones—sitosterol, stigmasterol, and campesterol—can be present in Western diets in amounts almost equal to dietary cholesterol (Miettinen T A, Tilvis R S, Kesäniemi Y A. *Am J Epidemiol.* 1990; 131:20-31). The most prominent is β-sitosterol, which differs from cholesterol in that it has an ethyl group at carbon 24 of the side chain. In the early 1950s it was noted that the addition of sitosterol to the diet of cholesterol-fed chickens or rabbits lowered cholesterol levels in both species and inhibited atherogenesis in the latter (Pollak O J, Kritchevsky D. *Monogr Atherosclerosis,* 1981; 10:1-219). Sitosterol or mixtures of soy sterols were studied extensively as cholesterol-lowering agents between 1950 and 1960 (Lees A M, Mok H Y I, Lees R S, McCluskey M A, Grundy S M. *Atherosclerosis,* 1977; 28:325-338). The preparations achieved cholesterol lowering of approximately 10% (Vahouny G V, Kritchevsky D. In: Spiller G A, ed. *Nutritional Pharmacology.* New York, N.Y.: Alan R Liss Inc; 1981:31-72.). The mode of action appears to involve inhibition of cholesterol absorption, although the plant sterols themselves are absorbed very poorly (Tilvis R S, Miettinen T A. *Am J Clin Nutr.,* 1986; 43:92-97). The mechanism of inhibition of cholesterol absorption is believed to be through crystallization and co-precipitation. Ingestion of 1 g of β-sitosterol reduced absorption of cholesterol by 42% in a meal containing 500 mg of cholesterol (Mattson F H, Grundy S M, Crouse J R. *Am J Clin Nutr.,* 1982; 35:697-700). The decrease in plasma cholesterol is probably due to an increase in LDL receptor activity. However, the decline in plasma cholesterol is relatively less than the decrease in absorption, presumably because of a compensatory increase in cholesterol synthesis.

In the 1980s it was demonstrated that sitostanol, a 5-α saturated sitosterol derivative, reduced the intestinal absorption of cholesterol and serum cholesterol more effectively than sitosterol and at doses below those of sitosterol. (Heinemann T, Leiss O, von Bergmann K., *Atherosclerosis,* 1986; 61:219-223). In a recent study (Miettinen T A, Puska P, Gylling H, Vanhanen H, Vartiainen E., *New. Eng. J. Med.,* 1995; 333:1308-1312) sitostanol was interesterified with margarine, and the resultant product (1.9 to 2.6 g sitosterol per day) exhibited a hypocholesterolemic effect in a population with mild hypercholesteremia. The mean 1-year reduction in plasma cholesterol was 10.2%. The sitostanol was not absorbed and did not appear to interfere with absorption of fat-soluble vitamins.

Phytosterols have a long history of safe use in humans. The drug Cytellin® was marketed in the United States between 1954 and 1982. The dosage was 6-18 g/d, with higher dosages recommended for those patients not responding to the standard dose. Dosages as high as 45 g/d were reported to be well tolerated without serious side effects (Eli Lilly Package Insert M100 Suspension Cytellin® (Beta and Di-hydrobeta sitosterols). A drug product indicated for the reduction of hypercholesterolemia. Dated 1954.). In the modern era, phytosterols have been used as margarine additives since about 1995, with the introduction of stanol esters to the Finnish market, and in 2000 with the introduction of sterol esters under Novel Foods regulations in the EU. As a requirement for market approval, post-launch monitoring was conducted in the EU, with no unpredicted side effects reported (Lea L J, Hepburn P A. Safety evaluation of phytosterol esters. Part 9: Results of a European post-launch monitoring programme. *Food Chem Toxicol.,* 2006; 44:1213-22.). The recommended plant sterol/stanol dosages for margarine and other foods are relatively low compared with that of Cytellin®. Consumption levels of 400 mg twice daily of phytosterols are now recommended. (Press release dated Feb. 24, 2003 at World Wide Web address: npicenter.com/anm/templates/newsATemp.aspx?articleid=4011&zoneid=3).

The principal (n-3) long-chain polyunsaturated fatty acids (LCPUFA) in marine oils, eicosapentaneoic acid (EPA; 22:5(n-3)) and docosahexaenoic acid (DHA; 22:6(n-3)), have been shown to possess a wide range of physiological effects, from alterations in circulating plasma lipids to eicosanoid and cytokine production. There is considerable evidence to support reductions in triglycerides and improvement in circulating HDL-cholesterol in response to high dosage (1-5 gm/d) (n-3) LCPUFA oil supplementation.

In a recent clinical study, it was found that combined supplementation of (n-3) LCPUFA (1.4 g/d) as oils with phytosterols (2 g/d) has both synergistic and complementary lipid-lowering effects in hyperlipidemic men and women. The combination of phytosterols and (n-3) LCPUFA has been shown to reduce plasma total cholesterol by 13.3% and LDL-cholesterol by 12.5%. The HDL-cholesterol concentration was increased by (n-3) LCPUFA (7.1%) alone and in combination with phytosterols (8.6%), whereas phytosterol treatment alone had no effect. Plasma triglyceride concentration was lowered by (n-3) LCPUFA (22.3%) alone and in combination with phytosterols (25.9%), whereas phytosterol treatment alone had no effect. (Michelle A. Micallef et al., J. Nutr. 138: 1086-90, 2008)

Testosterone is implicated as one of the gender-related risk factors for coronary artery disease in men due to its HDL-C lowering effect. Weekly administration of 200 mg TE to male powerlifters decreased HDL-C and apolipoprotein A significantly but total cholesterol, LDL-C or triglyceride levels were not altered (Zmuda et al, Metabolism 42: 446-450, 1993).

In a further embodiment, testosterone and/or testosterone ester formulations of the present invention containing LCPUFA and phytosterols may be used to minimize the HDL-C lowering effect observed with currently available testosterone and/or testosterone ester products delivered via oral, parenteral, intramuscular, transdermal, nasal, sublingual, buccal and/or subcutaneous routes of administration.

In one embodiment, the invention provides a formulation for the oral administration of a therapeutic agent which contains testosterone, testosterone undecanoate and/or another testosterone ester in combination with a phytosterol, where the phytosterol provides modulation of one or more of: solubility, stability, absorption, metabolism and pharmacokinetic profile of the testosterone or testosterone ester. The concentration of the dissolved phytosterol(s) ranges from about 1% to about 30% of the formulation, preferably about 2% to about 20% solubilized in the formulation to exhibit the desired modulating effect.

In another embodiment, the formulation further comprises LCPUFA, LCPUFA oils, LCPUFA esters, and mixtures thereof in addition to the phytosterol and therapeutic agent.

In yet another embodiment, the formulation further comprises solubilizers (lipids, surfactants, etc.), and LCPUFA, LCPUFA oils, LCPUFA esters, and mixtures thereof, in addition to the phytosterol and therapeutic agent.

In one embodiment, the amount of phytosterol and/or phytosterol esters in the formulation is an amount effective to modulate the solubility, stability, metabolism and/or bioavailability to deliver the desired PK profile for a minimum of about 8 to about 12 hours. In another embodiment, the modulation will last longer than 12 hours, preferably about 24 hours. This modulative effect is important for hormone replacement therapies, e.g., in elderly men with partial androgen deficiency (PADAM patients), in that a deficient plasma level of testosterone can be appropriately corrected.

Another embodiment of a dosing regiment for hormone replacement therapy (HRT) involves administering orally a testosterone and/or testosterone ester formulation to hypogonadal men for a specified duration (1 week to 6 months) to achieve normal physiological levels of testosterone (300 ng/dL-1100 ng/dL in a male subject), followed by parenteral administration of a long acting intramuscular product of the present invention every (6-12 weeks) for maintenance therapy.

As described in detail above, sustained solubilization is a desirable characteristic in formulations for enhancing the bioavailability of water insoluble, lipophilic drugs. In one embodiment, the invention includes formulations including a therapeutic agent, a sterol and a non-sterol solubilizing agent for solubilization of the therapeutic agent. As such, absorption is not dependent on the dissolution of the therapeutic agent from the formulation in the patient's gastrointestinal tract, as all or a substantial fraction of the therapeutic agent in the formulation is already solubilized prior to administration to the patient, increasing the amount of therapeutic agent available for absorption. In a particular embodiment the therapeutic agent is selected from testosterone and testosterone undecanoate and the sterol is a phytosterol.

A "solubilizer" as referred to herein, may also be referred to as a "solubilizing agent." The terms are used interchangeably.

Solubilizers included in formulations of the invention are any pharmaceutically acceptable material that has a solubility for TU of at least about 1 mg per gram of the solubilizer, more preferably at least about 40 mg per gram of the solubilizer, and most preferably at least about 100 mg per gram of the solubilizer. The solubilizer is preferably present in an amount such that a significant fraction of the therapeutic agent is solubilized in the composition and is capable of providing an immediate and therapeutically effective amount of the therapeutic agent to a patient in a readily absorbable form upon administration. In one embodiment, the therapeutic agent is testosterone undecanoate, which provides a therapeutically effective amount of testosterone to a patient. Preferably, the solubilizers of the present invention can also increase the solubilization of TU or any other therapeutic agent when the composition contacts an aqueous medium, and particularly gastro-intestinal fluids upon administration of the dosage form containing the composition. Thus, the solubilizers as provided herein improve the dissolution profile of TU or any other therapeutic agent and thereby the bioavailability of TU or any other therapeutic agent. In various embodiments, the solubilizer is a non-sterol solubilizer.

In one embodiment, the solubilizers are selected from triglycerides, diglycerides, monoglycerides, free fatty acids, and fatty acid esters and derivatives thereof, individually or in combination. Examples of solubilizers include, but are not limited to, propylene glycol dicaprylate/caprate, caprilic/capric triglyceride, caprylic/capric/linoleic triglyceride, e.g. synthetic medium chain triglycerides having $C_{8-12}$ fatty acid chains or other derivatized (synthetic) triglycerides of the type known and commercially available under Miglyol 810, 812, 818, 829 and 840, linoleic acid, linoleic acid ethyl ester, fish oils as free fatty acids, their esterification and their transesterification products, e.g., of the type known and commercially available under EPAX 6000 FA, EPAX 4510 TG, individually or in combination. Additional examples include vegetable oils and $C_{12-18}$ fatty acid mono-, di- and triglycerides prepared by individual admixing or as transesterification products of vegetable oils (such as soybean oil, almond oil, sunflower oil, olive oil or corn oil) with glycerol. Particularly preferred lower alcohol fatty acid esters include ethyl oleate, ethyl linoleate, ethyl caprylate, ethyl caprate, isopropyl myristate, isopropyl palmitate and mixtures thereof.

In the art of pharmaceutical formulation, vitamin E substances have been known for their reducing potential and typically used as antioxidants in pharmaceutical compositions. The inventor has found, however, that vitamin E substances have unexpected solubilization power toward testosterone undecanoate and other hydrophobic therapeutic agents. Therefore, in one embodiment, the formulation includes a vitamin E solubilizer.

The inventor also has surprisingly found that nitrogen-containing solvents have unexpected solubilization power toward testosterone undecanoate and other hydrophobic therapeutic agents relative to other commonly used non-nitrogen containing solvents such as glycerol, propylene glycol, and polyethylene glycols. The nitrogen-containing solvent solubilizer may be selected from, but is not limited to: dimethylformamide, dimethylacetamide, N-alkylpyrrolidone, N-hydroxyalkylpyrrolidone, N-alkylpiperidone, N-alkylcaprolactam and mixtures thereof wherein alkyl is a $C_{1-12}$ branched or straight chain alkyl. Particularly preferred nitrogen-containing solvents include N-methyl 2-pyrrolidone, N-ethyl 2-pyrrolidone or a mixture thereof. Alternatively, the nitrogen-containing solvent may be in the form of a polymer such as polyvinylpyrrolidone. In another embodiment, the formulation includes a solubilizer selected from nitrogen-containing solvents.

In additional research, the inventor has further surprisingly found that replacing one or more of the hydroxyl groups of glycerol and propylene glycol with, for example, a $C_2$-$C_{24}$ alkyl ester, results in a propylene glycol or glycerol fatty acid ester with an unexpectedly high solubilizing power for testosterone undecanoate. In another embodiment, the formulation includes a solubilizer selected from dehydroxylated, esterified non-nitrogen containing solvents, where the hydroxyl group has been replaced with an ester.

Similarly, additional research has yielded other unexpectedly effective solubilizers for testosterone undecanoate, including esters of monohydric alcohols such as ethanol and ethylene glycols such as polyethylene glycols, with an organic acid such as acetic acid, fatty acids and citric acids.

Another group of solubilizers for use in formulations of the invention includes phospholipids. Solubilizing phospholipids include, but are not limited to, phosphatidylcholine, phosphatidylethanolamine, phosphatidylserine, phosphatidylinositol, lecithins, lysolecithins, lysophosphatidylcholine, polyethylene glycolated phospholipids/lysophospholipids, lecithins/lysolecithins and mixtures thereof.

In still another embodiment, a formulation of the invention contains a solubilizer that is a hydrophobic or hydrophilic surfactant that would enhance the galenic properties of the therapeutic agent within the formulation. Examples of suitable surfactants include, but are not limited to: polyoxyethylene-sorbitan-fatty acid esters; e.g., mono- and tri-lauryl, palmityl, stearyl and oleyl esters; e.g., products of the type known as polysorbates and commercially available under the trade name Tween®; polyoxyethylene fatty acid esters, e.g., polyoxyethylene stearic acid esters of the type known and commercially available under the trade name Myrj®; polyoxyethylene castor oil derivatives, e.g., products of the type known and commercially available as Cremophors®. Particularly suitable are polyoxyl 35 castor oil (Cremophor®EL) and polyoxyl 40 hydrogenated castor oil (Cremophor®RH40); α-tocopherol, α-tocopheryl polyethylene glycol succinate (vitamin E TPGS), α-tocopherol palmitate and α-tocopherol acetate; PEG glyceryl fatty acid esters such as PEG-8 glyceryl caprylate/caprate (commercially known as Labrasol®), PEG-4 glyceryl caprylate/caprate (Labrafac® Hydro WL 1219), PEG-32 glyceryl laurate (Gelucire® 44/14), PEG-6 glyceryl mono oleate (Labrafil® M 1944 CS), PEG-6 glyceryl linoleate (Labrafil® M 2125 CS); propylene glycol mono- and di-fatty acid esters, such as propylene glycol laurate, propylene glycol caprylate/caprate; also diethyleneglycol-monoethylether (DGME), commercially known as Transcutol® (Gattefosse, Westwood, N.J.); sorbitan fatty acid esters, such as the type known and commercially available under the name Span® (e.g., Span 85); polyoxyethylene-polyoxypropylene co-polymers, e.g., products of the type known and commercially available as Pluronic® or Poloxamer®; glycerol triacetate; and monoglycerides and acetylated monoglycerides, e.g., glycerol monodicocoate (Imwitor® 928), glycerol monocaprylate (Imwitor® 308), and mono- and di-acetylated monoglycerides.

As described in detail above, one widely utilized approach to achieve sustained solubilization is to utilize formulations within a lipid vehicle containing surfactants that constitute a SEDDS or SMEDDS, to effect spontaneous emulsification upon contact of the lipid with fluids in the GI tract.

Hydrophilic-Lipophilic Balance (HLB) is a term used to describe an arbitrary scale from 0 to 40 depicting the Hydrophilic/Lipophilic Balance of a surfactant. Products with low HLB are more oil soluble. High HLB represents good water solubility. HLB is a numerically calculated number based on the surfactants' molecular structure. It is not a measured parameter.

An optimal surfactant hydrophilic lipophilic balance (HLB) for emulsification was found to be around 10 (Shah, N. H. et. al., Int. J. of Pharmaceutics, 106 (1994) 15-23), which can be achieved using a combination of polar and non-polar surfactants. Polar surfactants with high HLB's have been utilized to enable microemulsion formation, while inclusion of a non-polar surfactant (HLB<8) such as medium chain mono/diglycerides can also improve miscibility with oils. These pre-concentrates can be administered in softgels, hardgels, or adsorbed on to inert inorganic or organic polymers to generate free flowing powders. The powder can be compressed into tablets, filled into hard gelatin capsules or formulated into other oral dosage forms known to the art. Alternatively, the pre-concentrates can be formulated for parenteral, intramuscular, transdermal, nasal, sublingual, buccal and subcutaneous administration.

As described herein, formulations containing solubilizers enhance bioavailability of the therapeutic agent by their solubilization action. Under fasted conditions, a solubilizing species present in the intestinal contents comprise low concentrations of bile salt, phospholipids and cholesterol derived from fasted biliary output. In the absence of exogenous lipids the solubilization capacity of the fasted small intestine remains low and is correlated with the total bile salt concentrations rather than reflecting the structure of the individual colloidal species (Pendersen et al., Pharm Res. 17, 891-894, 2000; Kaukonen et. al., Pharm Res. 21, 245-253, 2004). Following the addition of lipids that are representative of the digestion products of exogenously derived (from lipid-based formulation or food) lipids, the drug solubilization capacity increases significantly and is dependent on the nature of the digestion products (in terms of the fatty-acid chain length) and the characteristics of the colloidal structures they form. For example, the digestion products of medium-chain triglycerides ($C_8$-$C_{12}$ fatty acids and monoglycerides) are amphiphilic and readily combine with endogenous bile salt, phosphlipid and cholesterol to provide highly dispersed, optically clear dispersions (even at high (~150 mM) lipid loads). The drug solubilization capacity of these composite colloidal species can be up to 50-fold higher than that of endogenous bile salt, phospholipids and cholesterol species (Kosenna et al., J. Pharm Sci. 93, 332-348, 2004).

However, the solubilization capacity is dependent on lipid concentration, and the solubility of a range of poorly water-soluble drugs has been shown to be enhanced by less than threefold at lower (<25 mM) exogenous lipid levels (Kosenna et al., J. Pharm Sci. 93, 332-348, 2004; Kosenna et al., J. Pharm. Sci. 94, 481-492, 2005). By contrast, the phase behavior and solubilization characteristics of the species formed on the intercalations of the digestion products of long-chain triglycerides (which comprise primarily $C_{18}$ lipids, e.g. palm oil, corn oil, canola oil, soybean oil, olive oil, peanut oil, sesame oil, hydrogenated vegetable oils, hydrogenated soybean oil, etc.) vary significantly when compared to medium-chain triglycerides (Kosenna et al., J. Pharm. Sci. 94, 481-492, 2005). $C_{18}$ fatty acids and monoglycerides are considerably less polar than their $C_8$ or $C_{12}$ equivalents and turbid systems that contain larger (~100 nm) vesicular species are evident even at low (>2.5 mM) lipid concentrations. Importantly, these vesicular species provide for significantly enhanced drug solubilization capacities. For example, in the presence of 8.75 mM long-chain fatty acids and 4.4 mM long-chain monoglycerides (approximately the same mass per mass quantities of lipid that led to a less than a threefold improvement in solubilization capacity for medium-chain lipids) solubilization enhancements of up to 20-fold are apparent (Kosenna et al., J. Pharm Sci. 93, 332-348, 2004; Kosenna et al., J. Pharm. Sci. 94, 481-492, 2005). These solubilization differences, which are based on lipid content, are particularly significant in the context of the likely luminal concentration of lipid obtained after oral administration of a lipid-based formulation. For example, assuming a lipid dose of 750 mg long-chain triglyceride and complete digestion, the maximal luminal concentrations of fatty acid and monoglyceride (solubilized in micelles) post-digestion are approximately 8.5 mM and 4.2 mM, respectively.

In contrast to micronized testosterone compositions, the present formulations do not require a separate in vivo step for the dissolution of crystalline testosterone undecanoate since a significant fraction of TU is already solubilized in the compositions by the included solubilizer.

Accordingly, the invention in various embodiments provides a formulation for administration of a therapeutic agent, including 1) one or more lipophilic, poorly water soluble therapeutic agents, 2) a sterol or ester thereof; and 3) a solubilizing agent effective for solubilization of the therapeutic agent. In a particular embodiment, the therapeutic agent is an androgen, and in a more particular embodiment, the androgen is selected from testosterone and testosterone esters, such as testosterone undecanoate. In a preferred embodiment the sterol or ester thereof is a phytosterol. In another embodiment the solubilizing agent is a non-sterol solubilizing agent.

In another embodiment the invention provides a method of enhancing solubility of one or more poorly water soluble therapeutic agents, including combining 1) a phytosterol or phytosterol ester, 2) a non-sterol solubilizing agent effective for solubilization of the therapeutic agent, and 3) at least one lipophilic, poorly water soluble therapeutic agent, to form a composition, wherein the composition is effective to enhance solubility of the at least one therapeutic agent, as compared to the solubility of the same therapeutic agent in the absence of 1) a phytosterol or phytosterol ester and 2) a non-sterol solubilizing agent effective for solubilization.

In other embodiments of the present invention, methods and compositions for enhancing the absorption and metabolic stability of testosterone or testosterone undecanoate by incorporating components that may biochemically modulate (1) T or TU absorption, (2) T or TU metabolism, and/or (3) metabolism of TU to DHTU. For example, TU is absorbed almost exclusively via the intestinal lymphatics (Coert et al., Acta Endocrinol (Copenh), 789-800, 1975; Nieschlag et al., Acta Endocrinol (Copenh), 366-374, 1975; Horst et al., Klin Wochenschr, 875-879, 1976; Shackleford J. Pharmacol. and Exp. Ther., 925-933, 2003) thereby bypassing hepatic metabolism. Formulations containing oleic acid, glycerol monooleate, Polyoxyl 40 Hydrogenated Castor Oil (e.g., Cremophore RH 40), Polysorbate 80 (e.g., Tween 80), and phytosterols (Formulation #54) enhance lymphatic absorption relative to the Castor oil and Lauroyl glycol (Andriol Testocap®) formulation by 294%. Cremophore RH 40, Tween 80, and Solutol HS 15 are known PgP efflux and P450 inhibitors. Tween 80 is also a known chylomicron secretion inducer. By using appropriate ratios of Cremophore RH 40, and Tween 80, metabolic stability and lymphatic absorption of TU can be enhanced to achieve the desired PK profile. In one embodiment the formulation contains Polyoxyl 40 Hydrogenated Castor Oil (e.g., Cremophore RH 40) and Polysorbate 80 (e.g., Tween 80) in a ratio of about 1:10 to about 10:1, more preferably about 1:2 to about 2:1.

Other components that can enhance TU absorption and metabolic stability include natural (e.g., phytosterols, borage oil, gamma-linoleic acid) and synthetic inhibitors (e.g., MK386) of 5-alpha-reductase absorbed via intestinal lymphatics. 5-alpha-reductase inhibitors such as Finasteride and Dutasteride have minimal effect on modulation of T or DHT exposure from oral T or T esters (Table 24) as they are absorbed via the portal vein.

The invention further provides a formulation for oral administration of a therapeutic agent, including 1) one or more lipophilic, poorly water soluble therapeutic agents, 2) a sterol or ester thereof; 3) a solubilizing agent effective for solubilization of the therapeutic agent; and 4) an enhancing agent. In a particular embodiment, the therapeutic agent is an androgen, and in a more particular embodiment, the androgen is selected from testosterone and testosterone esters, such as testosterone undecanoate. In a preferred embodiment the sterol or ester thereof is a phytosterol. In another embodiment the solubilizing agent is a non-sterol solubilizing agent. In a further embodiment the formulation comprises an enhancing agent. In a particular embodiment the enhancing agent is selected from the group consisting of: an inhibitor of 5-α-reductase enzymes, a P450 inhibitor, a PgP inhibitor and a chylomicron secretion inducer. In a further embodiment the 5-α-reductase inhibitor is MK-386, phytosterols, borage oil, or gamma-linoleic acid; the P450 and/or PgP inhibitors are selected from peppermint oil, Cremophore RH 40, Tween-80, and Solutol HS 15; and the chylomicron secretion inducer is Tween 80.

In another embodiment the invention provides a method of enhancing biological absorption and/or metabolic stability of one or more poorly water soluble therapeutic agents, including administering: 1) a sterol or ester thereof; 2) a non-sterol solubilizing agent effective for solubilization of the therapeutic agent; 3) an enhancing agent effective to improve the biological absorption and/or metabolic stability of at least one therapeutic agent; and 4) at least one lipophilic, poorly water soluble therapeutic agent, to form a composition, wherein the composition is effective to enhance biological absorption and/or metabolic stability of at least one therapeutic agent, as compared to correspondingly administered therapeutic in the absence of 1) a sterol or ester thereof; 2) a non-sterol solubilizing agent; and 3) an enhancing agent.

In a further embodiment the invention provides a formulation consisting essentially of a therapeutic agent and an enhancing agent effective to improve the biological absorption and/or metabolic stability of the therapeutic agent. In a particular embodiment the enhancing agent is selected from Cremophore RH 40, Tween-80, phytosterols and phytosterol esters.

The formulations of the invention make use of the advantages of oral administration of androgens, especially of testosterone and the esters thereof, by exploiting the different pharmacokinetics of the various testosterone esters in combination with phytosterols and/or phytosterol esters, so as to be able, by careful selection of appropriate dosages and esters, to attain a desired drug profile. Particularly, the invention is advantageous for administration of androgens having high first-pass effect and low bioavailability. Formulations of the invention may include further additives to achieve a cumulative or additional therapeutic effect.

Examples of such further additives may include, but are not limited to lipids, bile salts, 5-α-reductase inhibitors and any other additives effective in increasing the bioavailability of the therapeutic agent, maximizing absorption of the therapeutic agent, treating additional conditions and/or reducing side effects of drug administration, e.g. inflammation. Classes of additives that may be present in the compositions, include, but are not limited to, absorbents, acids, adjuvants, anticaking agent, glidants, antitacking agents, antifoamers, anticoagulants, antimicrobials, antioxidants, antiphlogistics, astringents, antiseptics, bases, binders, chelating agents, sequestrants, coagulants, coating agents, colorants, dyes, pigments, compatiblizers, complexing agents, softeners, crystal growth regulators, denaturants, dessicants, drying agents, dehydrating agents, diluents, dispersants, emollients, emulsifiers, encapsulants, enzymes, fillers, extenders, flavor masking agents, flavorants, fragrances, gelling agents, hardeners, stiffening agents, humectants, lubricants, moisturizers, bufferants, pH control agents, plasticizers, soothing agents, demulcents, retarding agents, spreading agents, stabilizers, suspending agents, sweeteners, disintegrants, thickening agents, consistency regulators, surfactants, opacifiers, polymers, preservatives, antigellants, rheology control agents, UV absorbers, tonicifiers and viscomodulators. The formulation may include one or more additives.

Examples of lipids that may be included as additives to a basic formulation of the invention include, but are not limited to essential fatty acids. Essential Fatty Acids (EFAs) are necessary fats that humans cannot synthesize, and must be obtained through diet. EFAs are long-chain polyunsaturated fatty acids derived from linolenic, linoleic, and oleic acids. There are two families of EFAs: omega-3 and omega-6. Omega-9 is necessary yet "non-essential" because the body can manufacture a modest amount on its own, provided essential EFAs are present. The number following the "omega-" prefix represents the position of the first double bond, counting from the terminal methyl group on the molecule. Omega-3 fatty acids are derived from linolenic acid, omega-6 from linoleic acid, and omega-9 from oleic acid.

Alpha linolenic acid (ALA) is the principal omega-3 fatty acid, which a healthy human will convert into eicosapentaenoic acid (EPA), and later into docosahexaenoic acid (DHA). EPA and the gamma linolenic acid (GLA) synthesized from linoleic (omega-6) acid are later converted into hormone-like compounds known as eicosanoids, which aid in many bodily functions including vital organ function and intracellular activity. Linoleic acid is the primary omega-6 fatty acid. A healthy human with good nutrition will convert linoleic acid into GLA.

Therefore, in another embodiment, the formulation further includes one or more triglycerides containing fatty acids, including, but not limited to, omega-3, omega-6 and omega-9.

It is known that oral TU treatment elevates dihydrotestosterone (DHT), which may be associated with an increased risk of acne, male pattern baldness and prostate hyperplasia. Co-administration of a 5-α-reductase inhibitor, such as Finasteride or Dutasteride has been shown to prevent reduction of testosterone to DHT. Commercial preparations of Finasteride and Dutasteride are known, e.g. Proscar®, Propecia®, and Avodart®.

The present inventor observed that when 5-α-reductase inhibitors Finasteride and Dutasteride are first dosed for 3 days in dogs to completely inhibit the 5-α-reductase enzyme known to reduce testosterone to DHT, followed by co-dosing with TU and Finasteride or Dutasteride, there was no significant change in the testosterone or DHT levels. This is contrary to published reports and patents issued claiming that Finasteride and Dutasteride inhibit conversion of testosterone or testosterone esters to DHT (Amory & Bremner, *J Clin Endocrinol Metab,* 2610-2617, 2005; Amory et al., *J Androl,* 72-78, 2006; U.S. Pat. No. 7,138,389; U.S. Patent Application No. 2008/0317844). TU is absorbed almost exclusively via the intestinal lymphatics (Coert et al., *Acta Endocrinol* (Copenh), 789-800, 1975; Nieschlag et al., *Acta Endocrinol* (Copenh), 366-374, 1975; Horst et al., *Klin Wochenschr,* 875-879, 1976; Shackleford *J. Pharmacol. and Exp. Ther.,* 925-933, 2003), thereby bypassing hepatic metabolism. For reasons of the dependence on lymphatic absorption, oral TU must be ingested with a meal containing some fat to allow for its optimal absorption and the attainment of serum testosterone concentrations within the normal range of adult men (Houwing et al., *Pharmacotherapy,* 1257-1265, 2003; Schnabel et al., *Clin Endocrinol,* 579-585, 2007). Once TU is absorbed into the intestinal lymphatics, a portion of TU is acted upon by 5-α-reductase to form dihydrotestosterone undecanoate (DHTU) (Horst et al., *Klin Wochenschr,* 875-879, 1976). After the TU and DHTU are released into circulation, non-specific plasma esterases enzymatically cleave the undecanoate ester resulting in the liberation of testosterone and DHT in the serum (FIGS. 7 and 8). The dog study demonstrates that the pharmacokinetics of orally dosed TU is not improved by the concomitant administration of the 5-α-reductase inhibitor Finasteride or Dutasteride. This finding is in sharp contrast to published work demonstrating that the concomitant administration of either Finasteride or Dutasteride significantly increased serum testosterone concentrations and significantly suppressed serum DHT concentrations when used in combination with oral testosterone in oil (Amory & Bremner, *J Clin Endocrinol Metab,* 2610-2617, 2005; Amory et al., *J Androl,* 72-78, 2006).

It therefore appears that oral TU is absorbed via intestinal lymphatics (Coert et al., *Acta Endocrinol* (Copenh), 789-800, 1975; Nieschlag et al., *Acta Endocrinol* (Copenh), 366-374, 1975), whereas the oral formulations of non-esterified testosterone are absorbed via the portal circulation (Amory & Bremner, *J Clin Endocrinol Metab,* 2610-2617, 2005). Finasteride and Duteseride are also absorbed via the portal circulation (Carlin et al., *Drug Metabol Dispos,* 148-155, 1992; Branson et al., *J. pharmacol & Exp Ther,* 1496-1502, 1997), and their absorption is not thought to be affected by food (Steiner et al., *Clin Pharmacokinet,* 16-27, 1996). Therefore, Finasteride and Dutasteride may not be able to prevent the 5-α-reduction of the oral TU because of the different routes of absorption and appearance in the systemic circulation. Consistent with this hypothesis is the work of Horst et al., *Klin Wochenschr,* 875-879 (1976), that demonstrated the presence of significant amounts of DHTU in the thoracic ducts of men dosed orally with TU while their thoracic ducts were cannulated during neck surgery. In connection with this hypothesism the inventor theorized that 5-α-reductase inhibitors with proven absorption via the intestinal lymphatics, such as MK-386 (Gloria et al., *Int. J. of Pharmaceutics,* 37-44, 1998), may be successful in suppressing the elevations in serum DHT observed with dosing of oral TU.

As will be recognized by those skilled in the art, the amount or percentage of the therapeutic agent present in the formulation and dosage forms will vary. Thus, for example, the amount of therapeutic agent is based, in part, upon the actual need of the patient and can be determined by the attending clinician. In all cases, however, the amount of the therapeutic agent present in the composition and dosage forms is an amount such that the therapeutic agent is significantly solubilized in the appropriately selected solubilizer or solubilizers so that the aforementioned advantages of the present invention are achieved. In a particular embodiment the amount or percentage of all elements of a formulation of the invention are optimized to achieve a desired level of total serum testosterone in a subject in the range of from about 300 to about 1100 ng/dL in a male subject, and about 30 to about 110 ng/dL in a female subject, over a time period of about 8 hours to about 24 hours.

The terms "effective amount" or "therapeutically effective amount" as used herein refer to a nontoxic but sufficient amount of the therapeutic agent to provide the desired therapeutic effect within a subject. The exact amount that is "effective" will vary from subject to subject, depending on the age, weight and general condition of the subject, the severity of the condition being treated, the judgment of the clinician, and the like. However, an appropriate "effective amount" in any individual case can be determined by one of ordinary skill in the art using only routine experimentation, based on the disclosure herein.

Preferably, the formulations are prepared so as to contain a sufficient amount, i.e., dose of TU within a dosage unit, e.g., a capsule. It is preferred that the amount of testosterone will be present in the formulation so as to provide each dosage form with a unit dosage of from about 1 to about 1000 mg, and preferably about 40 to about 400 mg of testosterone undecanoate for oral administration, and preferably from 200 to 1000 mg for parenteral. Typically the testosterone and/or testosterone ester is from about 0.1% to about 80% of the formulation by weight. Preferably, the testosterone and/or testosterone ester is from about 0.1% to about 50% of the formulation by weight. More preferably, the testosterone and/or testosterone ester is from about 0.1% to about 40% of the formulation by weight. In various other embodiments, the testosterone and/or testosterone ester may be in a range having a lower value of any of 0.01, 0.05, 0.1, 0.15, 0.2, 0.5 and 1%, and having an upper value of any of 70.5, 71.0, 71.25, 71.5, 71.75, 72.0, 73.0, 74.0, 75.0, 77.5, 79.0, 79.5, 79.75, 79.9, 79.95 and 80.0%.

In one embodiment, it is particularly preferred that the entire amount of TU is solubilized in the composition. However, it is sometimes necessary to add additional TU in non-solubilized form when the TU solubility capacity of a given composition is exceeded. Therefore, it is also an important feature of the present invention that the TU present in the composition is significantly solubilized. Typically, at least about 20% of the TU is solubilized in the composition and preferably at least about 50% of the TU is solubilized in the composition of the dosage form. The dosage form contains TU solubilized in the composition in an amount of at least about 1 mg, preferably in an amount of at least about 40 mg, and more preferably in an amount of at least about 100 mg.

Although the formulation may be administered to a subject in any suitable dosage form, the dosage form is preferably a capsule or other oral dose form (e.g., a tablet, lozenge, etc.) containing the formulation having a therapeutically effective amount of testosterone and/or testosterone undecanoate contained therein. In an additional embodiment, the dosage form is preferably a formulation suitable for parenteral administration, e.g. an intra-muscular injection.

The amount of solubilizer that can be included in a formulation of the present invention is not particularly limited. When the formulation is administered to a subject, however, the amount of any given solubilizer is limited to a bio-acceptable amount. Bio-acceptable amounts of solubilizers and other components are readily determined by one of skill in the art by using routine experimentation or searching the literature. In some circumstances, it may be advantageous to include amounts of solubilizers far in excess of bio-acceptable amounts, for example, to maximize the concentration of the TU, with excess solubilizer removed prior to providing the composition to a patient. Excess solubilizer may be removed using conventional techniques such as distillation, spray drying, lyophilization or evaporation. Generally, the amount of solubilizer in the composition will be from about 10% to about 90%, preferably between about 12.5% to about 85% by weight. In various other embodiments, the solubilizer may be in a range having a lower value of any of 0.01, 9.05, 9.1, 9.15, 9.2, 9.5 and 10%, and having an upper value of any of 80.5, 81.0, 81.25, 81.5, 81.75, 82.0, 83.0, 84.0, 85.0, 87.5, 89.0, 89.5, 89.75, 89.9, 89.95 and 90.0%.

In one embodiment, the formulation also contains 1% to 99% by weight of a sterol and/or sterol ester. In a preferred embodiment the formulation contains about 1% to about 90% of phytosterol and/or phytosterol esters, solubilized and/or suspended. Preferably, the formulation contains from about 1% to about 70% of phytosterols and/or phytosterol esters; more preferably, the formulation contains from about 1% to about 45% of phytosterols and/or phytosterol esters. In a more preferred embodiment, the formulation contains about 2% to about 20% solubilized phytosterols or phytosterol esters. In a further embodiment, additional phytosterols or phytosterol esters may be co-dosed with a formulation of the invention. In various other embodiments, the total phytosterol and/or phytosterol esters, solubilized and/or suspended may be in a range having a lower value of any of 0.01, 0.05, 0.1, 0.15, 0.2, 0.5 and 1%, and having an upper value of any of 80.5, 81.0, 81.25, 81.5, 81.75, 82.0, 83.0, 84.0, 85.0, 87.5, 89.0, 89.5, 89.75, 89.9, 89.95 and 90.0%.

In a further embodiment of the invention, phytosterols or phytosterol esters may be added with the therapeutic agent in solubilized form, in suspended form, as an additive, as a co-dose accompanying dosing of a formulation of the invention, or any combination thereof.

The amount of additional components in a formulation of the invention can be determined by one of ordinary skill in the art, according to the desired property or properties to be imparted to the composition. For example, the amount of a suspending agent may be determined by adding gradual amounts of the agent until the desired homogeneity of un-dissolved drug particles in the composition is achieved. For a colorant, the amount of the colorant may determined by adding small amounts of the colorant until the desired color of the composition is achieved. For a surfactant, the amount of a surfactant may determined by adding gradual amounts of the surfactant until the desired wetting effect or dispersibility of the composition is achieved. The amount of surfactant, when present, in the composition will generally be up to about 80 wt. %, preferably between about 1 wt. % to about 50 wt. %, more preferably between 1 wt. % to about 35 wt. %.

In a particular embodiment, the invention provides a formulation containing a therapeutically effective amount of a hydrophobic drug, a phytosterol and/or phytosterol ester, and a LCPUFA, LCPUFA oils, LCPUFA esters or mixtures thereof. The hydrophobic drug is present in an amount of from about 0.1 to 70% w/w of the composition. Furthermore, the hydrophobic drug is at least about 20% solubilized in the composition. The LCPUFA substance in the composition is present in an amount of from about 1 to 99% w/w of said composition. The phytosterols and/or phytosterol esters are suspended in the formulation in an amount of from 1% to 40%.

In a further embodiment, a formulation of the invention may be provided as a pharmaceutical composition. As such, the formulation is provided in a dosage form, for administration to a subject in need of such formulation.

Administration of a formulation of the invention may be as a single composition, or as multiple compositions. The formulations and compositions thereof maybe administered at the same time or may be administered at different times. Administration may be performed by any method which results in the desired serum concentration of therapeutic agent.

In a preferred embodiment, the pharmaceutical composition is present in a single dosage form. The dosage form(s) are not limited with respect to size, shape or general configuration, and may comprise, for example, a capsule, a tablet or a caplet, or a plurality of granules, beads, powders or pellets that may or may not be encapsulated. A preferred dosage form is a capsule containing a composition as described herein (FIG. 1). The capsule material may be either hard or soft and is generally made of a suitable compound such as gelatin, starch or a cellulosic material. As is known in the art, use of soft gelatin capsules places a number of limitations on the compositions that can be encapsulated. See, for example, Ebert (1978), "Soft Elastic Gelatin Capsules: A Unique Dosage Form," *Pharmaceutical Technology* 1(5). Two-piece hard gelatin capsules are preferably sealed, such as with gelatin bands or the like. See, for example, *Remington: The Science and Practice of Pharmacy*, Twenty first Edition. (2006) cited supra, which describes materials and methods for preparing encapsulated pharmaceuticals. In this embodiment, the encapsulated composition may be liquid or semi-solid (e.g., a gel).

The formulation may optionally include a carrier, in addition to the therapeutic agent, sterol and solubilizer. In one embodiment, the carrier contains the solubilizer. In one embodiment, the carrier includes one or more solubilizers and, optionally further includes one or more pharmaceutically acceptable additives in addition to the solubilizer.

"Carrier" or "vehicle" as used herein refers to carrier materials suitable for drug administration. Carriers and vehicles useful herein include any such materials known in the art, e.g., any liquid, gel, solvent, liquid diluent, solubilizer, surfactant, or the like, which is nontoxic and which does not interact with other components of the composition in a deleterious manner.

In one embodiment of the invention, the formulation is provided in a lipid suspension as a pharmaceutical composition.

The lipids may be of animal, vegetable or mineral origin, which are substantially water-insoluble, inert, non-toxic hydrocarbon fats and oils and derivatives thereof, and may comprise any of the commonly commercially available fats or oils approved by the Food & Drug Administration. The lipid may be a liquid or a solid at room temperature. Preferably, the lipid has a melting point in the range of about 90 to 160° F. (32 to 71° C.). The lipid may comprise a vegetable oil base commonly known as hard butter. Hard butters are hydrogenated, press fractionated, or other processed oils that are processed or recombined to have a solid fat index (percent solid fat vs. temperature) similar to that of cocoa butter. However, other lipids may be used that are relatively hard or solid at room temperature, but melt rapidly in the mouth at a temperature of about 92° to 98° F. (29 to 32° C.). The lipid is employed in the amounts within the range of from about 20 to about 50%. Examples of suitable lipids include tallow, hydrogenated tallow, hydrogenated vegetable oil, almond oil, coconut oil, corn oil, cottonseed oil, fish oil, light liquid petrolatum, heavy liquid petrolatum, olein, olive oil, palm oil, peanut oil, persic oil, sesame oil, soybean oil, castor oil or safflower oil.

Additionally, stearines can be used as a lipid in the present invention. The addition of stearines to the product provides the favorable property of mold-release.

Furthermore a pharmaceutical composition of the invention may comprise a filler. Fillers of the present invention are pharmacologically inert and optionally nutritionally beneficial to humans and animals. Such fillers include cellulose such as microcrystalline cellulose, grain starches such as cornstarch, tapioca, dextrin, sugars and sugar alcohols such as sucrose, sorbitol, xylitol, mannitol and the like. Preferred fillers include non-fat milk powder, whey, grain brans such as oat bran, and fruit and vegetable pulps. Preferred fillers are finely divided and have a preferred average particle size in the range of about 0.10 to about 500 microns. The fillers are present in the drug delivery device in a concentration of about 50 to 80%. Optionally, the pharmaceutical particles can also serve as filler in the delivery system. Optionally, the filler may include sterols, particularly phytosterols. (See Example 9 for use of microcrystalline cellulose for making a solid dosage form of the present invention).

In one embodiment of the invention the therapeutic agent is microencapsulated. Such microencapsulation includes sustained release encapsulation. Any known method of encapsulation is suitable in the present invention. Such methods include, but are not limited to air coating, chemical erosion, coacervation, fluid bed coating, macroencapsulation, microencapsulation, osmosis, pan spray coating, physical erosion, polymer protein conjugate systems, and polymeric microspheres. A preferred method involves slowly blending the drug with a filming agent solution to form granulated particles. The granulated particles are allowed to dry on a tray and are sieved to the desired size, typically in the range of from about 200 to about 500 microns. The coating materials include, but are not limited to, acrylic polymers and co-polymers, alginates, calcium stearate, cellulose, including methylcellulose, ethylcellulose, and hydroxypropyl cellulose, gelatins, glyceryl behenate, glycholic acid and its various forms, ion exchange resins, lactic acid and its various forms, lipids, methacrylic monomers, methacrylic polymers and co-polymers, polyethylene glycol polymers, shellac (pharmaceutical glaze), stearic acid, glycerol esters of fatty acids and waxes. It is contemplated in the present invention that the microencapsulated testosterone and/or testosterone ester may be used alone, or in the lipid suspension. Further, the microencapsulated testosterone and/or testosterone ester may be used in any other system, such as tablets, boluses, enclosed in a gelatin capsule, or in a liquid or syrup system.

In another embodiment of the present invention, the therapeutic agent is not microencapsulated, but suspended in the lipid as dry particles. Where the therapeutic agent is a testosterone and/or testosterone ester, typically the testosterone and/or testosterone ester is present in the delivery device in a concentration of 50% or less. However, the testosterone can comprise all of the dried particles, to provide the necessary dose.

Optionally, the dry particles include flavorings that make the device taste and smell appealing to humans or animals. The flavorings can be natural or synthetic, and can include fruit flavorings, citrus, meat, chocolate, vanilla, fish, butter, milk, cream, egg or cheese. The flavorings are typically present in the device in the range of about 0.05 to about 1.0%.

The delivery device may also include other pharmaceutically acceptable agents, such as sweetening agents, including hydrogenated starch hydrolysates, synthetic sweeteners such as sorbitol, xylitol, saccharin salts, L-aspartyl-L-phenylalanine methyl ester, as well as coloring agents, other binding agents, lubricants, such as calcium stearate, stearic acid, magnesium stearate, antioxidants such as butylated hydroxy toluene, antiflatulants such as simethicone and the like.

Optionally, rupturing agents are used to rapidly deliver the testosterone and/or testosterone ester into the recipient's system. A typical rupturing agent is a starch that swells in the presence of water. Various modified starches, such as carboxymethyl starch, currently marketed under the trade name Explotab or Primojel are used as rupturing agents. A preferred rupturing agent is sodium starch glycolate. When ingested, the capsule or pellet swells in the presence of gastric juices and ruptures.

In one embodiment of the present invention, the rupturing agent is present with the therapeutic agent inside the microcapsule. As water penetrates the microcapsule, it swells the starch and ruptures the capsule, rapidly delivering the testosterone undecanoate to the system. Additional rupturing agents are disclosed in U.S. Pat. No. 5,567,439, which is hereby incorporated by reference.

In another embodiment, the rupturing agent is present in the lipid suspension, which ruptures the pellet, but leaves the microcapsules intact. This allows delayed delivery of the drug farther along in the digestive system, or in the intestines. The present invention is particularly effective in this embodiment, in that the ingested pellet may be chewable, where the pellet cleaves in the lipid suspension when chewed, but leaves the microcapsules intact. Tablets or gel capsules, when chewed, typically result in damage to or rupturing of the microcapsules defeating the effectiveness of the microcapsules.

In yet another embodiment, multiple drugs have multiple encapsulations, each containing a rupturing agent. The filming agents used for encapsulation are selected to disintegrate at selected pH conditions, which rupture and release each drug at desired locations in the digestive system.

The formulations of the present invention are prepared by conventional methods well known to those skilled in the art. The formulation can be prepared by mixing the active agent, the solubilizer, and optional additive according to methods well known in the art. Excess solvent or solubilizer, added to facilitate solubilization of the active agent and/or mixing of the formulation components, can be removed before administration of the pharmaceutical dosage form. The compositions can be further processed according to conventional processes known to those skilled in the art, such as lyophilization, encapsulation, compression, melting, extrusion, balling, drying, chilling, molding, spraying, spray congealing, coating, comminution, mixing, homogenization, sonication, cryopelletization, spheronization and granulation to produce the desired dosage form.

For dosage forms substantially free of water, i.e., when the composition is provided in a pre-concentrated form for administration or for later dispersion in an aqueous system, the composition is prepared by simple mixing of the components to form a pre-concentrate. The compositions comprising solubilized TU can be further formulated into desirable dosage forms utilizing skills well known in the art. For example, compositions in liquid or semi-solid form can be filled into soft gelatin capsules using appropriate filling machines. Alternatively, the composition can also be sprayed, granulated or coated onto a substrate to become a powder, granule or bead that can be further encapsulated or tableted or molded if the compositions solidify at room temperature with or without the addition of appropriate solidifying or binding agents. This approach allows for the creation of a "fused mixture," a "solid solution" or a "eutectic mixture."

For example, testosterone undecanoate and phytosterols form a eutectic mixture when the ratio of TU:phytosterols is 80:20. The melting point of the eutectic is 54° C. while the melting points of TU and phytosterols are 60° C. and 137° C., respectively. The dissolution profile of the eutectic is shown in FIG. 2.

Figure 2:
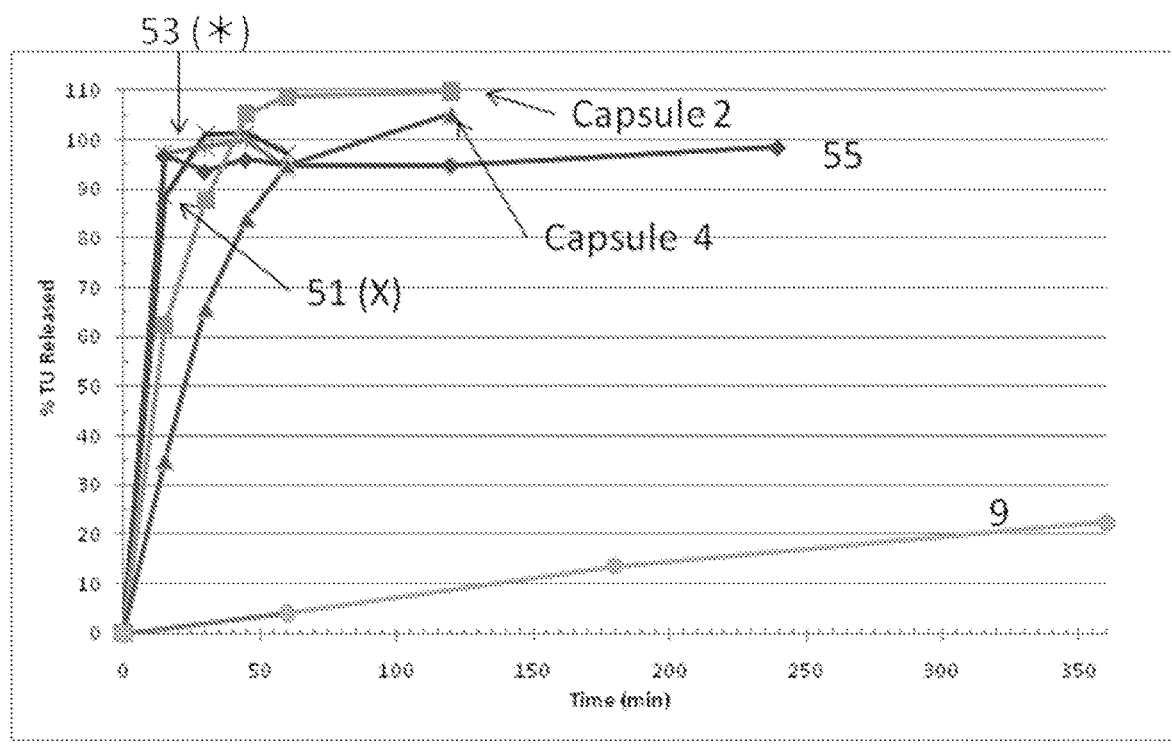
FIG. 2 shows dissolution curves of testosterone undecanoate Formulations 9 (Table 2), 51, 53 and 55 (Table 20), as compared to known preparations described in Example 1 of US2010/0173882.

FIG. 2 provides the dissolution profiles of each of Formulations 9, 51, 53, and 55, as set forth in Tables 2 and 20 herein and Capsules 2 and 4 from Example 1 of US2010/0173882. The data were obtained in a dissolution medium incorporating 2% TritonX-100 as a surfactant in the USP 2 apparatus in accordance with the present invention. The dissolution profiles of formulations in the present invention are clearly different from those in US2010/0173882. Formulations 51, 53 and 55 were used in the human clinical study described in Example 8.

Figure 4:
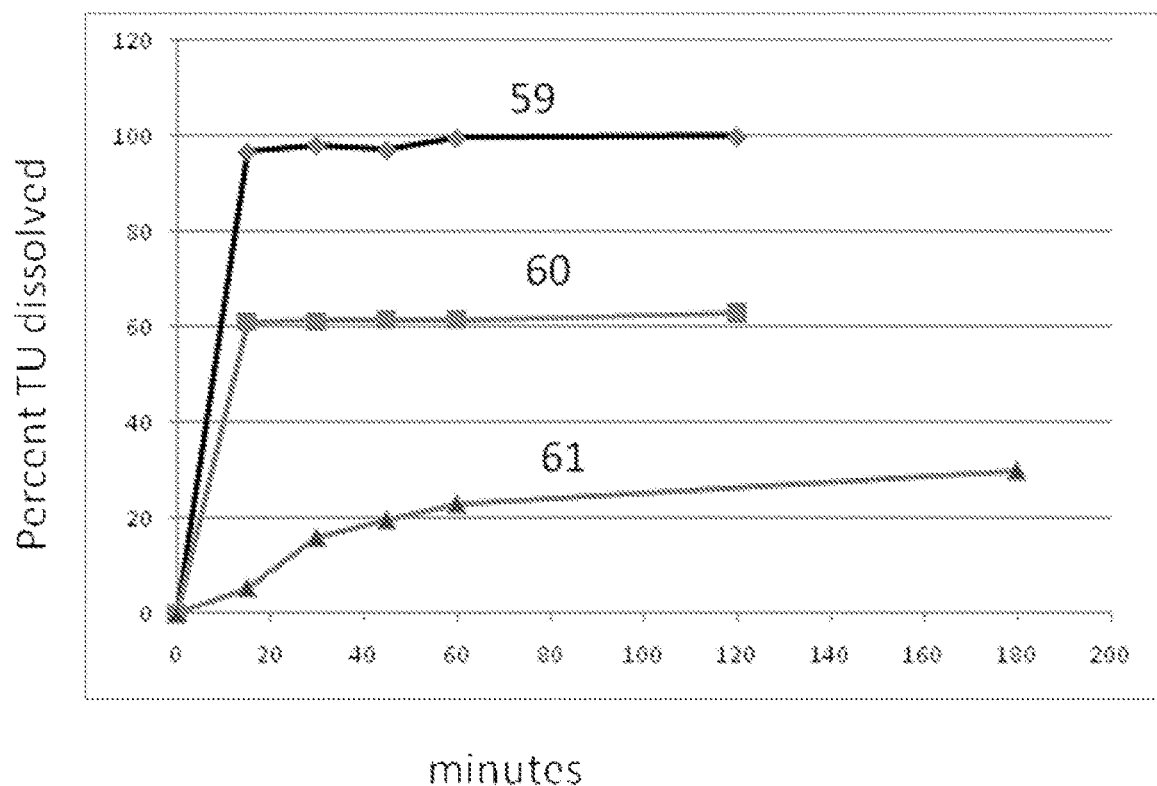
FIG. 4 shows dissolution curves of testosterone undecanoate from formulations 59, 60, and 61 (Table 22).

Not previously identified is an effect observed in FIG. 4 depicting the dissolution profile of a formulation saturated with phytosterols (Formulation 59) and one in which excess phytosterols have been added to form a waxy solid (Formulation 61) that the concentration of phytosterols may be used to modulate the dissolution profile of formulations containing phytosterols. The dissolution profiles of FIGS. 2 and 4 illustrate that at higher concentrations phytosterols function to retard the dissolution of the therapeutic agent (FIG. 4).

FIG. 4 provides dissolution curves of TU from formulations 59, 60, and 61 (Table 22). Dissolution was measured in 900 mL of 25 mM phosphate buffer at pH 7.0 containing 0.1% SLS, obtained at 200 rpm using USP 2 apparatus. Formulation 59 illustrates the dissolution of a formulation with the properties of remaining a liquid a room temperature, while Formulation 60 is a suitable formulation which is solid at room temperature. Phytosterols in excess of the amount soluble at 70° C. may be added to the composition to modulate the release rate, as illustrated by the dissolution profile of Formulation 61 in FIG. 4. Formulation 61 further has the desirable property of being a sufficiently hard material that it may be reduced to a powder, which is fillable into a capsule by ordinary means.

As previously indicated, the compositions may include additional amounts of T or TU over the amount that is solubilized in the composition. In such a case, TU can be partially suspended in the composition. Such partially solubilized and partially suspended TU compositions can be prepared by adding solids of T or TU of desired form and particle size. For example, micronized crystalline T or TU having an average particle size of less than 30 microns, nanosized crystalline T or TU having an average particle size of less than 1 micron or amorphous T or TU may be added to the composition. Such micronized or nanosized T and TU particles can be obtained by precipitation or size reduction techniques well-known in the art. In addition, partially suspended T and/or TU compositions may be obtained from a supersaturated T or TU solution or by co-precipitation with an additive from a T and/or TU solution.

It is particularly preferred that an orally administered drug delivery system be prepared by first embedding the therapeutic agent(s) into phytosterols and/or phytosterol esters and an organic polymer, separately or together, in a solid state as obtained by suspension or use of a spray-drying process.

It is especially preferred to mix the testosterone products with other auxiliary agents, binders, fillers, lubricants, surfactants or disintegration accelerators and to compress or mold the mixture into tablets or fill into a capsule.

When testosterone and testosterone esters are employed along with phytosterols and/or phytosterol esters, the use of the embedding technique of spray-drying in organic polymers (polyvinylpyrrolidone, hydroxypropylmethylcellulose and its derivatives, solid polyethylene glycols), the solubility of the testosterone and testosterone esters in the intestinal fluids is enhanced.

In one embodiment, a formulation of the invention is made by dissolving testosterone and/or the particular testosterone ester, phytosterols and/or phytosterol esters together with the polymer (for example polyvinylpyrrolidone or hydroxypropyl-methylcellulose and its derivatives) in ethanol and processing the mixtures further in a spray-drying unit to form an amorphous, embedded, spray-dried formulation. It is possible in this case 1) to embed said active ingredients separately from each other or 2) to embed them together in a single processing step, to obtain an amorphous mixture.

In another embodiment, a formulation of the invention is made by suspending crystalline or amorphous testosterone and/or the particular testosterone ester, phytosterols and/or phytosterol esters in a lipid based formulation containing one or more surfactants resulting in SEDDS or SMEDDS.

The fine-particle embedded spray-dried material or the SEDDS or the SMEDDS is then subjected to dry mixing with other auxiliary agents for making tablets or capsules. The mixture is then compressed into tablets or filled into capsules.

In order to obtain a formulation with the desired release patterns, it is advantageous to individually consider characteristics of the individual components of the formulation, such as dosage of the active ingredient, ratio of testosterone to testosterone esters, selection of the ester or of the chain length at C-17 position of the androgen moiety, level of phytosterols and/or phytosterol esters, length of fatty acid chain and unsaturation level of lipids, level of surfactants, and level of sustained release polymer.

An exemplary optimized formulation is a short-acting testosterone with testosterone undecanoate (eleven-carbon chain) which has a longer half-life.

By skillful combination of testosterone with testosterone esters, in an immediate release and sustained release formulation, it is possible to attain blood level patterns which are capable of recreating or simulating the body's own rhythmicity of endogenous testosterone levels.

Figure 10:
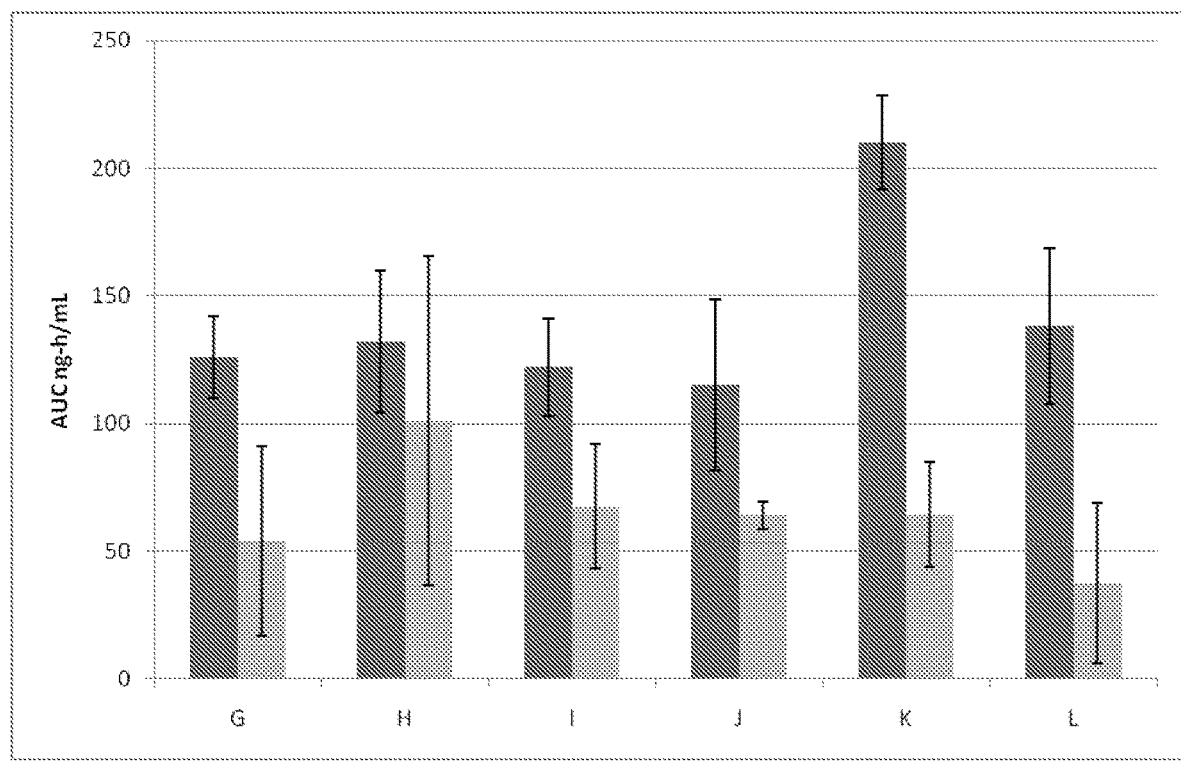
FIG. 10 shows the average testosterone and DHT exposures (ng-h/mL) for a study of 6 treatments G-L each containing 80 mg TU, as provided in Example 5.

The present inventor has shown that by the administration of testosterone and/or testosterone undecanoate and phytosterol and/or phytosterol esters, it is possible to increase lymphatic absorption of testosterone undecanoate and modulate levels of T and DHT (FIG. 10). In selecting the testosterone ester, the choice can be made specifically from three groups: 1) esters of shorter chain length (for example, testosterone acetate or propionate), 2) esters of medium chain length (for example testosterone enanthate, cypionate or cyclohexanecarboxylate) and 3) esters of higher chain length (for example testosterone undecanoate, bucyclate or palmitate).

In another embodiment, the process for preparing the composition including the formulation in a delivery system containing a lipid comprises melting the lipid, phytosterols and/or phytosterol esters and mixing with the surfactant. The dry particles of the active substance are mixed with the melted lipid/phytosterol mixture to form a suspension exhibiting pseudoplastic and/or thixotropic flow properties, and poured or molded to provide solid dosage forms (FIG. 1).

The dry particles, which include the testosterone and/or testosterone ester, filler and optional flavorings and additives, are pre-blended and typically have a particle size in the range of from about 50 microns to about 250 microns. The pre-blended particles are gradually added to the heated lipid base containing phytosterols and/or phytosterol esters until a high solids suspension is obtained, typically in the range of about 50% to about 80% particles and from about 50% to about 20% lipid.

Slow addition of the dry particles is critical in the production of the device, to ensure that the particles are suspended in their micronized state and not as agglomerated clumps. Moreover, rapid addition can cause the mixing process to fail in that the melted suspension will not have the desired flow properties, but instead will be a granular oily mass (a sign of product failure). The mixing step is accomplished in a heated mixing device that insures thorough mixing of all materials with minimal shear, such as a planetary mixer or a scrape surface mixer. After the suspension is formed, the product is poured into molds and allowed to cool. De-molding and packaging are then performed. Alternatively, the suspension can be super-cooled and sheeted in a semi-soft format. The sheet is processed through forming rolls containing a design or configuration that embosses and forms the final shape.

The formulations and pharmaceutical compositions of the invention are useful in methods of treatment of subjects in need of such treatment. For example, the testosterone-containing formulations and pharmaceutical compositions described herein can be administered to patients who would benefit from testosterone replacement therapy. Patients suffering from any condition, disease or disorder which can be effectively treated with testosterone can benefit from the administration of a therapeutically effective amount of the testosterone-containing compositions described herein. In particular, however, the testosterone-containing compositions are effective in treating individuals suffering from androgen deficiency (e.g., postmenopausal women, menopausal women, sexually dysfunctional women, andropausal men, hypogonadal men, erectile dysfunctional men and the like).

In one embodiment the invention provides a method of treating a condition comprising administering: a) at least one lipophilic, poorly water soluble therapeutic agent; b) a phytosterol or phytosterol ester; c) a non-sterol solubilizing agent effective for solubilization of the at least one therapeutic agent; and d) an enhancing agent effective to enhance the biological absorption and/or metabolic stability of the at least one therapeutic agent. In a particular embodiment, the therapeutic agent is an androgen, and in a more particular embodiment, the androgen is selected from testosterone and testosterone esters, such as testosterone undecanoate. In a preferred embodiment the sterol or ester thereof is a phytosterol.

In a particular embodiment the invention provides a method of treating a subject in need of treatment for erectile dysfunction wherein the method comprises administration of two therapeutic agents, a first therapeutic agent comprising an androgen and a second therapeutic agent comprising a PDE V inhibitor, including, but not limited to, tadalafil (Cialis®), sildenafil (Viagra®), and vardenafil (Levitra®).

In order to characterize the absorption and bioavailability of the formulations of the present invention, animal models can be used. As noted above, Shackleford et al studied testosterone exposure in dogs dosed with testosterone undecanoate (Shackleford et al., *J. Pharmacol. And Exptl. Therap.*, 2003, vol. 306, no. 3, pp. 925-933.) and demonstrated that TU is almost exclusively absorbed through intestinal lymphatics by-passing the liver. Canine models are generally accepted in the art as predictive of human efficacy with respect to oral administration of testosterone and its esters.

Formulations of the present invention were tested in canine models, as described in Examples 4 and 5 below, which demonstrates improved TU absorption when co-dosed with phytosterols, as compared to TU dosed from a reference formulation composition similar to that of Andriol® Testocaps® (Table 23 and 24).

The inventor has found that phytosterols have unexpectedly enhanced the solubility of testosterone and/or testosterone esters in a range of lipid-based formulations from simple one lipid solubilizer component to complex 3-5 lipid solubilizer and surfactant SEDDS and/or SMEDDS formulations from about 1% to about 40% (Tables 1-20). The formulations have been divided into various classes I through VII depending on the complexity of the formulation. These tables also provide the compositions of representative formulations of the invention along with method of making them. The solubility of testosterone undecanoate in selected fatty acids, triglycerides, mono- and diglycerides, surfactants, emulsifiers, antioxidants and co-solvents were measured to select excipients for preparing representative examples of formulation(s) for each class (Table 1). The clinical formulation was also prepared with different sterols: Phytosterols, Cholesterol, Beta-sitosterol, Sitostanol (Table 19). It was unexpectedly discovered that testosterone and testosterone undecanoate enhance each other's solubility when saturated with phytosterols (Tables 16-18).

Dosage regimens and daily dosages for testosterone can vary, as a number of factors are involved, including the age and general condition of the patient.

The present invention relates to a method of administering a combination of testosterone and/or testosterone esters, phytosterols and/or phytosterol esters, mono and polyunsaturated oils and/or esters of mono and polyunsaturated oils and/or mono and polyunsaturated fatty acids in an oral preparation so that, by finely adjusted dosing of the active ingredients with improved sustained release properties, various desired plasma levels of testosterone can be set or produced in individual patients, for example to restore an endogenous body rhythm. The testosterone, when delivered in the present invention, may provide improved sustained release properties with an improvement of 10-300% over that shown in the art using micronized/nanomilled testosterone alone or testosterone undecanoate in a commercial formulation (Andriol® Testocaps®). In the delivery system, the testosterone and testosterone esters may be delivered as a solid (capsule or tablet), liquid lipid solution, or liquid lipid suspension.

In another embodiment, the invention provides a method of administering a combination of testosterone and testosterone esters (or solely testosterone esters), phytosterols and/or phytosterol esters, mono and polyunsaturated oils and/or esters of mono and polyunsaturated oils and/or mono and polyunsaturated fatty acids in an oral preparation so that, by finely adjusted dosing of the active ingredients with immediate and/or modified release properties and targeted delivery in various regions of the GI tract, various desired plasma levels of testosterone can be set or produced in individual patients along with maintaining or controlling normal physiological levels of dihydrotestosterone (DHT).

DHT levels in eugonadal men are typically about $\frac{1}{10}^{th}$ that of testosterone (i.e. about 30-110 ng/dL). Modified release dosage forms include but are not limited to those where drug release is modulated by gastric retention, muco-adhesion, time, pH, enzymes, or pressure. In this context, improved modified release properties are adjustment of release so that the amount of DHT relative to testosterone is minimized. Testosterone interacts with receptive androgen receptors either directly or following its conversion to DHT via the action of 5-alpha-reductase. DHT is a more potent androgen than testosterone and elevated DHT levels are thought by some scientists to increase the risk of benign prostate hyperplasia (BPH) and prostate cancer. Elevated levels of DHT are a noted problem with the oral or transdermal administration of testosterone and/or testosterone esters.

In one embodiment the invention provides a method of maintaining or controlling physiological levels of DHT in a subject in need of testosterone replacement such that the physiological levels of DHT are normal or near normal and supra-physiological levels of DHT are avoided by such control or maintenance. In a particular embodiment the method for maintaining or controlling physiological levels of DHT in a subject in need of testosterone replacement comprises administration of 1) testosterone and/or testosterone undecanoate, 2) a sterol or ester thereof; 3) a non-sterol solubilizing agent effective for solubilization of the T or TU; and 4) an agent for enhancing the biological absorption and/or metabolic stability of the T or TU. In a preferred embodiment the sterol or ester thereof is a phytosterol. In a further preferred embodiment, the method results in total serum testosterone in the subject in the range of from about 300 to about 1100 ng/dL and total serum DHT in the subject in the range of from about 30 to 300 ng/dL, where the subject is a male subject. In an additionally preferred embodiment, the further embodiment the method results in total serum testosterone in the subject in the range of from about 30 to about 110 ng/dL, where the subject is a female subject.

The testosterone and/or testosterone esters, when delivered, may provide total serum testosterone in the desired range for a period of eight (8) to twelve (12) or more hours. In one embodiment, the total serum testosterone is maintained in the desired range for up to about 24 hours.

Preferably, the sterol and/or sterol esters, essential fatty acids, essential fatty acid oils, and essential fatty acid esters and therapeutic agent exert an additive or synergistic therapeutic effect or the sterols mediate negative side effects of the therapeutic agent.

The formulations and pharmaceutical compositions of the invention are further useful in methods of treatment of additional hormone deficiencies and associated effects.

Accordingly the invention provides a method of treating an androgen deficiency in a subject, where the method includes administering a pharmaceutical composition of the invention.

In various embodiments the invention provides formulations and methods including biological absorption of one or more therapeutic agents. The route of such absorption is determined by the therapeutic agent used, additional elements of the formulation and/or the method of administration. In various embodiments, the absorption comprises lymphatic absorption and/or portal absorption. In specific embodiments the absorption comprises lymphatic absorption of testosterone undecanoate.

The invention, as variously described herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the invention. The invention is described herein in various embodiments, and with reference to various features and aspects of the invention. The invention contemplates such features, aspects and embodiments in various permutations and combinations, as being within the scope of the invention. The invention may therefore be specified as comprising, consisting or consisting essentially of, any of such combinations and permutations of these specific features, aspects and embodiments, or a selected one or ones thereof.

The compositions of the invention may be further specified in specific embodiments by provisos or limitations excluding specific substituents, groups, moieties or structures, in relation to various specifications and exemplifications thereof set forth herein. Thus, the invention contemplates restrictively defined compositions, e.g., a composition excluding one or more specified ingredients.

The advantages and features of the invention are further illustrated with reference to the following examples, which are not to be construed as in any way limiting the scope of the invention but rather as illustrative of various embodiments of the invention in specific applications thereof.

Example 1

Evaluation of TU Solubility with & without Sterols in Formulations of Varying Complexity The solubility of TU in various solubilizers was determined using conventional techniques such as incrementally adding TU until the solubilizer could no longer solubilize additional material. Table 1 below lists experimentally measured solubilities of testosterone undecanoate (TU) in various excipients of interest. Formulations 1-50 below starting with simple one component to complex 4-6 components (Classes I through VII) were then prepared representing different categories of solubilizers. The solubility of TU and/or T was enhanced by sterols (phytosterols, cholesterol, sitostanol, and beta-sitosterol) by 1-40%. The extent of enhancement is governed by the properties of solubilizers, emulsifiers, and surfactants selected to form the formulation.

The formulations listed in Tables 1 to 20 were prepared by combining the excipients, except phytosterols, in the proportions given. The formulation was then completed by saturating with phytosterols and the addition of active agent to the desired level.

TABLE 1

Testosterone undecanoate (TU) solubility in various solubilizers

| Vehicle | TU Solubility (mg/g) at 37 C. |
|---|---|
| Oleic acid | 405 |
| Linoleic acid | 391 |
| Linolenic acid | 162 |
| Ricinoleic acid | 244 |
| Caprylic acid | 595 |
| Incromega E7010 (omega-3) | 247 |
| Incromega TG7010 SR (omega-3 high purity) | 225 |
| Omega-3 ethyl esters w/ antioxidant (AMRI) | 261 |
| Omega-3 ethyl esters w/o antioxidant (AMRI) | 360 |
| Crodamol IPM (isopropyl myristate) | 295 |
| Crodamol IPP (isopropyl palmitate) | 215 |
| Crodamol EO (ethyl oleate) | 221 |
| Ethyl linoleate | 230 |
| Sunflower oil | 105 |
| Safflower oil | 124 |
| Sesame oil | 138 |
| Castor oil | 218 |
| Canola oil | 167 |
| Corn oil | 243 |
| Maisine 35-1 | 93 |
| Linseed oil | 179 |
| Olive oil | 161 |
| Glyceryl trioleate (Capmul GTO) | 154 |
| Rapeseed oil | 123 |
| Soybean oil | 113 |
| Acconon CO-7 | 59 |
| Miglyol 812 | >100* |
| Capmul MCM | >100* |
| Capmul PG-8 | >100* |
| Propylene glycol monolaurate | >200* |
| Glyceryl mono and dicapylate/caprate (Imwitor 742) | 356 |
| Glyceryl monooleate or GMO (Peceol (Gattefosse)) | 323 |
| Glyceryl ricinoleate (Softigen 701) | 261 |
| Propylene glycol monocaprylate (Capryol 90, Gattefosse) | 486 |
| Labrasol | 43* |
| Labrafil M 1944 CS | 242 |
| Labrafil M 2125 CS | 257 |
| Polyglyceryl-3-dioleate (Plurol oleique CC497) | 193 |
| Polyglyceryl-3-diisostearate (Plurol diisosterique) | 173 |
| Polyglyceryl-6-dioleate (Caprol MPGO, Abitec) | 184 |
| Span 80 | 289 |
| Polysorbate 85 | 125 |
| Cremophor RH40 | 88* |
| Polysorbate 80 (Tween 80) | 39* |
| N-methyl pyrrolidone | >500 |
| Transcutol HP | 180 |
| dl-alpha-tocopherol | 527 |
| Phosal 50 PG (~50% Lecithin in PG, sunflower mono-diglycerides and ascorbyl palmitate) | 138 |

*Solubility determined at 25° C.

TABLE 2

Class I: TU + Phytosterols

| Formulation # | TU % | Phytosterols % |
|---|---|---|
| 1 | 5 | 95 |
| 2 | 10 | 90 |
| 3 | 20 | 80 |
| 4 | 30 | 70 |
| 5 | 40 | 60 |
| 6 | 50 | 50 |

TABLE 2-continued

Class I: TU + Phytosterols

| Formulation # | TU % | Phytosterols % |
|---|---|---|
| 7 | 60 | 40 |
| 8 | 70 | 30 |
| 9 | 80 | 20 |
| 10 | 90 | 10 |
| 11 | 95 | 5 |

TABLE 3

Class II: TU + 1 Lipid Solubilizer + Phytosterols

| | % Composition (w/w) Formulation # | |
|---|---|---|
| | 12 | 13 |
| Ω-3 Ethyl esters w antioxidant | 100 | |
| Oleic acid | | 100 |
| TU solubility mg/gm | 246 | 385 |
| TU solubility mg/gm saturated with phytosterols | 290 | 418 |
| Percent change in solubility | 17.9% | 8.6 |

TABLE 4

Mono/diglyceride or Polyoxylglyceride Based

| | % Composition (w/w) Formulation # | |
|---|---|---|
| | 14 | 15 |
| GMO (Peceol) | 100 | — |
| Labrafil M 1944 CS | — | 100 |
| TU solubility mg/gm | 257 | 242 |
| TU solubility mg/gm saturated with phytosterols | 317 | 275 |
| Percent change in solubility | 23.3 | 13.6 |

TABLE 5

Class III: TU + 1 Lipid Solubilizer + Surfactant + Phytosterols
Triglyceride or Fatty Acid Based

| | % Composition (w/w) Formulation # | | |
|---|---|---|---|
| | 16 | 17 | 18 |
| Corn oil | 65 | | |
| Oleic acid | | 65 | |
| Caprylic acid | | | 65 |
| Cremophor RH40 | 11.67 | 11.67 | 11.67 |
| Tween 80 | 23.33 | 23.33 | 23.33 |
| TU solubility mg/gm | 218 | 254 | 407 |
| TU solubility mg/gm w/ phytosterols | 237 | 354 | 469 |
| Percent change in solubility | 8.7% | 39.4% | 15.2% |

TABLE 6

Mono/diglyceride Based

| | % Composition (w/w) Formulation # | |
|---|---|---|
| | 19 | 20 |
| GMO (Peceol) | 65 | |
| Capryol 90 | | 65 |
| Cremophor RH40 | 11.67 | 11.67 |
| Tween 80 | 23.33 | 23.33 |
| TU solubility mg/gm | 221 | 272 |
| TU w/phytosterols | 233 | 352 |
| Percent change in solubility | 5.4% | 29.4% |

TABLE 7

Polyoxylglyceride Based

| | % Composition (w/w) Formulation # 21 |
|---|---|
| Labrafil M 2125 CS | 65 |
| Cremophor RH40 | 11.67 |
| Tween 80 | 23.33 |
| TU solubility mg/gm | 191 |
| TU solubility mg/gm w/ phytosterols | 252 |
| Percent change in solubility | 31.9% |

TABLE 8

Class IV: TU + 2 Lipid Solubilizers + Surfactant + Phytosterols
Fatty acid based

| | % Composition (w/w) Formulation # | | | |
|---|---|---|---|---|
| Table 1 | 22 | 23 | 24 | 25 |
| Oleic acid | 39.85 | 47.86 | | |
| Caprylic acid | | | 29.07 | 38.20 |
| GMO (Peceol) | 25.15 | | 35.93 | |
| Capryol 90 | | 17.14 | | 26.80 |
| Cremophor RH40 | 11.67 | 11.67 | 11.67 | 11.67 |
| Tween 80 | 23.33 | 23.33 | 23.33 | 23.33 |
| TU solubility mg/gm | 245 | 264 | 252 | 328 |
| TU solubility mg/gm s when saturated with phytosterols | 258 | 331 | 309 | 390 |
| Percent change in solubility | 5.3 | 25.4 | 22.6 | 18.9 |

TABLE 9

Class IV: TU + 2 Lipid Solubilizers + Surfactant + Phytosterols
Triglyceride based

| | % Composition (w/w) Formulation # | |
|---|---|---|
| | 26 | 27 |
| Castor oil | 40 | |
| Corn oil | | 40 |
| Labrafil M 2125 CS | 25 | 25 |
| Cremophor RH40 | 11.67 | 11.67 |
| Tween 80 | 23.33 | 23.33 |

TABLE 9-continued

Class IV: TU + 2 Lipid Solubilizers + Surfactant + Phytosterols Triglyceride based

| | % Composition (w/w) Formulation # | |
|---|---|---|
| | 26 | 27 |
| TU solubility mg/gm | 143 | 144 |
| TU solubility mg/gm w/ phytosterols | 195 | 162 |
| Percent change in solubility | 36.4 | 12.5 |

TABLE 10

Class V: TU + 3 Lipid Solubilizers + Surfactant (1 Cremophor RH40: 2 Tween 80) + Lecithin + HPMC + Phytosterols

| | % Composition (w/w) Formulation # | |
|---|---|---|
| | 28 | 29 |
| Oleic acid | 30.05 | 30.05 |
| GMO (Peceol) | 18.97 | 18.97 |
| Labrafil M 2125 CS | 14.71 | 14.71 |
| Cremophor RH40 | 11.44 | |
| Tween 80 | 22.87 | 34.31 |
| Lecithin | 0.98 | 0.98 |
| HPMC | 0.98 | 0.98 |
| TU solubility mg/gm | 263 | 240 |
| TU solubility mg/gm saturated with phytosterols | 277 | 293 |
| Percent change in solubility | 5.3 | 22.1 |

TABLE 11

| | % Composition (w/w) Formulation # | | |
|---|---|---|---|
| | 30 | 31 | 32 |
| Oleic acid | 30.05 | 30.05 | 30.05 |
| Capryol 90 | 18.97 | 18.97 | 18.97 |
| Labrafil M 2125 CS | 14.71 | 14.71 | 14.71 |
| Cremophor RH40 | 11.44 | 34.31 | |
| Tween 80 | 22.87 | | 34.31 |
| Lecithin | 0.98 | 0.98 | 0.98 |
| HPMC | 0.98 | 0.98 | 0.98 |
| TU solubility mg/gm | 238 | 231 | 240 |
| TU solubility mg/gm saturated with phytosterols | 277 | 277 | 282 |
| Percent change in solubility | 16.4 | 19.9 | 17.5 |

TABLE 12

| | % Composition (w/w) Formulation # | |
|---|---|---|
| | 33 | 34 |
| Caprylic acid | 30.05 | 30.05 |
| GMO (Peceol) | 18.97 | 18.97 |
| Labrafil M 2125 CS | 14.71 | 14.71 |
| Cremophor RH40 | 11.44 | 34.31 |
| Tween 80 | 22.87 | |
| Lecithin | 0.98 | 0.98 |
| HPMC | 0.98 | 0.98 |
| TU solubility mg/gm | 328 | 320 |

TABLE 12-continued

| | % Composition (w/w) Formulation # | |
|---|---|---|
| | 33 | 34 |
| TU solubility mg/gm saturated with phytosterols | 354 | 351 |
| Percent change in solubility | 7.9 | 9.7 |

TABLE 13

| | % Composition (w/w) Formulation # | |
|---|---|---|
| | 35 | 36 |
| Caprylic acid | 30.05 | 30.05 |
| Capryol 90 | 18.97 | 18.97 |
| Labrafil M 2125 CS | 14.71 | 14.71 |
| Cremophor RH40 | 11.44 | |
| Tween 80 | 22.87 | 34.31 |
| Lecithin | 0.98 | 0.98 |
| HPMC | 0.98 | 0.98 |
| TU solubility mg/gm | 301 | 317 |
| TU solubility mg/gm saturated with phytosterols | 319 | 340 |
| Percent change in solubility | 6.0 | 7.3 |

TABLE 14

| | % Composition (w/w) Formulation # | | |
|---|---|---|---|
| | 37 | 38 | 39 |
| Oleic acid | 45.75 | 45.75 | 45.75 |
| GMO (Peceol) | 28.88 | 28.88 | 28.88 |
| Labrafil M 2125 CS | 22.39 | 22.39 | 22.39 |
| Cremophor RH40 | 1 | | 0.33 |
| Tween 80 | | 1 | 0.67 |
| Lecithin | 0.99 | 0.99 | 0.99 |
| HPMC | 0.99 | 0.99 | 0.99 |
| TU solubility mg/gm | 384 | 368 | 366 |
| TU solubility mg/gm saturated with phytosterols | 393 | 410 | 410 |
| Percent change in solubility | 2.3 | 11.4 | 12.0 |

TABLE 15

| | % Composition (w/w) | |
|---|---|---|
| Formulation # | 40 | 41 |
| Castor oil | 30.00 | |
| Miglyol | | 30.00 |
| Lauryl glycol | 20.00 | 20.00 |
| Labrafil M 1944 CS | 15.00 | 15.00 |
| Cremophor RH40 | 35.00 | 35.00 |
| TU solubility mg/gm | 115 | 123 |
| TU solubility mg/gm saturated with phytosterols | 143 | 127 |
| Percent change in solubility | 24% | 3.3% |

Class VI: Formulations of T and TU with and without Phytosterol Saturation

Formulations 42-45 were prepared first without phytosterols and then saturated with phytosterols. First, the added T was used to estimate the amount of solid required to produce saturation. These samples were used to determine the solubility of T in the vehicles. As soon as the T loading was known (e.g., 1 day), the same vehicles were prepared with both T and TU above saturation.

TABLE 16

| Formulation # | Composition (% w/w) 42 | Composition (% w/w) 43 |
|---|---|---|
| Castor oil | 29.30 | — |
| Lauroglycol | 18.73 | — |
| Labrafil M 1944 CS | 13.95 | 13.83 |
| Cremophor RH40 | 34.08 | 11.64 |
| OA | — | 29.80 |
| GMO (Peceol) | — | 17.99 |
| Tween 80 | — | 22.80 |
| Lecithin | 0.95 | 0.95 |
| HPMC | 0.95 | 0.95 |
| Vit E | 1.99 | 1.99 |
| BHA | 0.05 | 0.05 |
| T alone solubility mg/gm | 40 | 38 |
| T alone solubility mg/gm saturated with phytosterols | 43 | 41 |
| Percent change in solubility | 7.5 | 7.9 |
| T solubility mg/gm in presence of saturated TU | 46 | 48 |
| T solubility mg/gm in presence of saturated TU saturated with phytosterols | 47 | 51 |
| Percent change in solubility | 2.2 | 6.3 |
| TU solubility mg/gm in presence of saturated T | 183 | 204 |
| TU solubility mg/gm in presence of saturated T and saturated with phytosterols | 205 | 218 |
| Percent change in solubility | 12.0 | 6.9 |

TABLE 17

| Ingredient | Formulation # 44 Composition (% w/w) |
|---|---|
| Oleic acid | 100 |
| T solubility mg/gm | 35 |
| T solubility mg/gm saturated with phytosterols | 54 |
| T solubility mg/gm in presence of saturated TU | 52 |
| T solubility mg/gm in presence of saturated TU saturated with phytosterols | 58 |
| Percent change in solubility | 11.5% |
| TU solubility mg/gm in presence of saturated T | 425 |
| TU solubility mg/gm in presence of saturated T and saturated with phytosterols | 431 |
| Percent change in solubility | 1.4% |

TABLE 18

| Ingredients | Formulation # 45 Composition (% w/w) |
|---|---|
| Oleic acid | 45.75 |
| GMO (Peceol) | 28.88 |
| Labrafil M 2125 CS | 22.39 |
| Tween 80 | 1 |
| Lecithin | 0.99 |
| HPMC | 0.99 |

TABLE 18-continued

| Ingredients | Formulation # 45 Composition (% w/w) |
|---|---|
| T solubility mg/gm | 51 |
| T solubility mg/gm saturated with phytosterols | 54 |
| T solubility mg/gm in presence of saturated TU | 51 |
| T solubility mg/gm in presence of saturated TU saturated with phytosterols | 55 |
| Percent change in solubility | 7.8 |
| TU solubility mg/gm in presence of saturated T | 358 |
| TU solubility mg/gm in presence of saturated T and saturated with phytosterols | 375 |
| Percent change in solubility | 4.7 |

TABLE 19

Class VII: Solubility of TU in Oleic Acid Based Formulation with Cholesterol, Stigmastanol (β-sitostanol) and β-sitosterol

| | Composition (% w/w) Formulation # | | | | |
|---|---|---|---|---|---|
| Ingredients | 46 OA | 47 OA | 48 OA-Chol | 49 OA-Stig | 50 OA-β-sitosterol |
| OA | 29.80 | 29.80 | 29.80 | 29.80 | 29.80 |
| GMO (Peceol) | 17.99 | 17.99 | 17.99 | 17.99 | 17.99 |
| Labrafil M 1944 CS | 13.83 | 13.83 | 13.83 | 13.83 | 13.83 |
| Cremophor RH40 | 11.64 | 11.64 | 11.64 | 11.64 | 11.64 |
| Tween 80 | 22.80 | 22.80 | 22.80 | 22.80 | 22.80 |
| Sterol | No sterols | Sat. w/ phytosterol | Sat. w/ Cholesterol | Sat. w/ Stigmastanol | Sat. w/β-sitosterol |
| Lecithin | 0.95 | 0.95 | 0.95 | 0.95 | 0.95 |
| HPMC | 0.95 | 0.95 | 0.95 | 0.95 | 0.95 |
| Vit E | 1.99 | 1.99 | 1.99 | 1.99 | 1.99 |
| BHA | 0.95 | 0.05 | 0.05 | 0.05 | 0.05 |
| TU solubility, mg/gm | 152 | 155 | 162 | 160 | 179 |
| Percent change in solubility compared to the 'no sterols' column | — | 2.0 | 6.6 | 5.3 | 17.8 |

TABLE 20

Clinical and animal study formulations

| | Unit Formulation % Formulation # | | |
|---|---|---|---|
| RAW MATERIAL | 51 (clinical) 52 (animal)* | 53 (clinical) 54 (animal)* | 55 (clinical) |
| Testosterone Undecanoate | 11.54 | 11.54 | 11.54 |
| Castor oil | 25.40 | | |
| Oleic acid | | 25.93 | 25.93 |
| Lipoid E PC S (Egg Lecithin) | 0.85 | 0.85 | 0.85 |
| Cremophor RH40 | 29.63 | 9.88 | 9.87 |
| Polysorbate-80 | | 19.74 | 19.73 |
| Labrafil M 1944 CS | 12.70 | 11.69 | 5.17 |
| Lauroglycol 90 | 16.93 | | |
| Glyceryl mono-oleate Type 40 | | 15.37 | 8.85 |
| Precirol ® | | | 13.26 |
| Phytosterols as CardioAid XF | 2.12 | 2.11 | 2.12 |

TABLE 20-continued

Clinical and animal study formulations

| | Unit Formulation % Formulation # | | |
|---|---|---|---|
| RAW MATERIAL | 51 (clinical) 52 (animal)* | 53 (clinical) 54 (animal)* | 55 (clinical) |
| Hypromellose 2910 (HPMC) | 0.85 | 0.85 | 0.85 |
| dl-α-Tocopherol | | 2.00 | 1.77 |
| Butylated Hydroxyanisole (BHA) | 0.05 | 0.05 | 0.05 |

*Formulations used for animal studies did not contain dl-α-Tocopherol or BHA.

For those formulations where the level of phytosterols was achieved by saturation, the level of phytosterols is from about 2% to about 20%. The level of solubilizers ranges from about 10% to about 90%. The level of surfactants ranges from about 1% to about 35%.

This example shows that formulations containing TU and/or T may be prepared from the compositions of Table 1-20 to contain the active agent in any concentration up to the solubility shown. In addition, the formulation may be further modified by addition of testosterone and/or testosterone ester beyond the solubility shown, while retaining useful dissolution and other pharmaceutical properties. FIG. 4 of Example 3 illustrates this modulation of properties.

Example 2

Preparation of Compositions Comprising Testosterone Undecanoate

Compositions comprising T, TU, and Phytosterol were prepared by weighing out the components in the described amount, placing the components into an appropriate container, mixing the components in an appropriate manner and, if necessary, heating to facilitate the solubilization of T, TU, and Phytosterols in the formulation. The formulations can be prepared by adding the components in any order. For example, T, TU, and phytosterols can be added to an individual component or into mixtures of two or more components. The composition can be prepared at room temperature or gently heated to 40-60° C. The composition can also be prepared by melting TU or Phytosterol and/or phytosterol esters at a temperature above the melting point, i.e., 64-66° C., followed by mixing it with other components. Traditional mixing techniques can be used, including, for example, mechanical agitation, stirring and sonication of the components. The clinical formulations 51, 53, and 55 were prepared using semi-automated equipment. A flow chart of a small-scale manufacturing process for preparation of pharmaceutical products suitable for clinical use is shown in FIG. 1. This process is suitable for the small scale manufacture of HPMC capsules, and it is a simple matter to adapt the process to gelatin capsules by replacing the HPMC banding solution with a gelatin banding solution. Other means of sealing capsules are also available, such as the LEMS™ system used with LiCaps™. Formulations containing only TU and Phytosterols were prepared by melting the mixture and cooling to room temperature. The solid was ground to a powder and filled into gelatin or HPMC capsules.

Formulations which are liquid at room temperature can be converted into free flowable powder or a waxy solid by addition of carriers or spraying the formulation on to an inert carrier. An example of preparing a solid powder is given below in Table 21. The liquid formulation was prepared by heating TU, excess phytosterols, and all other excipients at 70° C. for one day and cooled to room temp. Microcrystalline cellulose was added to absorb the formulation and yield a solid that was ground to a powder and filled in a HPMC capsule. The dissolution profile of the formulation is shown in FIG. 3.

Figure 3:
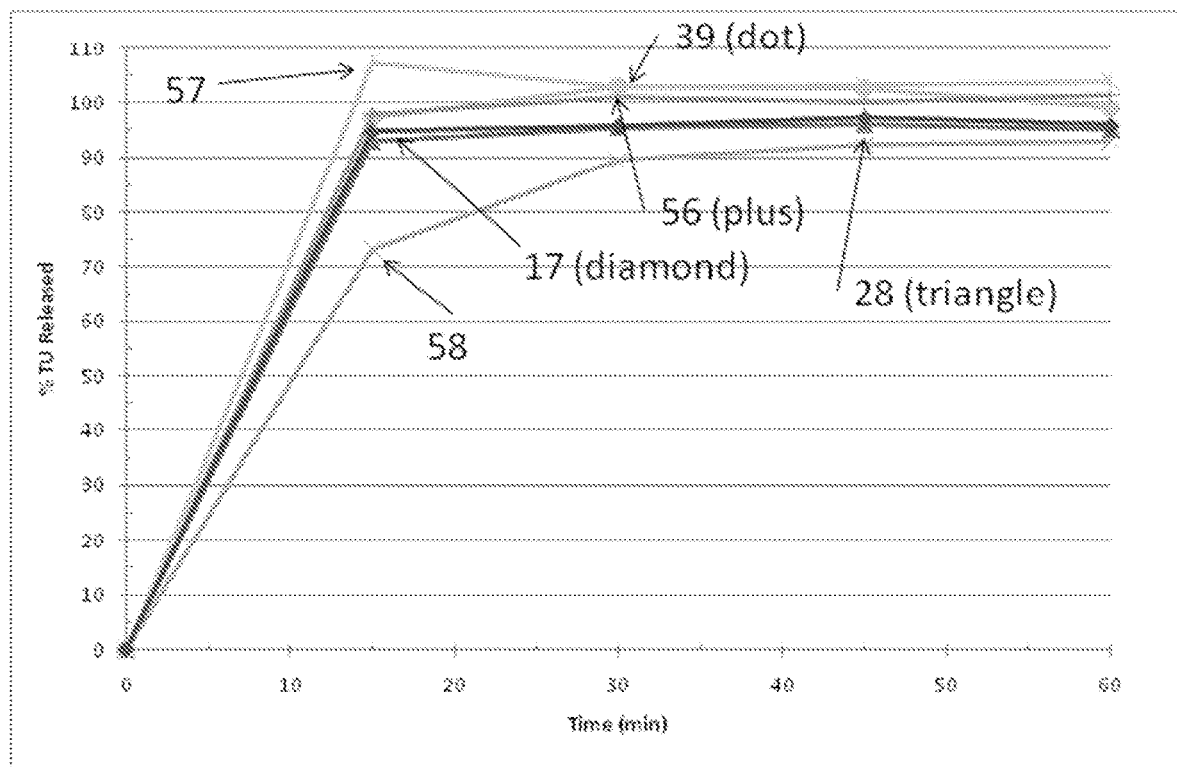
FIG. 3 shows dissolution curves of testosterone undecanoate Formulations 17 (Table 5), 28 (Table 10), 39 (Table 14), 56, 57 (Table 27) and 58 (Table 21).

The dissolution profiles of selected formulations prepared in the above manner and chosen from Table 2-21 are shown in FIGS. 2 and 3.

In FIG. 2, dissolution profiles are provided for all of TU formulations 51, 53 and 55 (Table 20); Formulation 9 (Table 2), and Capsules 2 and 4 of Example 1 from US2010/0173882. The data were obtained in a dissolution medium incorporating 2% TritonX-100 as a surfactant in the USP 2 apparatus in accordance with the present invention.

In FIG. 3, dissolution profiles are provided for all of TU Formulations 17 (Table 5), 28 (Table 10), 39 (Table 14), 56, 57 (Table 27) and 58 (Table 21). The data were obtained in a dissolution medium incorporating 2% TritonX-100 as a surfactant in the USP 2 apparatus in accordance with the present invention.

TABLE 21

| | Formulation # 58 |
|---|---|
| Ingredient | Composition (% w/w) |
| TU | 120 mg/gm |
| OA | 30.05 |
| GMO | 18.97 |
| Labrafil M 1944 CS | 14.71 |
| Cremophor RH40 | 11.44 |
| Tween 80 | 22.87 |
| Phytosterol | Saturated |
| Lecithin | 0.98 |
| HPMC | 0.98 |
| Microcrystalline Cellulose | 40 parts of microcrystalline cellulose were added to 60 parts of the above formulation. |

Example 3

Preparation of Compositions Comprising Testosterone Undecanoate and Phytosterols The percentage of phytosterol in the phytosterol-saturated formulations ranges from 2% to 20%. Three formulations are described in Table 22 containing between 5.8% and 44.6% phytosterols. FIG. 4 describes the dissolution profiles of these three formulations. Dissolution was measured in 900 mL of 25 mM phosphate buffer at pH 7.0 containing 0.1% SLS, obtained at 200 rpm using USP 2 apparatus. Formulation 59 illustrates the dissolution of a formulation with the properties of remaining a liquid a room temperature, while Formulation 60 is a suitable formulation which is solid at room temperature. Phytosterols in excess of the amount soluble at 70° C. may be added to the composition to modulate the release rate, as illustrated by the dissolution profile of Formulation 61 in FIG. 4. Formulation 61 further has the desirable property of being a sufficiently hard material that it may be reduced to a powder, which is fillable into a capsule by ordinary means. As can be seen from FIG. 4, phytosterols behave as delayed release agents due to their high log P (~12) and hydrophobic properties.

The formulations of Table 22 range in phytosterol composition from about 6% to 45% by weight. The same formulations range in TU composition from about 20% to about 72% by weight.

TABLE 22

Formulation compositions with phytosterols

| Component | Percent composition | | |
| --- | --- | --- | --- |
| | Formulation 59 | Formulation 60 | Formulation 61 |
| TU | 20.3% | 71.7% | 42.2% |
| Oleic acid | 18.5% | 6.7% | 4.0% |
| GMO | 11.1% | 4.0% | 2.4% |
| Labrafil M 1944 CS | 8.4% | 3.1% | 1.8% |
| Cremophor RH40 | 7.1% | 2.6% | 1.5% |
| Tween 80 | 14.1% | 5.1% | 3.0% |
| Phytosterols | 18.2% | 5.8% | 44.6% |
| Lyso Lecithin | 0.6% | 0.2% | 0.1% |
| HPMC | 0.6% | 0.2% | 0.1% |
| Vitamin E | 1.3% | 0.5% | 0.3% |

Example 4

In Vivo Dosing and PK Profile of Testosterone Undecanoate in Lipid Formulations A test was conducted of TU-containing lipid formulations for increased absorption in accordance with the methods of Shackleford et al., *J. Pharmacol. And Exptl. Therap.*, 2003, vol. 306, no. 3, pp. 925-933.

Test formulations were administered to four beagle dogs (body weight 8-10 kg) with food. The dosages were delivered as formulations consisting of two or three capsules. There were six different formulations in this study and they were identified by letters A through F.

Treatment A was a reference formulation of testosterone undecanoate (40 mg TU in a vehicle of 60:40 castor oil:lauroglycol, which is the formulation of the commercial product Andriol Testocap®). Treatments B through F all contained TU in castor oil base (Formulation 52 in Table 20) and are described in Table 23. All treatments, including the reference formulation contained a dosage of 80 mg per dog of TU, and one treatment also contained 100 mg of testosterone (T).

Whole venous blood samples of approximately 2.0 mL were collected from a peripheral vein of all animals for determination of serum concentrations of the reference or test article. Samples were collected at the following target time points at each dose: predose, 0.25, 0.5, 1, 2, 4, 6, 8 and 12 hours after administration.

Figure 5A:
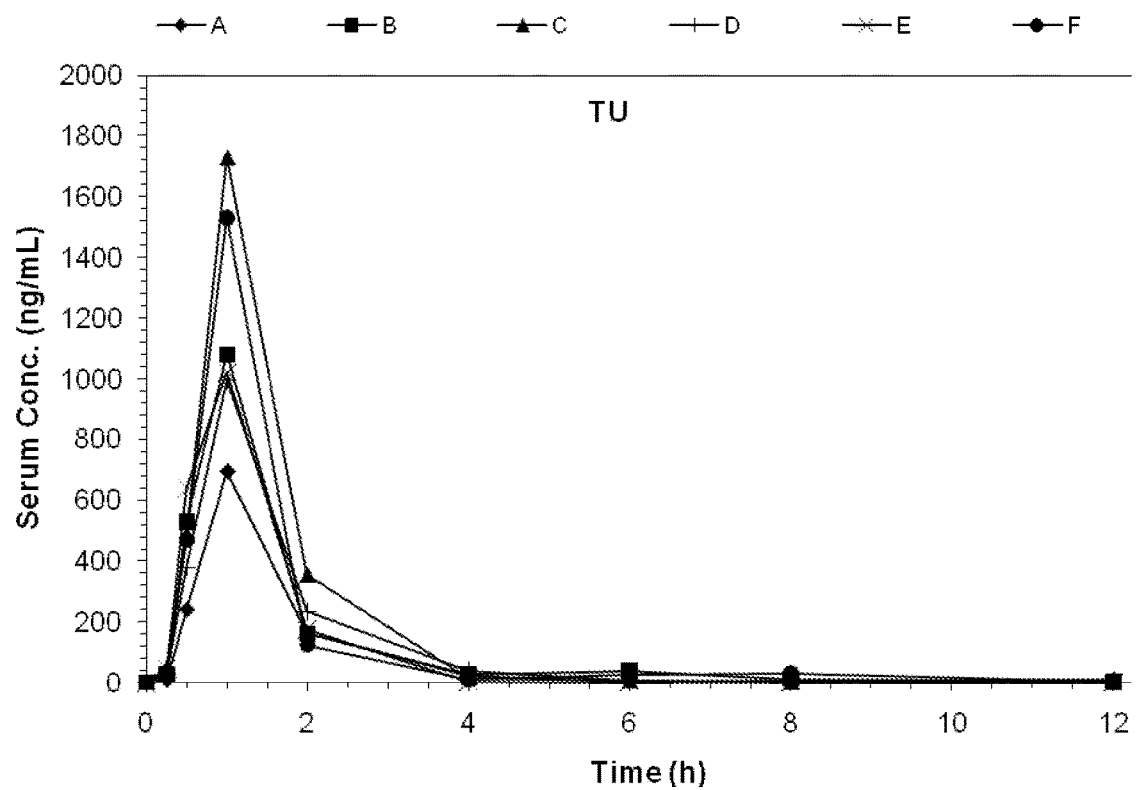
FIG. 5A is a mean PK profile of testosterone undecanoate resulting from treatments A through F described in Table 23 dosed to 4 beagle dogs after eating a high fat meal.
Figure 5B:
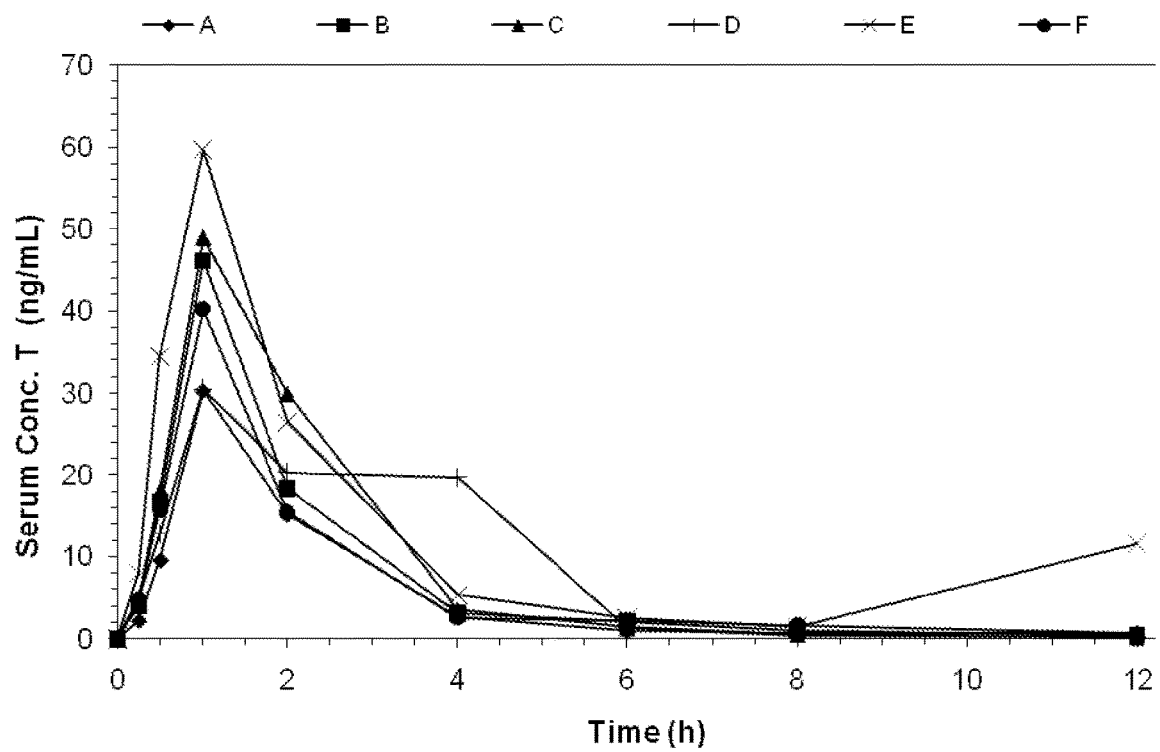
FIG. 5B is the mean PK profile of testosterone for the same treatments A-F.

Graphs of the results of serum concentration analyses for TU and T are provided in FIG. 5. It can be seen from FIG. 5 that significant TU absorption was observed with Formulation C (TU+castor oil+solubilized phytosterols+solid phytosterols), Formulation B (TU+castor oil+solubilized phytosterols) and Formulation D (TU+castor oil+solubilized phytosterols+phytosterols esters), as compared to reference Formulation A, lacking phytosterols.

The TU and T area under the curve (AUC) results and relative bioavailability were as follows:

TABLE 23

PK parameters from a formulation study in beagle dogs

| Treatment description | Mean TU exposure, ng*h/mL | Standard Deviation | Relative bioavailability (TU) | Mean T exposure, ng*h/mL | Standard Deviation | Relative bioavailability (T) |
| --- | --- | --- | --- | --- | --- | --- |
| A 80 mg TU in a formulation of 60:40 castor oil:lauroglycol | 1029.9 | 349.2 | 100% | 65.6 | 16 | 100% |
| B 80 mg TU as Formulation 52 | 1437.8 | 454.9 | 140% | 83.9 | 21 | 128% |
| C 80 mg TU as Formulation 52, co-dosed with 400 mg phytosterols | 2181.5 | 1124.0 | 212% | 99.7 | 20.7 | 152% |
| D 80 mg TU as Formulation 52, co-dosed with 640 mg phytosterol esters | 1357.5 | 829.6 | 132% | 62.1 | 19.8 | 95% |
| E 80 mg TU as Formulation 52, 100 mg of testosterone, 640 mg phytosterol esters | 1297.5 | 214.1 | 126% | 143 | 48.1 | 218% |
| F 80 mg TU as Formulation 52, 5 mg finasteride | 1700.0 | 867.8 | 165% | 76.4 | 13.4 | 116% |

This example demonstrates that the formulations of the present invention increase the absorption of TU up to 2-fold, as compared to a commercial formulation. The resulting T exposures are also increased.

Example 5

In Vivo Dosing and PK Profile of Testosterone Undecanoate in Lipid Formulations

This study consisted of two parts: Part 1 and Part 2. Part 1 of the study examined the effects of the metabolic inhibitors dutasteride and finasteride, and Part 2 examined the effect of 800 mg of phytosterols on T and DHT.

Part 1 consisted of two arms: a dutasteride arm and a finasteride arm. In the dutasteride arm four female Beagle dogs were dosed with 80 mg testosterone undecanoate (#52) and 400 mg phytosterol powder for three days (Days 3-5) followed by dutasteride at 2.5 mg (a one day loading dose; Day 6) and dutasteride at 0.5 mg for three more days (Days 7-9). These dogs then received 80 mg testosterone undecanoate (#52), 400 mg phytosterol powder, and 0.5 mg dutasteride for three days (days 10-12). The finasteride arm (four female Beagle dogs) was dosed identically to the dutasteride arm except finasteride at 5.0 mg was given instead of dutasteride, and the study lasted an additional three days (Days 13-15), during which 400 mg phytosterol only was dosed the first two days (Days 13, 14), and 80 mg TU in oleic acid formulation (#54) plus 400 mg phytosterols were dosed on Day 15. All testosterone undecanoate doses were administered to animals in the fed state.

Part 2 consisted of one arm and four female Beagle dogs were dosed with 80 mg testosterone undecanoate and 800 mg phytosterol powder for one day. All doses of testosterone undecanoate were administered to animals in the fed state.

Whole venous blood samples of approximately 2.0 mL were collected from a peripheral vein of all animals for determination of serum concentrations of T and DHT by LCMS. Samples were collected at the following target time points at each dose: predose, 0.25, 0.5, 1, 2, 4, 6, 8 and 12 hours after administration.

Figure 6:
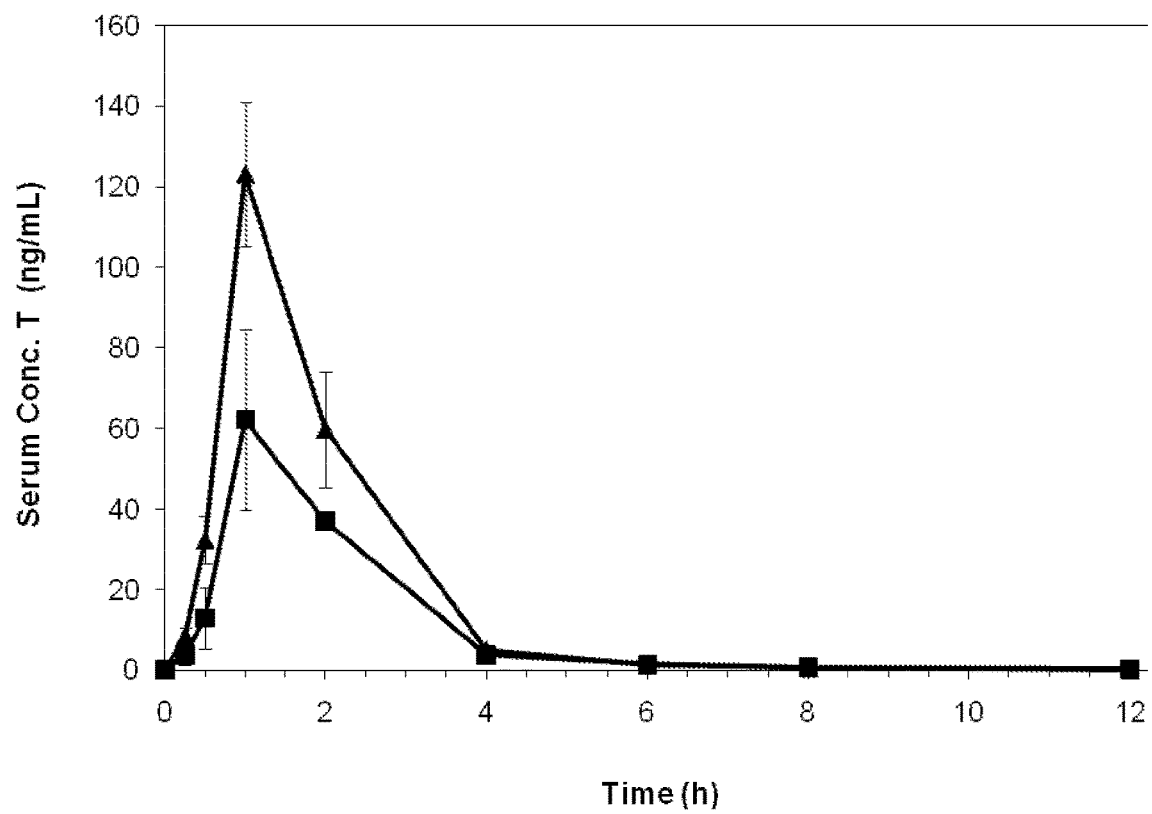
FIG. 6 shows the mean testosterone concentration in beagle dogs dosed with 80 mg testosterone undecanoate in Formulations 54 and 52 (Table 20). Values are the mean values obtained from a single group of 4 dogs. Phytosterols (400 mg) were co-dosed on both occasions

Graphs of the results of serum concentration analyses for testosterone are provided in FIG. 6. It can be seen from FIG. 6 that significant systemic T exposure was observed with the oleic acid formulation (#54) relative to the Castor oil formulation (#52). The DHT levels with the Oleic acid formulation were also significantly lower relative to the Castor oil formulation (#52) as shown in FIG. 10.

Graphs of the results of serum concentration analyses for T and DHT for the finasteride arm and the dutasteride arm are provided in FIGS. 7 & 8, respectively. It can be seen from FIGS. 7 & 8 that 5-alpha-reductase inhibitors had no significant effect on the T and DHT exposures.

Figure 9:
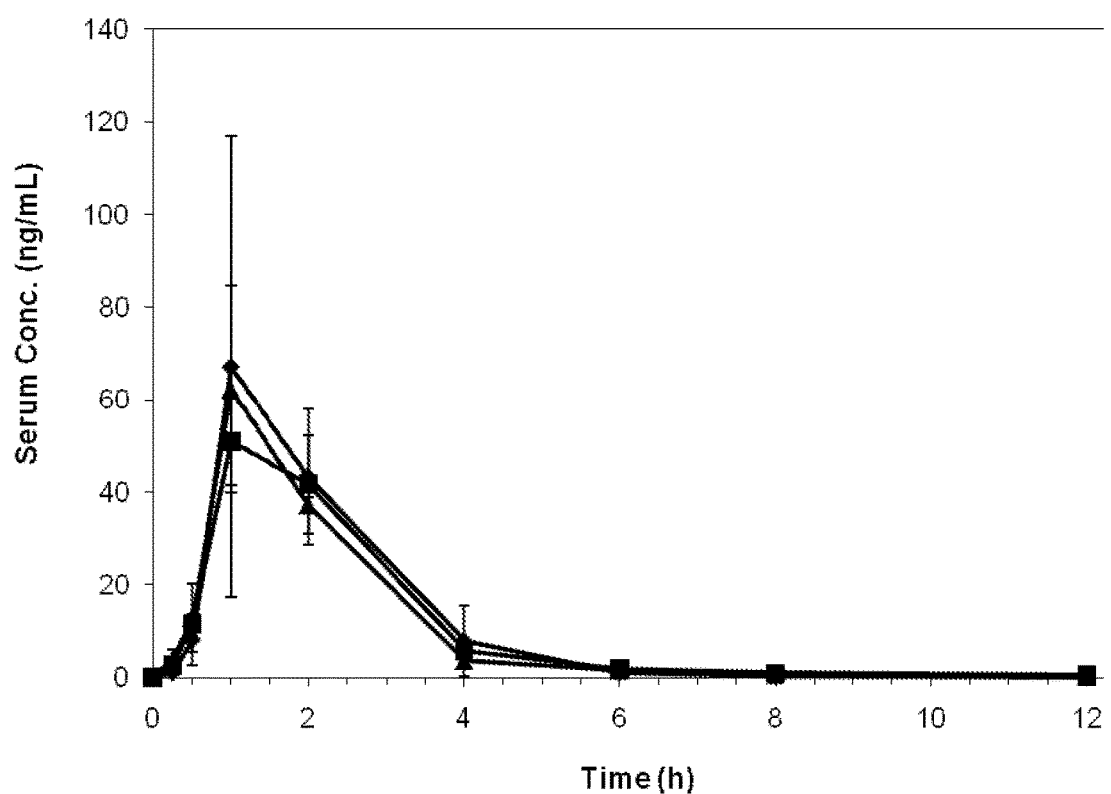
FIG. 9 shows the mean testosterone concentration profile in three beagle dog groups (4 per group) dosed with 80 mg testosterone undecanoate in formulation 52 (Table 20) and 400 or 800 mg of phytosterols.

Graphs of the results of serum concentration analyses for testosterone for Part 2 evaluating the effect of 800 mg of phytosterol vs. 400 mg in Part 1 using the castor oil formulation (#52) are provided in FIG. 9. It can be seen from FIG. 9 that there was no difference in T levels with increased levels of phytosterols.

Bar graphs of average T and DHT exposures (ng-h/mL) for all six treatments of TU formulations in beagle dogs in this study are given in FIG. 10. All treatments were co-dosed with 400 mg phytosterols except treatment L which was co-dosed with 800 mg of phytosterols. Error bars represent plus and minus one standard deviation.

Figure 11:
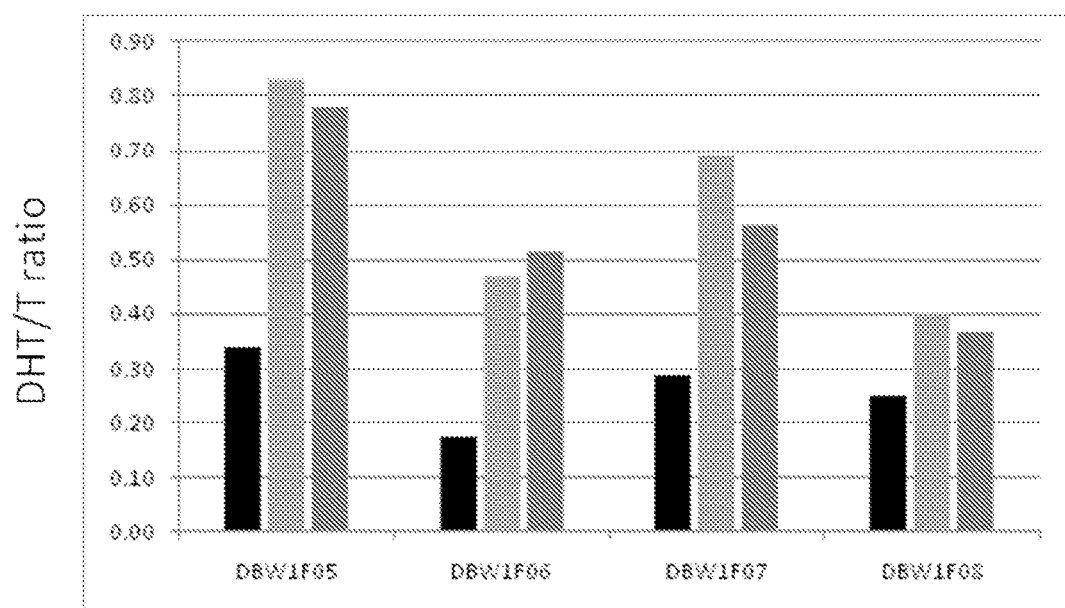
FIG. 11 shows the DHT/T ratios for 4 beagle dogs dosed with three treatments each containing 80 mg TU, as provided in Example 5. All treatments were co-dosed with 400 mg phytosterols.

It can be seen from FIG. 10 that oleic acid formulation gives the highest T level and lowest DHT level of all the treatments tested. The DHT/T ratio for this formulation is approaching the normal DHT/T value of 0.17 to 0.26 (FIG. 11). The numerical data for TU and T exposure and relative bioavailabilities for this study is given in Table 24 below.

TABLE 24

PK parameters from a formulation study in beagle dogs

| Treatment description | Mean TU exposure, ng*h/mL | Standard Deviation | Relative bioavailability TU[2] | Mean T exposure, ng*h/mL | Standard Deviation | Relative bioavailability (T)[2] | DHT/T ratio |
|---|---|---|---|---|---|---|---|
| G and I: Formulation 52 80 mg TU in a castor oil formulation, co-dosed with 400 mg phytosterols | 3110[1] | 947[1] | 302% | 123.6[1] | 16.4[1] | 188% | 0.49 |
| K Formulation 54 80 mg TU in an oleic acid formulation, co-dosed with 400 mg phytosterols | 3030 | 474 | 294% | 210 | 18.4 | 320% | 0.26 |
| H Formulation 52 80 mg TU in a castor oil formulation, co-dosed with 400 mg phytosterols, co-dosed with 0.5 mg dutasteride | 2680 | 989 | 260% | 132 | 27.9 | 201% | 0.77 |
| J: Formulation 52 80 mg TU in a castor oil formulation, co-dosed with 400 mg phytosterols, co-dosed with 5 mg finasteride | 1660 | 342 | 161% | 115 | 33.5 | 175% | 0.56 |
| L: Formulation 52 80 mg TU in a castor oil formulation, co-dosed with 800 mg phytosterols | 2630 | 969 | 255% | 138 | 30.6 | 210% | 0.27 |

[1]The mean values for Formulation 52 co-dosed with 400 mg phytosterols reflect the average of two groups of 4 beagle dogs (Treatments G and I).
[2]Referenced to the TU and T exposures of Treatment A, Table 23.

This example demonstrates that formulations of the present invention enhance TU absorption relative to the reference formulation (Treatment A of Table 23) by up to 3-fold. This example also demonstrates that resulting T exposures are increased up to 3-fold relative to the same reference formulation. It is also observed that the DHT/T ratios for Treatment K and L approach the normal physiological values in humans, versus other formulations.

Example 6

Lipid Dispersion Studies

The lipid dispersion test can be used to select formulations that maximize the amount of TU in the aqueous phase.

Buffer solution (100 mL) is prepared. Each test requires 36 mL with the following composition: 50 mM TRIS maleate/150 mM NaCl/5 mM $CaCl_2 \cdot 2H_2O$/5 mM Na taurodeoxycholate/1.25 mM lecithin.

TRIS, maleic acid, NaCl and $CaCl_2 \cdot 2H_2O$ are dissolved together. The buffer can be made to about 90% final volume, with adjustment of the pH to 6.8 with NaOH or HCl. Na taurodeoxycholate is dissolved into the solution. Lipoid E PC S should be removed from the freezer and allowed to thaw to room temperature in its bag with desiccant before removing it from the bag. Lecithin is dissolved, which requires stirring for several hours for the solution to clarify. The solution is quantitatively transferred back into a volumetric flask and diluted to volume with purified water. The final pH is checked and recorded it on the flask. Once the solution is made, it is stored in the refrigerator.

TABLE 25

| Dispersion media | | | | |
|---|---|---|---|---|
| Component | MW (g/mol) | Molarity (M) | Wt (g) to make 100 mL | Wt (g) to make 500 mL |
| TRIS (base) | 121.14 | 0.05 | 0.6057 | 3.0285 |
| Maleic acid | 116.08 | 0.05 | 0.5804 | 2.902 |
| NaCl | 58.44 | 0.15 | 0.8766 | 4.383 |
| CaCl2—2H2O | 147.02 | 0.005 | 0.07351 | 0.36755 |
| Na taurodeoxycholate (hydrate) | 521.7 | 0.005 | 0.26085 | 1.30425 |
| Lecithin (Lipoid E PC S) | 775 | 0.00125 | 0.096875 | 0.484375 |

Dispersion Experiment

Procedure: To the 36 mL of the dispersion buffer add 0.2 mL of formulation (initial test will use vehicle blank) quantitatively. Note that 0.2 mL per 40 mL is equivalent to about 1 mL in 200 mL, so it is a biorelevant amount. Draw samples every 15 minute to assess dissolution over 60 min; analyze for TU.

The results are presented in Table 26 below. The improved dispersion properties of the invention are evident in the percentage of TU solubilized. The Castor oil:lauroglycol formulation is the same composition as Andriol® Testocaps®.

TABLE 26

Results of dispersion testing of 60 mg of TU in Formulation 52 and castor oil:lauroglycol 60:40

| Formulation | TU percent contained in dispersed phase |
|---|---|
| Castor oil:lauroglycol 60:40 | 0% |
| Formulation 52 | 84.5% |

Example 7

Stability of Compositions Comprising Testosterone Undecanoate

The following formulations were stored at 60° C. for up to 2 weeks. The Iodine values for the formulations 56 and 57 were measured at 0, 1, and 2 weeks to assess the stability of the unsaturated excipients in the formulation, in the presence and absence of phytosterols.

TABLE 27

| | Formulation # | |
|---|---|---|
| | 56 | 57 |
| Ingredient | Composition (% w/w) | |
| TU | 120 mg/gm | 120 mg/gm |
| OA | 30.05 | 30.05 |
| GMO | 18.97 | 18.97 |
| Labrafil M 1944 CS | 14.71 | 14.71 |
| Cremophor RH40 | 11.44 | 11.44 |
| Tween 80 | 22.87 | 22.87 |
| Phytosterol | 0 | Saturated* |
| Lecithin | 0.98 | 0.98 |
| HPMC | 0.98 | 0.98 |

*Component percentages are taken before saturation of the vehicle with phytosterols at 70° C.

The iodine value $I_f$ is the number that expresses in grams the quantity of halogen, calculated as iodine, that can be fixed in the prescribed conditions by 100 g of the substance. Iodine value test per USP <401> Fats and Fixed Oils (Method 1) is used for determining the Iodine number. The method follows.

Procedure: Introduce the prescribed quantity of the substance to be examined (mg) into a 250 ml flask fitted with a ground-glass stopper and previously dried or rinsed with glacial acetic acid, and dissolve it in 15 ml of chloroform unless otherwise prescribed. Add very slowly 25.0 ml of iodine bromide solution. Close the flask and keep it in the dark for 30 min unless otherwise prescribed, shaking frequently. Add 10 ml of a 100 g/l solution of potassium iodide and 100 ml of water. Titrate with 0.1 M sodium thiosulphate, shaking vigorously until the yellow color is almost discharged. Add 5 ml of starch solution and continue the titration adding the 0.1 M sodium thiosulphate dropwise until the color is discharged ($n_1$ ml of 0.1 M sodium thiosulphate). Carry out a blank test under the same conditions ($n_2$ ml of 0.1 M sodium thiosulphate).

$$I_1 = \frac{1.269(n_2 - n_1)}{m}$$

Iodine number values after 1 and 2 weeks are given in Table 28. It can be seen from Table 28 that phytosterols minimize the degradation of the oxidation of the double bonds in the lipid-based formulations. This discovery enables longer shelf-life for oxidation-prone lipid-based formulations to be achieved.

TABLE 28

Stability results Iodine Test

| Formulation | Initial | 1 week at 60° C. | 2 weeks at 60° C. |
|---|---|---|---|
| 56 | 59.48 | 42.89 | 41.86 |
| 57 | 59.20 | 57.24 | 53.26 |

The clinical formulations 51, 53, and 55 the compositions of which are listed in Table 20 were stored at 25° C./60RH for 4 weeks. The TU content and impurities were measured at 0, and 4 weeks. Results at 0 and 4 weeks are given in Table 29.

TABLE 29

Stability results

| Formulation | Initial (related imps) | 4 weeks at 25° C./60 RH (related imps) |
|---|---|---|
| 51 | 101.8% (0.23) | 99.6% (0.50) |
| 53 | 100.4%(0.43) | 98.7%(1.11) |
| 55 | 101.8%(0.45) | 98.5%(0.92) |

The results in Table 28 demonstrate that phytosterols enhance the stability of formulations containing unsaturated fatty acids or glycerides. Table 29 demonstrates the acceptable stability of the clinical formulations 51, 53, and 55 (Table 20).

Example 8

In-Vivo Dosing and Prediction of Human PK Parameters of Compositions Comprising Testosterone Undecanoate Formulations 51, 53, and 55 were selected for assessment of PK profile in hypogonadal men. These capsules were manufactured according to Example 2, each capsule containing 40 mg of TU. Using accepted principles of allometric scaling and the direct comparison of the in-vivo results obtained with Andriol® Testocaps®, human clinical exposures are predicted as in Tables 30 and 31.

A randomized, single-dose, open-label, 5-period crossover study to evaluate the bioavailability, safety, and tolerability of four different testosterone undecanoate treatments versus a reference formulation (Andriol® Testocaps®) that is the current marketed formulation of TU was performed. Three investigational formulations 51, 53, and 55 comprised three of the treatments; the fourth treatment was a combination of the two (Formulations 53 and 55) of the investigational formulations. The study enrolled hypogonadal men that have low systemic testosterone levels but do not exhibit clinical symptoms at such levels (i.e., the subjects are asymptomatic).

A total of 8 subjects were enrolled to receive a single dose of each of the four test treatments (80 mg TU per dose) and the reference formulation (80 mg TU as Andriol® Testocaps®) under fed conditions in crossover fashion. Subjects were randomized to treatment sequence with a washout period of 24 hours (period 1 to 3 for Andriol® Testocaps®, formulation 51 and 53) or 48 hours (period 4 and 5 for formulations 55 and 53+55) between each blinded administration of study drug. Each dose of study drug was immediately preceded by a standard meal to allow for dosing in the fed state.

Serial blood samples for serum PK analysis of testosterone and dihydrotestosterone (DHT) levels were collected at 0 (pre-dose), 0.5, 1, 2, 3, 4, 5, 6, 8, 10, 12, 14, 24 and additional 16 and 48 (period 4 and 5) hours after dosing of each of the test and reference TU formulations to characterize single-dose bioavailability and pharmacokinetics. Vitals signs, AEs, clinical labs, ECGs, and urinalysis was assessed pre-dose and at various times through discharge.

Based on the dog PK data on Andriol® Testocaps® and formulations 52 and 54 and available human data on Andriol® Testocaps®, the predicted human Cavg for formulations 51 and 53 is given in Tables 30 and 31. Note that Formulations 51 and 53 are derived from Formulations 52 and 54 by addition of minor amounts of antioxidants. For comparison, the steady state testosterone $C_{avg}$ of a SEDDS formulation from Clarus Therapeutics with a dose of 316 mg of TU (200 mg T equivalent) is 514 ng/dL (Roth et al, International Journal of Andrology, on-line issue October 2010).

Allometric scaling was carried out using the published method contained in guidance published by the Food and Drug Administration of the United States (FDA), in Guidance for Industry: Estimating the Maximum Safe Starting Dose in Initial Clinical Trials for Therapeutics in Adult Healthy Volunteers, published in July 2005. The factor of 0.54 is used to convert from mg/kg dosing in dogs to the approximate equivalent dose in humans. In the in-vivo study in beagle dogs, the TU dose was 80 mg, the average animal weight 9.4 kg, and the dose/kg body weight is 8.5 mg/kg. The equivalent human dose is 8.5 mg/kg×0.54=4.6 mg/kg. For a proposed human dose of 80 mg, and an average adult male weight of 60 kg, the dose/kg body weight would be 1.3 mg/kg. Assuming linear pharmacokinetics for T-exposure resulting from the dosing of TU, the resulting predicted human exposure factor for the 80 mg human dose is (1.3/4.6)=0.28.

TABLE 30

Predicted human PK parameters for testosterone for Formulations 52 and 54 by allometric scaling

| Formulation | AUC (0-12) (ng-h/mL) |
|---|---|
| Formulation 52 result in dogs | 99.7 |
| Predicted human PK parameter of Formulation 51 | 27.9 |
| Formulation 54 result in dogs | 210 |
| Predicted human PK parameter of Formulation 53 | 58.8 |

A direct comparison of the T exposure ($C_{max}$ and AUC) between dogs and humans is also possible based on published data for Andriol® Testocaps® (Bagchus et al). The resulting predicted values of the AUC (0-12 hr) exposure is somewhat higher than the allometric approach using the direct comparison approach.

TABLE 31

Predicted human PK parameters for 80 mg TU dose for Formulations 52 and 54 by direct comparison method

| Composition or formulation | Cmax ng/mL | AUC 0-12 hrs ng-h/mL |
|---|---|---|
| Dog: 60:40 castor oil:lauroglycol FCC | 7.7[1] | 35.6[1] |
| Human: 60:40 castor oil:lauroglycol FCC | 32.9[2] | 65.6[2] |

TABLE 31-continued

Predicted human PK parameters for 80 mg TU dose for
Formulations 52 and 54 by direct comparison method

| Composition or formulation | Cmax ng/mL | AUC 0-12 hrs ng-h/mL |
|---|---|---|
| Ratio dog:human: | 0.23 | 0.54 |
| Formulation 52 result in dogs | 53.6 | 99.7 |
| Predicted human PK parameters of Formulation 51[3] | 12.5 | 54.1 |
| Formulation 54 result in dogs | 123 | 210 |
| Predicted human PK parameters of Formulation 53[3] | 28.8 | 113.4 |

[1]Treatment in beagle dogs is the same composition as published for Andriol ® Testocaps ® except filled into hard gelatin capsules.
[2]Testocaps ® from Andriol ® Testocaps ® web site, W M Bagchus, F Maris, P G Schnabel, N S Houwing, Dose Proportionality of Andriol ® Testocaps ™)
[3]Phytosterols, 400 mg, co-administered with Formulations 52 and 54 to dogs.
4. Formulations 51 and 53 will be co-administered in humans with phytosterols, 400 mg.

Figure 12:
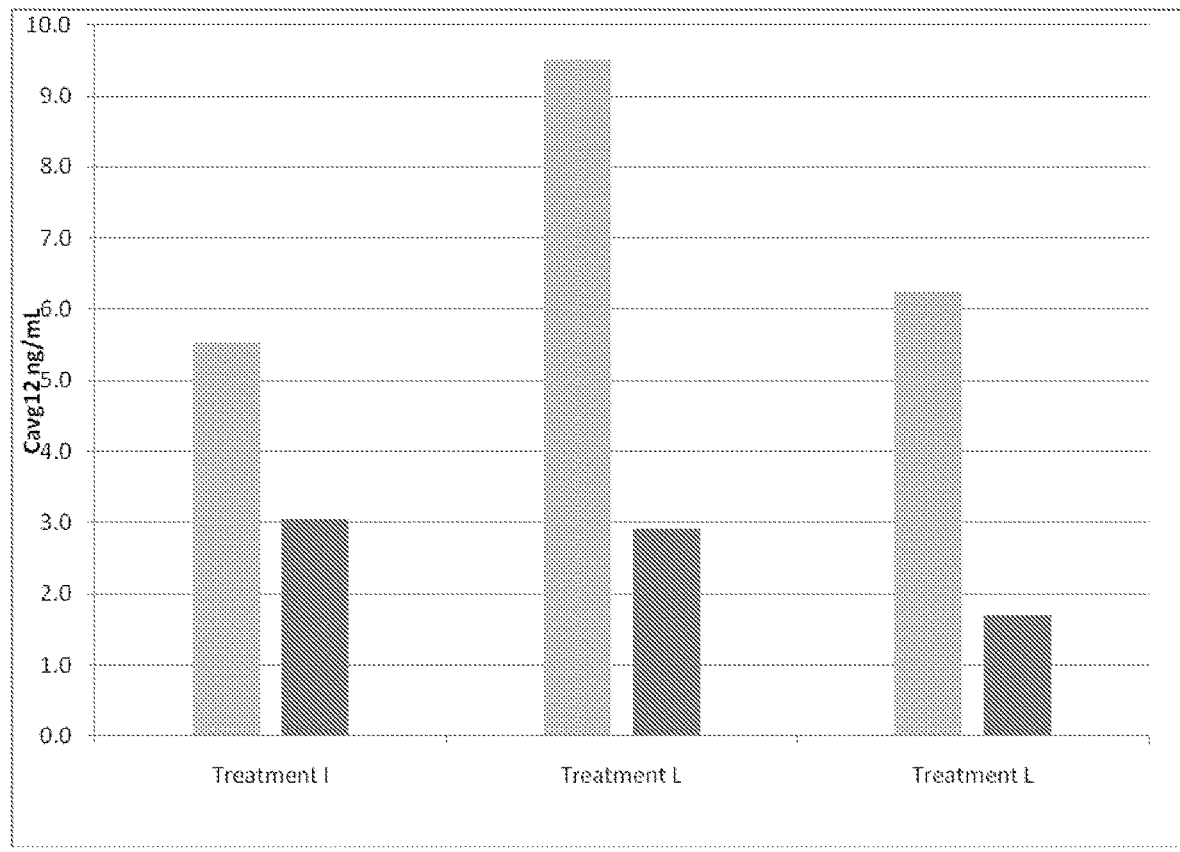
FIG. 12 shows the predicted average human concentrations of testosterone and DHT resulting from dosing with Treatments I, K, and L as described in Table 24.

FIG. 12 shows the predicted average human concentrations of T and DHT resulting from dosing with Formulations 51 and 53. Treatment I is Formulation 51 co-dosed with 400 mg phytosterols. Treatment K is Formulation 53 co-dosed with 400 mg phytosterols. Treatment L is Formulation 51 co-dosed with 800 mg phytosterols. The predictions of human exposure are based on extrapolation of in vivo results in beagle dogs, using the beagle dog and human PK parameters for a reference formulation of TU in 60% castor oil and 40% lauroglycol.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

The invention claimed is:

1. An oral formulation comprising:
   a) testosterone undecanoate;
   b) from about 10% to about 90% by weight of a non-sterol solubilizing agent effective for solubilization of the testosterone undecanoate; and
   c) from about 2% to about 45% by weight of a mixture of phytosterols or phytosterol esters, wherein the mixture comprises from 40% to 58% by weight of beta-sitosterol or esters thereof; from 20% to 30% by weight of campesterol or esters thereof; from 14% to 22% by weight stigmasterol or esters thereof; from 0 to 6% by weight brassicasterol or esters thereof; from 0 to 5% by weight sitostanol or esters thereof; and from 0 mg/g to 15 mg/g tocopherols;
   wherein the phytosterols or phytosterol esters provides increased plasma levels of testosterone following oral administration in comparison to the plasma levels of testosterone produced following oral administration of testosterone undecanoate in a formulation free of phytosterols and phytosterol esters.

2. The oral formulation of claim 1, wherein the oral formulation comprises from 40 to 400 mg of testosterone undecanoate.

3. The oral formulation of claim 1, wherein the oral formulation comprises from 0.1 to 40% by weight testosterone undecanoate.

4. The oral formulation of claim 1, wherein the oral formulation comprises from about 12.5% to about 85% by weight non-sterol solubilizing agent.

5. The oral formulation of claim 1, wherein the non-sterol solubilizing agent is selected from lipids, surfactants, and mixtures thereof.

6. The oral formulation of claim 5, wherein the non-sterol solubilizing agent comprises an ester of a monohydric alcohol with an organic acid.

7. The oral formulation of claim 1, wherein the non-sterol solubilizing agent comprises propylene glycol monolaurate.

8. The oral formulation of claim 1, wherein the non-sterol solubilizing agent comprises polyoxyl 40 hydrogenated castor oil.

9. The oral formulation of claim 1, wherein the oral formulation comprises:
   a) from 0.1 to 40% by weight testosterone undecanoate;
   b) from about 10% to about 90% by weight the non-sterol solubilizing agent effective for solubilization of the testosterone undecanoate; and
   c) from about 2% to about 45% by weight the mixture of phytosterols or phytosterol esters, wherein the mixture comprises from 40% to 58% by weight of beta-sitosterol or esters thereof; from 20% to 30% by weight of campesterol or esters thereof; from 14% to 22% by weight stigmasterol or esters thereof; from 0 to 6% by weight brassicasterol or esters thereof; from 0 to 5% by weight sitostanol or esters thereof; and from 0 mg/g to 15 mg/g tocopherols.

10. The oral formulation of claim 9, wherein the oral formulation comprises from 12.5 to 85% by weight non-sterol solubilizing agent.

11. The oral formulation of claim 9, wherein the non-sterol solubilizing agent comprises propylene glycol monolaurate.

12. The oral formulation of claim 9, wherein the non-sterol solubilizing agent comprises polyoxyl 40 hydrogenated castor oil.

13. The oral formulation of claim 9, wherein the oral formulation is self-emulsifying or self-microemulsifying.

14. The oral formulation of claim 9, wherein the oral formulation further comprises alpha-tocopherol or alpha-tocopherol acetate.

15. The oral formulation of claim 9, wherein the phytosterols or phytosterol esters provides enhanced absorption of the testosterone undecanoate, as compared to the absorption of the testosterone undecanoate without the phytosterols or phytosterol esters.

* * * * *